(12) United States Patent
Fernandez-Salas et al.

(10) Patent No.: US 7,598,027 B2
(45) Date of Patent: Oct. 6, 2009

(54) BOTULINUM TOXIN SCREENING ASSAYS

(75) Inventors: Ester Fernandez-Salas, Fullerton, CA (US); Patton E. Garay, Long Beach, CA (US); Kei Roger Aoki, Garden Grove, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 10/598,073

(22) PCT Filed: Feb. 23, 2005

(86) PCT No.: PCT/US2005/006421

§ 371 (c)(1),
(2), (4) Date: Aug. 17, 2006

(87) PCT Pub. No.: WO2005/082096

PCT Pub. Date: Sep. 9, 2005

(65) Prior Publication Data

US 2008/0003240 A1 Jan. 3, 2008

Related U.S. Application Data

(60) Provisional application No. 60/547,591, filed on Feb. 24, 2004.

(51) Int. Cl.
*A61K 39/02* (2006.01)
*A61P 31/00* (2006.01)
*C12Q 1/02* (2006.01)

(52) U.S. Cl. .............................. 435/4; 435/23; 435/69.1

(58) Field of Classification Search ........................ None
See application file for complete search history.

(56) References Cited

U.S. PATENT DOCUMENTS

| | | | |
|---|---|---|---|
| 5,750,365 A | 5/1998 | Chiu et al. | |
| 5,925,528 A | 7/1999 | Chiu | |
| 6,913,877 B1 * | 7/2005 | Chaplen et al. | 435/4 |
| 7,183,066 B2 * | 2/2007 | Fernandez-Salas et al. | 435/7.32 |
| 7,208,285 B2 * | 4/2007 | Steward et al. | 435/7.32 |
| 7,264,946 B2 * | 9/2007 | Bogin et al. | 435/69.1 |
| 2003/0219462 A1 * | 11/2003 | Steward et al. | 424/239.1 |
| 2004/0013687 A1 * | 1/2004 | Simpson et al. | 424/190.1 |
| 2004/0014024 A1 | 1/2004 | Yayon et al. | |

(Continued)

FOREIGN PATENT DOCUMENTS

WO WO 02/102854 12/2002

(Continued)

OTHER PUBLICATIONS

Keller, James E. et al, FEBS Letters, vol. 456, 1999, pp. 137-142, Persistence of botulinum neurotoxin action in cultured spinal cord cells.*

(Continued)

*Primary Examiner*—Robert B Mondesi
*Assistant Examiner*—Ginny Portner
(74) *Attorney, Agent, or Firm*—Dean G. Stathakis; Joel B. German; Debra Condino

(57) ABSTRACT

Methods for detecting BoNT/A activity in a sample, methods for screening molecules able to compete with BoNT/A receptor binding, methods for reducing BoNT/A activity in a human and methods of marketing a neurotoxin capable of selectively binding to FGFR3 to a governmental or regional regulatory authority.

29 Claims, 13 Drawing Sheets

U.S. PATENT DOCUMENTS

| | | | |
|---|---|---|---|
| 2004/0058348 A1* | 3/2004 | Bogin et al. | 435/6 |
| 2004/0072270 A1 | 4/2004 | Fernandez-Salas et al. | |
| 2004/0204388 A1* | 10/2004 | Lynch et al. | 514/151 |
| 2005/0123567 A1* | 6/2005 | First | 424/239.1 |
| 2005/0129677 A1* | 6/2005 | Li et al. | 424/130.1 |
| 2005/0148511 A1* | 7/2005 | Bogin et al. | 514/12 |
| 2006/0078900 A1* | 4/2006 | Mendrick et al. | 435/6 |
| 2006/0127914 A1* | 6/2006 | Yon et al. | 435/6 |
| 2007/0118934 A1* | 5/2007 | Yu et al. | 800/288 |
| 2007/0135514 A1* | 6/2007 | Lynch et al. | 514/424 |
| 2008/0064054 A1* | 3/2008 | Fernandez-Salas et al. | 435/29 |
| 2008/0160561 A1* | 7/2008 | Fernandez-Salas et al. | 435/29 |
| 2008/0182799 A1* | 7/2008 | Fernandez-Salas et al. | 435/29 |

FOREIGN PATENT DOCUMENTS

| | | |
|---|---|---|
| WO | WO 02/102972 | 12/2002 |
| WO | WO 02/102973 | 12/2002 |
| WO | WO 2004/110487 | 12/2004 |

OTHER PUBLICATIONS

Dong, min et al, Science, vol. 312, Apr. 28, 2006, pp. 592-596, SV2 is the protein receptor for Botulinum neurotoxin A.*

Keller et al, 1999, reference of record.*

Aoki, KR, Future Aspects of Botulinum neurotoxins, Journal of Neural Transmission, vol. 115(4), Apr. 2008, pp. 567-573.*

Maksymowych, A.B e tal, Binding and Trnascytosis of Botulinum Nuerotoxin by Polarized Human colon carcinoma cells, The Journal of Biological Chemistry, vol. 273(34), Aug. 21, 1998, pp. 21950-21957.*

Stecher, B et al, Federation of European Biochemical Societies, vol. 248(1-2), pp. 23-27, May 1989, Reduction chain separation of botulinum A toxin-a prerequisite to its inhibitory action on exocytosis in chromaffin cells.*

Daniels-Holgate, P.U. et al, Journal of Neuroscience Research, vol. 44, pp. 263-271, 1996, Productive and non-productive binding of botulinum neurotoxin A to motor nerve endings are distinguished by Its heavy chain.*

Lalli, Giovanna et al, Journal of Cell Science, vol. 112, pp. 2715-2724, 1999, Functional characterization of tetanus and botulinum neurotoxins binding domains.*

Lacy, D. Borden et al, Nature Structural Biology, vol. 5(10), Oct. 1998, Crystal structure of botulinum neurotoxin type A and implications for toxicity.*

Schiavo, Giampietro et al, Physiol. Rev., vol. 80, pp. 717-766, 2000.*

Onose, Hiroyuki et al, European Journal of Endocrinology, 1999, vol. 140, pp. 169-173, Overexpression of fibroblast growth factor receptor 3 in a human thyroid carcinoma cell line results in overgrowth of the confluent cultures.*

Nemoz-Gaillard, Eric et al, Expression of SNARE proteins in neteroendocrine cell lines and functional role of tetanus toxin- sensitive protein in cholecystokinin release.*

L-M. Sturla et al., FGFR3IIIS: a novel soluble FGFR3 spliced variant that modulates growth is frequently expressed in tumour cells, 89(7) Br. J. Cancer 1276-1284 (2003).

M. Kanai et al., Signal transduction pathway of human fibroblast growth factor receptor 3. Identification of a novel 66-kDa phosphoprotein, 272(10) J. Biol. Chem 6621-6628 (1997).

Janet E. Henderson et al., Expression of FGFR3 with the G380R achondroplasia mutation inhibits proliferation and maturation of CFK2 chondrocytic cells, 15(1) J. Bone Miner. Res. 155-165 (2000).

Noriko Yokosawa et al., Binding of Clostridium botulinum type C neurotoxin to different neuroblastoma cell lines, 57(1) Infect. Immun. 272-277 (1989).

Noriko Yokosawa et al., Binding of botulinum type Cl, D and E neurotoxins to neuronal cell lines and synaptosomes, 29(2) Toxicon 261-264 (1991).

Tei-ichi Nishiki et al., Identification of protein receptor for Clostridium botulinum type B neurotoxin in rat brain synaptosomes, 269(14) J. Biol. Chem. 10498-10503 (1994).

Hiroyuki Onose et al., Over-expression of fibroblast growth factor receptor 3 in a human thyroid carcinoma cell line results in overgrowth of the confluent cultures, 140(2) Eur. J. Endocrinol. 169-173 (1999).

Elizabeth E. Plowright et al., Ectopic expression of fibroblast growth factor receptor 3 promotes myeloma cell proliferation and prevents apoptosis, 95(3) Blood 992-998 (2000).

Yukako Fujinaga et al., Molecular characterization of binding subcomponents of Clostridium botulinum type C progenitor toxin for intestinal epithelial cells and erythrocytes, 150(Pt 5) Microbiology 1529-1538 (2004).

Atsushi Nishikawa et al., The receptor and transporter for internalization of Clostridium botulinum type C progenitor toxin into HT-29 cells, 319(2) Biochem. Biophys. Res. Commun. 327-333 (2004).

Erik A. Mijan and Eric G. Bremer, Regulation of Growth Factor Receptors by Gangliosides, 2002(160)Sci. STKE.RE15(2002).

Akio Shimizu et al, A novel alternatively spliced fibroblast growth factor receptor 3 isoform lacking the acid box domain is expressed during chondrogenic differentiation of ATDC5 cells, 276(14) J. Biol. Chem. 11031-11040 (2001).

C. J. Powers et al., Fibroblast growth factors, their receptors and signaling 7(3)Endocr. Relat. Cancer. 165-197 (2000).

Bernhard Reuss & Oliver von Bohlen und Halbach, Fibroblast growth factors and their receptors in the central nervous system, 313(2) Cell Tissue Res. 139-157 (2003).

* cited by examiner

SNAP-25$_{197}$ ▶

Neuro-2A

SNAP-25$_{197}$ ▶

SH-SY5Y

SNAP-25$_{197}$ ▶

Neuro-2A

SNAP-25$_{197}$ ▶

Neuro-2A

Neuro-2A

SEQUENCE LISTING

```
<160> NUMBER OF SEQ ID NOS: 32

<210> SEQ ID NO 1
<211> LENGTH: 2427
<212> TYPE: DNA
<213> ORGANISM: Homo sapiens

<400> SEQUENCE: 1
atgggcgccc ctgcctgcgc cctcgcgctc tgcgtggccg tggccatcgt ggccggcgcc      60
tcctcggagt ccttggggac ggagcagcgc gtcgtgggc gagcggcaga agtcccgggc     120
ccagagcccg gccagcagga gcagttggtc ttcggcagcg gggatgctgt ggagctgagc     180 tgtccccgc ccggggtgg tcccatgggg cccactgtct gggtcaagga tggcacaggg     240
```

-continued

```
ctggtgccct cggagcgtgt cctggtgggg ccccagcggc tgcaggtgct gaatgcctcc      300
cacgaggact ccggggccta cagctgccgg cagcggctca cgcagcgcgt actgtgccac      360
ttcagtgtgc gggtgacaga cgctccatcc tcgggagatg acgaagacgg ggaggacgag      420
gctgaggaca caggtgtgga cacaggggcc ccttactgga cacggcccga gcggatggac      480
aagaagctgc tggccgtgcc ggccgccaac accgtccgct ccgctgccc agccgctggc       540
aaccccactc cctccatctc ctggctgaag aacggcaggg agttccgcgg cgagcaccgc      600
attggaggca tcaagctgcg gcatcagcag tggagcctgg tcatggaaag cgtggtgccc      660
tcggaccgcg gcaactacac ctgcgtcgtg gagaacaagt ttggcagcat ccggcagacg      720
tacacgctgg acgtgctgga gcgctccccg caccggccca tcctgcaggc ggggctgccg      780
gccaaccaga cggcggtgct gggcagcgac gtggagttcc actgcaaggt gtacagtgac      840
gcacagcccc acatccagtg gctcaagcac gtggaggtga acggcagcaa ggtgggcccg      900
gacggcacac cctacgttac cgtgctcaag tcctggatca gtgagagtgt ggaggccgac      960
gtgcgcctcc gcctggccaa tgtgtcggag cgggacgggg cgagtacct ctgtcgagcc      1020
accaatttca taggcgtggc cgagaaggcc ttttggctga gcgttcacgg gccccgagca      1080
gccgaggagg agctggtgga ggctgacgag gcggcagtg tgtatgcagg catcctcagc      1140
tacggggtgg gcttcttcct gttcatcctg gtggtggcgg ctgtgacgct ctgccgcctg      1200
cgcagccccc ccaagaaagg cctgggctcc ccaccgtgc acaagatctc ccgcttcccg       1260
ctcaagcgac aggtgtccct ggagtccaac cgtccatga gctccaacac accactggtg       1320
cgcatcgcaa ggctgtcctc agggagggc cccacgctgg ccaatgtctc cgagctcgag       1380
ctgcctgccg acccccaaatg ggagctgtct cgggccggc tgaccctggg caagccctt       1440
ggggagggct gcttcggcca ggtggtcatg gcggaggcca tcggcattga caaggaccgg      1500
gccgccaagc ctgtcaccgt agccgtgaag atgctgaaag acgatgccac tgacaaggac      1560
ctgtcggacc tggtgtctga gatggagatg atgaagatga tcgggaaaca caaaaacatc      1620
atcaacctgc tgggcgcctg cacgcagggc gggccctgt acgtgctggt ggagtacgcg       1680
gccaagggta acctgcggga gtttctgcgg gcgcggcggc cccgggcct ggactactcc       1740
ttcgacacct gcaagccgcc cgaggagcag ctcaccttca ggacctggt gtcctgtgcc       1800
taccaggtgg cccggggcat ggagtacttg gcctcccaga agtgcatcca cagggacctg      1860
gctgcccgca atgtgctggt gaccgaggac aacgtgatga gatcgcaga cttcgggctg       1920
gcccgggacg tgcacaacct cgactactac aagaagacaa ccaacggccg gctgccgtg       1980
aagtggatgg cgcctgaggc cttgtttgac cgagtctaca ctcaccagag tgacgtctgg      2040
tcctttgggg tcctgctctg ggagatcttc acgctggggg gctccccgta ccccggcatc      2100
cctgtggagg agctcttcaa gctgctgaag gagggccacc gcatggacaa gcccgccaac      2160
tgcacacacg acctgtacat gatcatgcgg gagtgctggc atgccgcgcc ctcccagagg      2220
cccaccttca gcagctggt ggaggacctg accgtgtcc ttaccgtgac gtccaccgac        2280
gagtacctgg acctgtcggc gcctttcgag cagtactccc cgggtggcca ggacaccccc      2340
agctccagct cctcagggga cgactccgtg tttgcccacg acctgctgcc cccggcccca      2400
cccagcagtg ggggctcgcg gacgtga                                          2427
```

<210> SEQ ID NO 2
<211> LENGTH: 808
<212> TYPE: PRT

<213> ORGANISM: Homo sapiens

<400> SEQUENCE: 2

```
Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Ser Trp Ile Ser Glu Ser Val Glu Ala Asp
305                 310                 315                 320

Val Arg Leu Arg Leu Ala Asn Val Ser Glu Arg Asp Gly Gly Glu Tyr
                325                 330                 335

Leu Cys Arg Ala Thr Asn Phe Ile Gly Val Ala Glu Lys Ala Phe Trp
            340                 345                 350

Leu Ser Val His Gly Pro Arg Ala Ala Glu Glu Glu Leu Val Glu Ala
        355                 360                 365

Asp Glu Ala Gly Ser Val Tyr Ala Gly Ile Leu Ser Tyr Gly Val Gly
    370                 375                 380

Phe Phe Leu Phe Ile Leu Val Val Ala Ala Val Thr Leu Cys Arg Leu
385                 390                 395                 400
```

-continued

```
Arg Ser Pro Pro Lys Lys Gly Leu Gly Ser Pro Thr Val His Lys Ile
            405                 410                 415
Ser Arg Phe Pro Leu Lys Arg Gln Val Ser Leu Glu Ser Asn Ala Ser
            420                 425                 430
Met Ser Ser Asn Thr Pro Leu Val Arg Ile Ala Arg Leu Ser Ser Gly
            435                 440                 445
Glu Gly Pro Thr Leu Ala Asn Val Ser Glu Leu Glu Leu Pro Ala Asp
            450                 455                 460
Pro Lys Trp Glu Leu Ser Arg Ala Arg Leu Thr Leu Gly Lys Pro Leu
465                 470                 475                 480
Gly Glu Gly Cys Phe Gly Gln Val Val Met Ala Glu Ala Ile Gly Ile
                    485                 490                 495
Asp Lys Asp Arg Ala Ala Lys Pro Val Thr Val Ala Val Lys Met Leu
                500                 505                 510
Lys Asp Asp Ala Thr Asp Lys Asp Leu Ser Asp Leu Val Ser Glu Met
            515                 520                 525
Glu Met Met Lys Met Ile Gly Lys His Lys Asn Ile Ile Asn Leu Leu
            530                 535                 540
Gly Ala Cys Thr Gln Gly Gly Pro Leu Tyr Val Leu Val Glu Tyr Ala
545                 550                 555                 560
Ala Lys Gly Asn Leu Arg Glu Phe Leu Arg Ala Arg Arg Pro Pro Gly
                565                 570                 575
Leu Asp Tyr Ser Phe Asp Thr Cys Lys Pro Pro Glu Glu Gln Leu Thr
                580                 585                 590
Phe Lys Asp Leu Val Ser Cys Ala Tyr Gln Val Ala Arg Gly Met Glu
            595                 600                 605
Tyr Leu Ala Ser Gln Lys Cys Ile His Arg Asp Leu Ala Ala Arg Asn
            610                 615                 620
Val Leu Val Thr Glu Asp Asn Val Met Lys Ile Ala Asp Phe Gly Leu
625                 630                 635                 640
Ala Arg Asp Val His Asn Leu Asp Tyr Tyr Lys Lys Thr Thr Asn Gly
                645                 650                 655
Arg Leu Pro Val Lys Trp Met Ala Pro Glu Ala Leu Phe Asp Arg Val
                660                 665                 670
Tyr Thr His Gln Ser Asp Val Trp Ser Phe Gly Val Leu Leu Trp Glu
            675                 680                 685
Ile Phe Thr Leu Gly Gly Ser Pro Tyr Pro Gly Ile Pro Val Glu Glu
            690                 695                 700
Leu Phe Lys Leu Leu Lys Glu Gly His Arg Met Asp Lys Pro Ala Asn
705                 710                 715                 720
Cys Thr His Asp Leu Tyr Met Ile Met Arg Glu Cys Trp His Ala Ala
                725                 730                 735
Pro Ser Gln Arg Pro Thr Phe Lys Gln Leu Val Glu Asp Leu Asp Arg
                740                 745                 750
Val Leu Thr Val Thr Ser Thr Asp Glu Tyr Leu Asp Leu Ser Ala Pro
            755                 760                 765
Phe Glu Gln Tyr Ser Pro Gly Gln Asp Thr Pro Ser Ser Ser Ser
            770                 775                 780
Ser Gly Asp Asp Ser Val Phe Ala His Asp Leu Leu Pro Pro Ala Pro
785                 790                 795                 800
Pro Ser Ser Gly Gly Ser Arg Thr
                805
```

<210> SEQ ID NO 3
<211> LENGTH: 2421
<212> TYPE: DNA
<213> ORGANISM: Homo sapiens

<400> SEQUENCE: 3

| | | | | | |
|---|---|---|---|---|---|
| atgggcgccc | ctgcctgcgc | cctcgcgctc | tgcgtggccg | tggccatcgt | ggccggcgcc | 60 |
| tcctcggagt | ccttggggac | ggagcagcgc | gtcgtgggc | gagcggcaga | agtcccgggc | 120 |
| ccagagcccg | gccagcagga | gcagttggtc | ttcggcagcg | gggatgctgt | ggagctgagc | 180 |
| tgtccccgc | ccggggtgg | tcccatgggg | cccactgtct | gggtcaagga | tggcacaggg | 240 |
| ctggtgccct | cggagcgtgt | cctggtgggg | ccccagcggc | tgcaggtgct | gaatgcctcc | 300 |
| cacgaggact | ccggggccta | cagctgccgg | cagcggctca | cgcagcgcgt | actgtgccac | 360 |
| ttcagtgtgc | gggtgacaga | cgctccatcc | tcgggagatg | acgaagacgg | ggaggacgag | 420 |
| gctgaggaca | caggtgtgga | cacaggggcc | ccttactgga | cacggcccga | gcggatggac | 480 |
| aagaagctgc | tggccgtgcc | ggccgccaac | accgtccgct | tccgctgccc | agccgctggc | 540 |
| aaccccactc | cctccatctc | ctggctgaag | aacggcaggg | agttccgcgg | cgagcaccgc | 600 |
| attggaggca | tcaagctgcg | gcatcagcag | tggagcctgg | tcatggaaag | cgtggtgccc | 660 |
| tcggaccgcg | gcaactacac | ctgcgtcgtg | gagaacaagt | tggcagcat | ccggcagacg | 720 |
| tacacgctgg | acgtgctgga | gcgctccccg | caccggccca | tcctgcaggc | ggggctgccg | 780 |
| gccaaccaga | cggcggtgct | gggcagcgac | gtggagttcc | actgcaaggt | gtacagtgac | 840 |
| gcacagcccc | acatccagtg | gctcaagcac | gtggaggtga | acggcagcaa | ggtgggcccg | 900 |
| gacggcacac | cctacgttac | cgtgctcaag | acggcgggcg | ctaacaccac | cgacaaggag | 960 |
| ctagaggttc | tctccttgca | caacgtcacc | tttgaggacg | ccggggagta | cacctgcctg | 1020 |
| gcgggcaatt | ctattgggtt | ttctcatcac | tctgcgtggc | tggtggtgct | gccagccgag | 1080 |
| gaggagctgg | tggaggctga | cgaggcgggc | agtgtgtatg | caggcatcct | cagctacggg | 1140 |
| gtgggcttct | tcctgttcat | cctggtggtg | gcggctgtga | cgctctgccg | cctgcgcagc | 1200 |
| cccccaaga | aaggcctggg | ctcccccacc | gtgcacaaga | tctcccgctt | cccgctcaag | 1260 |
| cgacaggtgt | ccctggagtc | caacgcgtcc | atgagctcca | acacaccact | ggtgcgcatc | 1320 |
| gcaaggctgt | cctcagggga | gggccccacg | ctggccaatg | tctccgagct | cgagctgcct | 1380 |
| gccgacccca | aatgggagct | gtctcgggcc | cggctgaccc | tgggcaagcc | ccttggggag | 1440 |
| ggctgcttcg | gccaggtggt | catggcggag | gccatcggca | ttgacaagga | ccgggccgcc | 1500 |
| aagcctgtca | ccgtagccgt | gaagatgctg | aaagacgatg | ccactgacaa | ggacctgtcg | 1560 |
| gacctggtgt | ctgagatgga | gatgatgaag | atgatcggga | acacaaaaaa | catcatcaac | 1620 |
| ctgctgggcg | cctgcacgca | gggcgggccc | ctgtacgtgc | tggtggagta | cgcggccaag | 1680 |
| ggtaacctgc | gggagtttct | gcgggcgcgg | cggccccgg | gcctggacta | ctccttcgac | 1740 |
| acctgcaagc | cgcccgagga | gcagctcacc | ttcaaggacc | tggtgtcctg | tgcctaccag | 1800 |
| gtggcccggg | gcatggagta | cttggcctcc | cagaagtgca | tccacaggga | cctggctgcc | 1860 |
| cgcaatgtgc | tggtgaccga | ggacaacgtg | atgaagatcg | cagacttcgg | gctggcccgg | 1920 |
| gacgtgcaca | acctcgacta | ctacaagaag | acaaccaacg | gccggctgcc | cgtgaagtgg | 1980 |
| atggcgcctg | aggccttgtt | tgaccgagtc | tacactcacc | agagtgacgt | ctggtccttt | 2040 |
| ggggtcctgc | tctgggagat | cttcacgctg | gggggctccc | cgtacccgg | catccctgtg | 2100 |
| gaggagctct | tcaagctgct | gaaggagggc | caccgcatgg | acaagcccgc | caactgcaca | 2160 |

```
cacgacctgt acatgatcat gcgggagtgc tggcatgccg cgccctccca gaggcccacc    2220
ttcaagcagc tggtggagga cctggaccgt gtccttaccg tgacgtccac cgacgagtac    2280
ctggacctgt cggcgccttt cgagcagtac tccccgggtg ccaggacac ccccagctcc     2340 agctcctcag gggacgactc cgtgtttgcc cacgacctgc tgcccccggc cccacccagc    2400
agtgggggct cgcggacgtg a                                              2421
```

<210> SEQ ID NO 4
<211> LENGTH: 806
<212> TYPE: PRT
<213> ORGANISM: Homo sapiens

<400> SEQUENCE: 4

```
Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
                20                  25                  30

Gly Arg Ala Ala Glu Val Pro Gly Pro Glu Pro Gly Gln Gln Glu Gln
            35                  40                  45

Leu Val Phe Gly Ser Gly Asp Ala Val Glu Leu Ser Cys Pro Pro Pro
        50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300

Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
```

-continued

```
                325                 330                 335
Tyr Thr Cys Leu Ala Gly Asn Ser Ile Gly Phe Ser His His Ser Ala
            340                 345                 350
Trp Leu Val Val Leu Pro Ala Glu Glu Leu Val Glu Ala Asp Glu
        355                 360                 365
Ala Gly Ser Val Tyr Ala Gly Ile Leu Ser Tyr Gly Val Gly Phe Phe
    370                 375                 380
Leu Phe Ile Leu Val Val Ala Ala Val Thr Leu Cys Arg Leu Arg Ser
385                 390                 395                 400
Pro Pro Lys Lys Gly Leu Gly Ser Pro Thr Val His Lys Ile Ser Arg
                405                 410                 415
Phe Pro Leu Lys Arg Gln Val Ser Leu Glu Ser Asn Ala Ser Met Ser
            420                 425                 430
Ser Asn Thr Pro Leu Val Arg Ile Ala Arg Leu Ser Ser Gly Glu Gly
        435                 440                 445
Pro Thr Leu Ala Asn Val Ser Glu Leu Glu Leu Pro Ala Asp Pro Lys
    450                 455                 460
Trp Glu Leu Ser Arg Ala Arg Leu Thr Leu Gly Lys Pro Leu Gly Glu
465                 470                 475                 480
Gly Cys Phe Gly Gln Val Val Met Ala Glu Ala Ile Gly Ile Asp Lys
                485                 490                 495
Asp Arg Ala Ala Lys Pro Val Thr Val Ala Val Lys Met Leu Lys Asp
            500                 505                 510
Asp Ala Thr Asp Lys Asp Leu Ser Asp Leu Val Ser Glu Met Glu Met
        515                 520                 525
Met Lys Met Ile Gly Lys His Lys Asn Ile Ile Asn Leu Leu Gly Ala
    530                 535                 540
Cys Thr Gln Gly Gly Pro Leu Tyr Val Leu Val Glu Tyr Ala Ala Lys
545                 550                 555                 560
Gly Asn Leu Arg Glu Phe Leu Arg Ala Arg Arg Pro Pro Gly Leu Asp
                565                 570                 575
Tyr Ser Phe Asp Thr Cys Lys Pro Pro Glu Glu Gln Leu Thr Phe Lys
            580                 585                 590
Asp Leu Val Ser Cys Ala Tyr Gln Val Ala Arg Gly Met Glu Tyr Leu
        595                 600                 605
Ala Ser Gln Lys Cys Ile His Arg Asp Leu Ala Ala Arg Asn Val Leu
    610                 615                 620
Val Thr Glu Asp Asn Val Met Lys Ile Ala Asp Phe Gly Leu Ala Arg
625                 630                 635                 640
Asp Val His Asn Leu Asp Tyr Tyr Lys Lys Thr Thr Asn Gly Arg Leu
                645                 650                 655
Pro Val Lys Trp Met Ala Pro Glu Ala Leu Phe Asp Arg Val Tyr Thr
            660                 665                 670
His Gln Ser Asp Val Trp Ser Phe Gly Val Leu Leu Trp Glu Ile Phe
        675                 680                 685
Thr Leu Gly Gly Ser Pro Tyr Pro Gly Ile Pro Val Glu Glu Leu Phe
    690                 695                 700
Lys Leu Leu Lys Glu Gly His Arg Met Asp Lys Pro Ala Asn Cys Thr
705                 710                 715                 720
His Asp Leu Tyr Met Ile Met Arg Glu Cys Trp His Ala Ala Pro Ser
                725                 730                 735
Gln Arg Pro Thr Phe Lys Gln Leu Val Glu Asp Leu Asp Arg Val Leu
            740                 745                 750
```

-continued

```
Thr Val Thr Ser Thr Asp Glu Tyr Leu Asp Leu Ser Ala Pro Phe Glu
        755                 760                 765
Gln Tyr Ser Pro Gly Gly Gln Asp Thr Pro Ser Ser Ser Ser Gly
        770                 775                 780
Asp Asp Ser Val Phe Ala His Asp Leu Leu Pro Pro Ala Pro Pro Ser
785                 790                 795                 800
Ser Gly Gly Ser Arg Thr
            805

<210> SEQ ID NO 5
<211> LENGTH: 2085
<212> TYPE: DNA
<213> ORGANISM: Homo sapiens

<400> SEQUENCE: 5
atgggcgccc ctgcctgcgc cctcgcgctc tgcgtggccg tggccatcgt ggccggcgcc      60
tcctcggagt ccttggggac ggagcagcgc gtcgtggggc gagcggcaga agtcccgggc     120
ccagagcccg ccagcagga gcagttggtc ttcggcagcg gggatgctgt ggagctgagc     180
tgtcccccgc ccggggtgg tcccatgggg cccactgtct gggtcaagga tggcacaggg     240
ctggtgccct cggagcgtgt cctggtgggg cccagcggc tgcaggtgct gaatgcctcc     300
cacgaggact ccggggccta cagctgccgg cagcggctca cgcagcgcgt actgtgccac     360
ttcagtgtgc gggtgacaga cgctccatcc tcgggagatg acgaagacgg ggaggacgag     420
gctgaggaca caggtgtgga cacaggggcc ccttactgga cacggcccga gcggatggac     480
aagaagctgc tggccgtgcc ggccgccaac accgtccgct tccgctgccc agccgctggc     540
aaccccactc cctccatctc ctggctgaag aacggcaggg agttccgcgg cgagcaccgc     600
attggaggca tcaagctgcg gcatcagcag tggagcctgg tcatggaaag cgtggtgccc     660
tcggaccgcg gcaactacac ctgcgtcgtg gagaacaagt tggcagcat ccggcagacg     720 tacacgctgg acgtgctgga gcgctccccg caccggccca tcctgcaggc ggggctgccg     780
gccaaccaga cggcggtgct gggcagcgac gtggagttcc actgcaaggt gtacagtgac     840
gcacagcccc acatccagtg gctcaagcac gtggaggtga acggcagcaa ggtgggcccg     900
gacggcacac cctacgttac cgtgctcaag gtgtccctgg agtccaacgc gtccatgagc     960
tccaacacac cactggtgcg catcgcaagg ctgtcctcag ggagggccc cacgctggcc    1020 aatgtctccg agctcgagct gcctgccgac cccaaatggg agctgtctcg ggcccggctg    1080
accctgggca gcccttgg ggagggctgc ttcggccagg tggtcatggc ggaggccatc    1140
ggcattgaca ggaccgggc cgccaagcct gtcaccgtag ccgtgaagat gctgaaagac    1200
gatgccactg acaaggacct gtcggacctg gtgtctgaga tggagatgat gaagatgatc    1260
gggaaacaca aaacatcat caacctgctg ggcgcctgca cgcagggcgg gcccctgtac    1320
gtgctggtgg agtacgcggc caagggtaac ctgcgggagt ttctgcgggc gcggcggccc    1380
ccgggcctgg actactcctt cgacacctgc aagccgcccg aggagcagct caccttcaag    1440
gacctggtgt cctgtgccta ccaggtggcc cggggcatgg agtacttggc ctcccagaag    1500
tgcatccaca gggacctggc tgcccgcaat gtgctggtga ccgaggacaa cgtgatgaag    1560
atcgcagact cgggctggc ccgggacgtg cacaacctcg actactacaa gaagacaacc    1620
aacggccggc tgcccgtgaa gtggatggcg cctgaggcct tgtttgaccg agtctacact    1680
caccagagtg acgtctggtc ctttggggtc ctgctctggg agatcttcac gctgggggc    1740
```

```
tccccgtacc ccggcatccc tgtggaggag ctcttcaagc tgctgaagga gggccaccgc   1800
atggacaagc ccgccaactg cacacacgac ctgtacatga tcatgcggga gtgctggcat   1860
gccgcgccct cccagaggcc caccttcaag cagctggtgg aggacctgga ccgtgtcctt   1920
accgtgacgt ccaccgacga gtacctggac ctgtcggcgc ctttcgagca gtactccccg   1980
ggtggccagg acaccccag ctccagctcc tcagggacg actccgtgtt tgcccacgac    2040
ctgctgcccc cggccccacc cagcagtggg ggctcgcgga cgtga                   2085
```

```
<210> SEQ ID NO 6
<211> LENGTH: 694
<212> TYPE: PRT
<213> ORGANISM: Homo sapiens

<400> SEQUENCE: 6
```

| | | | | | | | | | | | | | | |
|---|---|---|---|---|---|---|---|---|---|---|---|---|---|---|
| Met | Gly | Ala | Pro | Ala | Cys | Ala | Leu | Ala | Leu | Cys | Val | Ala | Val | Ala | Ile |
| 1 | | | | 5 | | | | | 10 | | | | | 15 | |
| Val | Ala | Gly | Ala | Ser | Ser | Glu | Ser | Leu | Gly | Thr | Glu | Gln | Arg | Val | Val |
| | | | | 20 | | | | | 25 | | | | | 30 | |
| Gly | Arg | Ala | Ala | Glu | Val | Pro | Gly | Pro | Glu | Pro | Gly | Gln | Gln | Glu | Gln |
| | | | 35 | | | | | 40 | | | | | 45 | | |
| Leu | Val | Phe | Gly | Ser | Gly | Asp | Ala | Val | Glu | Leu | Ser | Cys | Pro | Pro | Pro |
| | | 50 | | | | | 55 | | | | | 60 | | | |
| Gly | Gly | Gly | Pro | Met | Gly | Pro | Thr | Val | Trp | Val | Lys | Asp | Gly | Thr | Gly |
| 65 | | | | | 70 | | | | | 75 | | | | | 80 |
| Leu | Val | Pro | Ser | Glu | Arg | Val | Leu | Val | Gly | Pro | Gln | Arg | Leu | Gln | Val |
| | | | | 85 | | | | | 90 | | | | | 95 | |
| Leu | Asn | Ala | Ser | His | Glu | Asp | Ser | Gly | Ala | Tyr | Ser | Cys | Arg | Gln | Arg |
| | | | | 100 | | | | | 105 | | | | | 110 | |
| Leu | Thr | Gln | Arg | Val | Leu | Cys | His | Phe | Ser | Val | Arg | Val | Thr | Asp | Ala |
| | | | 115 | | | | | 120 | | | | | 125 | | |
| Pro | Ser | Ser | Gly | Asp | Asp | Glu | Asp | Gly | Glu | Asp | Glu | Ala | Glu | Asp | Thr |
| | | 130 | | | | | 135 | | | | | 140 | | | |
| Gly | Val | Asp | Thr | Gly | Ala | Pro | Tyr | Trp | Thr | Arg | Pro | Glu | Arg | Met | Asp |
| 145 | | | | | 150 | | | | | 155 | | | | | 160 |
| Lys | Lys | Leu | Leu | Ala | Val | Pro | Ala | Ala | Asn | Thr | Val | Arg | Phe | Arg | Cys |
| | | | | 165 | | | | | 170 | | | | | 175 | |
| Pro | Ala | Ala | Gly | Asn | Pro | Thr | Pro | Ser | Ile | Ser | Trp | Leu | Lys | Asn | Gly |
| | | | | 180 | | | | | 185 | | | | | 190 | |
| Arg | Glu | Phe | Arg | Gly | Glu | His | Arg | Ile | Gly | Gly | Ile | Lys | Leu | Arg | His |
| | | | 195 | | | | | 200 | | | | | 205 | | |
| Gln | Gln | Trp | Ser | Leu | Val | Met | Glu | Ser | Val | Val | Pro | Ser | Asp | Arg | Gly |
| | | | 210 | | | | | 215 | | | | | 220 | | |
| Asn | Tyr | Thr | Cys | Val | Val | Glu | Asn | Lys | Phe | Gly | Ser | Ile | Arg | Gln | Thr |
| 225 | | | | | 230 | | | | | 235 | | | | | 240 |
| Tyr | Thr | Leu | Asp | Val | Leu | Glu | Arg | Ser | Pro | His | Arg | Pro | Ile | Leu | Gln |
| | | | | 245 | | | | | 250 | | | | | 255 | |
| Ala | Gly | Leu | Pro | Ala | Asn | Gln | Thr | Ala | Val | Leu | Gly | Ser | Asp | Val | Glu |
| | | | | 260 | | | | | 265 | | | | | 270 | |
| Phe | His | Cys | Lys | Val | Tyr | Ser | Asp | Ala | Gln | Pro | His | Ile | Gln | Trp | Leu |
| | | | 275 | | | | | 280 | | | | | 285 | | |
| Lys | His | Val | Glu | Val | Asn | Gly | Ser | Lys | Val | Gly | Pro | Asp | Gly | Thr | Pro |
| | | | 290 | | | | | 295 | | | | | 300 | | |
| Tyr | Val | Thr | Val | Leu | Lys | Val | Ser | Leu | Glu | Ser | Asn | Ala | Ser | Met | Ser |
| 305 | | | | | 310 | | | | | 315 | | | | | 320 |

```
Ser Asn Thr Pro Leu Val Arg Ile Ala Arg Leu Ser Ser Gly Glu Gly
            325                 330                 335

Pro Thr Leu Ala Asn Val Ser Glu Leu Glu Leu Pro Ala Asp Pro Lys
            340                 345                 350

Trp Glu Leu Ser Arg Ala Arg Leu Thr Leu Gly Lys Pro Leu Gly Glu
            355                 360                 365

Gly Cys Phe Gly Gln Val Met Ala Glu Ala Ile Gly Ile Asp Lys
            370                 375                 380

Asp Arg Ala Ala Lys Pro Val Thr Val Ala Val Lys Met Leu Lys Asp
385                 390                 395                 400

Asp Ala Thr Asp Lys Asp Leu Ser Asp Leu Val Ser Glu Met Glu Met
                    405                 410                 415

Met Lys Met Ile Gly Lys His Lys Asn Ile Ile Asn Leu Leu Gly Ala
                    420                 425                 430

Cys Thr Gln Gly Gly Pro Leu Tyr Val Leu Val Glu Tyr Ala Ala Lys
            435                 440                 445

Gly Asn Leu Arg Glu Phe Leu Arg Ala Arg Arg Pro Pro Gly Leu Asp
            450                 455                 460

Tyr Ser Phe Asp Thr Cys Lys Pro Pro Glu Glu Gln Leu Thr Phe Lys
465                 470                 475                 480

Asp Leu Val Ser Cys Ala Tyr Gln Val Ala Arg Gly Met Glu Tyr Leu
                    485                 490                 495

Ala Ser Gln Lys Cys Ile His Arg Asp Leu Ala Ala Arg Asn Val Leu
            500                 505                 510

Val Thr Glu Asp Asn Val Met Lys Ile Ala Asp Phe Gly Leu Ala Arg
            515                 520                 525

Asp Val His Asn Leu Asp Tyr Tyr Lys Lys Thr Thr Asn Gly Arg Leu
            530                 535                 540

Pro Val Lys Trp Met Ala Pro Glu Ala Leu Phe Asp Arg Val Tyr Thr
545                 550                 555                 560

His Gln Ser Asp Val Trp Ser Phe Gly Val Leu Leu Trp Glu Ile Phe
                    565                 570                 575

Thr Leu Gly Gly Ser Pro Tyr Pro Gly Ile Pro Val Glu Glu Leu Phe
                    580                 585                 590

Lys Leu Leu Lys Glu Gly His Arg Met Asp Lys Pro Ala Asn Cys Thr
            595                 600                 605

His Asp Leu Tyr Met Ile Met Arg Glu Cys Trp His Ala Ala Pro Ser
            610                 615                 620

Gln Arg Pro Thr Phe Lys Gln Leu Val Glu Asp Leu Asp Arg Val Leu
625                 630                 635                 640

Thr Val Thr Ser Thr Asp Glu Tyr Leu Asp Leu Ser Ala Pro Phe Glu
                    645                 650                 655

Gln Tyr Ser Pro Gly Gly Gln Asp Thr Pro Ser Ser Ser Ser Ser Gly
                    660                 665                 670

Asp Asp Ser Val Phe Ala His Asp Leu Leu Pro Pro Ala Pro Pro Ser
            675                 680                 685

Ser Gly Gly Ser Arg Thr
690

<210> SEQ ID NO 7
<211> LENGTH: 2409
<212> TYPE: DNA
<213> ORGANISM: Bos taurus
```

<400> SEQUENCE: 7

```
atgggcgccc cggctcgcgc cctcgcgttt tgcgtggcag tggcggtcat gaccggcgcc      60
gccctcgggt ccccgggcgt ggagccccgc gtcgcgcgga gagcggcaga ggtcccgggc     120
cccgagccca gcccgcagga gcgggccttt ggcagcgggg acaccgtgga gctgagctgc     180
cgcttgccgg cggggtgcc cacagagccc accgtctggg tgaaggacgg cgtgggcctg     240
gcgccctcgg accgcgtcct ggtggggccg cagcggctac aggtgctcaa cgcctcccac     300
gaggacgccg gagcctacag ctgccgccag cgcctctccc agcggctgct gtgcctcttc     360
agcgtgcgcg tgacagatgc tccgtcctca ggggatgacg agggtgggga cgacgaggcc     420
gaggacacag ctggggcccc ttactggacg cggcctgagc ggatggacaa gaagctgcta     480
gcggtgccgg ccgccaacac ggttcgcttc cgctgcccag ctgctggcaa ccccacgcca     540
tccatcacct ggctgaagaa cggcaaggag ttccggggcg agcaccgcat cgggggaatc     600
aaactgcggc agcagcagtg gagcctggtc atggagagcg tggtgccctc ggaccgcggc     660
aactacacgt gcgtcgtgga gaacaagttc ggcagaatcc agcagaccta caccctggac     720
gtgctggagc gctctccgca ccggcccatc ctacaggccg gctgcccgc taaccagaca     780
gccgtgctgg cagcgatgt ggagttccac tgcaaggtct acagcgacgc ccagccccac     840
atccagtggc tcaagcacgt ggaggtgaac ggcagcaagg tggggcccga cggcacgccc     900
tacgtcaccg tgctcaagac ggcgggcgct aacaccaccg acaaggagct agaggttcta     960
tccttgcgca atgtcacctt tgaggacgcg ggggagtaca catgtctggc gggcaattct    1020
atcgggtttt cccatcactc tgcgtggctg gtggtgctgc cagctgagga ggagctggtg    1080
gaagccggtg aggctggcgg tgtgttcgcg ggtgtcctca gctacgggct gggcttcctc    1140
ctcttcatcc tggccgtggc cgccgttacg ctctaccgcc tgaggagccc ccctaagaag    1200
ggcctgggct cgcccgcggt gcacaaggtc tcccgcttcc cgctcaagcg acaggtgtcc    1260
ttggagtcca gctcatccat gagctccaac acaccgctgg tacgcattgc ccggctgtca    1320
tcgggcgagg gccccaccct ggccaacgtc tctgagctcg agctgccgc cgaccccaag    1380
tgggagctgt cccgggcccg gctgaccctg ggcaagcctc ttggggaggg ctgcttcggc    1440
caggtggtca tggcagaggc cattggcatc gacaaggacc gagctgccaa gcctgtcacg    1500
gtggccgtga agatgctgaa agatgacgcc acggataagg acttatcgga cctggtgtcc    1560
gagatggaga tgatgaagat gatcggaaaa cacaagaaca ttatcaacct gctaggcgcc    1620
tgcacgcagg gcgggcccct gtacgtgctg gtggagtacg cggccaaggg caacctgcgg    1680
gaatacctgc gggcacggcg gccccgggc actgactact ccttcgacac ctgccggctg    1740
cccgaggagc agctcacctt caaagacctg gtgtcctgcg cctaccaggt ggcgcggggc    1800
atggagtacc tggcctcgca gaagtgcatc cacagggacc tggcggcccg caacgtgctg    1860
gtgactgagg acaacgtgat gaaaatcgcc gacttcggcc tggctcgtga cgtgcacaac    1920
ctcgactact acaaaaagac cacaaacggc cgcctgcccg tgaagtggat ggcacccgag    1980
gccttgtttg accgcgtcta cacccaccaa agtgacgtct ggtccttcgg ggtcctgctc    2040
tgggagatct tcacgctggg gggctcgccg tacccggca tccccgtgga ggagctcttc    2100
aagctgctga ggaaggcca ccgcatggac aagccggcca actgcacgca tgacctgtac    2160
atgatcatgc gcgagtgctg gcacgccgcg ccctcgcaga ggcccacctt caagcagctg    2220
gtggaggacc tggaccgtgt gctcaccgtg acgtccaccg acgagtacct ggacctgtcg    2280
gtgcccttcg agcagtactc gccgggcggc caggacaccc ccagctccgg ctcctcgggg    2340
```

```
gacgactccg tgttcgctca cgacctgctg cccccggccc catccggcag cggaggctcg    2400
cggacgtga                                                             2409
```

<210> SEQ ID NO 8
<211> LENGTH: 802
<212> TYPE: PRT
<213> ORGANISM: Bos taurus

<400> SEQUENCE: 8

```
Met Gly Ala Pro Ala Arg Ala Leu Ala Phe Cys Val Ala Val Ala Val
1               5                   10                  15

Met Thr Gly Ala Ala Leu Gly Ser Pro Gly Val Glu Pro Arg Val Ala
            20                  25                  30

Arg Arg Ala Ala Glu Val Pro Gly Pro Glu Pro Ser Pro Gln Glu Arg
        35                  40                  45

Ala Phe Gly Ser Gly Asp Thr Val Glu Leu Ser Cys Arg Leu Pro Ala
    50                  55                  60

Gly Val Pro Thr Glu Pro Thr Val Trp Val Lys Asp Gly Val Gly Leu
65                  70                  75                  80

Ala Pro Ser Asp Arg Val Leu Val Gly Pro Gln Arg Leu Gln Val Leu
                85                  90                  95

Asn Ala Ser His Glu Asp Ala Gly Ala Tyr Ser Cys Arg Gln Arg Leu
            100                 105                 110

Ser Gln Arg Leu Leu Cys Leu Phe Ser Val Arg Val Thr Asp Ala Pro
        115                 120                 125

Ser Ser Gly Asp Asp Glu Gly Gly Asp Asp Glu Ala Glu Asp Thr Ala
    130                 135                 140

Gly Ala Pro Tyr Trp Thr Arg Pro Glu Arg Met Asp Lys Lys Leu Leu
145                 150                 155                 160

Ala Val Pro Ala Ala Asn Thr Val Arg Phe Arg Cys Pro Ala Ala Gly
                165                 170                 175

Asn Pro Thr Pro Ser Ile Thr Trp Leu Lys Asn Gly Lys Glu Phe Arg
            180                 185                 190

Gly Glu His Arg Ile Gly Gly Ile Lys Leu Arg Gln Gln Gln Trp Ser
        195                 200                 205

Leu Val Met Glu Ser Val Val Pro Ser Asp Arg Gly Asn Tyr Thr Cys
    210                 215                 220

Val Val Glu Asn Lys Phe Gly Arg Ile Gln Gln Thr Tyr Thr Leu Asp
225                 230                 235                 240

Val Leu Glu Arg Ser Pro His Arg Pro Ile Leu Gln Ala Gly Leu Pro
                245                 250                 255

Ala Asn Gln Thr Ala Val Leu Gly Ser Asp Val Glu Phe His Cys Lys
            260                 265                 270

Val Tyr Ser Asp Ala Gln Pro His Ile Gln Trp Leu Lys His Val Glu
        275                 280                 285

Val Asn Gly Ser Lys Val Gly Pro Asp Gly Thr Pro Tyr Val Thr Val
    290                 295                 300

Leu Lys Thr Ala Gly Ala Asn Thr Thr Asp Lys Glu Leu Glu Val Leu
305                 310                 315                 320

Ser Leu Arg Asn Val Thr Phe Glu Asp Ala Gly Glu Tyr Thr Cys Leu
                325                 330                 335

Ala Gly Asn Ser Ile Gly Phe Ser His His Ser Ala Trp Leu Val Val
            340                 345                 350
```

```
Leu Pro Ala Glu Glu Leu Val Glu Ala Gly Glu Ala Gly Gly Val
        355                 360                 365
Phe Ala Gly Val Leu Ser Tyr Gly Leu Gly Phe Leu Leu Phe Ile Leu
    370                 375                 380
Ala Val Ala Ala Val Thr Leu Tyr Arg Leu Arg Ser Pro Pro Lys Lys
385                 390                 395                 400
Gly Leu Gly Ser Pro Ala Val His Lys Val Ser Arg Phe Pro Leu Lys
                405                 410                 415
Arg Gln Val Ser Leu Glu Ser Ser Ser Met Ser Ser Asn Thr Pro
                420                 425                 430
Leu Val Arg Ile Ala Arg Leu Ser Ser Gly Glu Gly Pro Thr Leu Ala
            435                 440                 445
Asn Val Ser Glu Leu Glu Leu Pro Ala Asp Pro Lys Trp Glu Leu Ser
        450                 455                 460
Arg Ala Arg Leu Thr Leu Gly Lys Pro Leu Gly Glu Gly Cys Phe Gly
465                 470                 475                 480
Gln Val Val Met Ala Glu Ala Ile Gly Ile Asp Lys Asp Arg Ala Ala
                485                 490                 495
Lys Pro Val Thr Val Ala Val Lys Met Leu Lys Asp Asp Ala Thr Asp
                500                 505                 510
Lys Asp Leu Ser Asp Leu Val Ser Glu Met Glu Met Met Lys Met Ile
            515                 520                 525
Gly Lys His Lys Asn Ile Ile Asn Leu Leu Gly Ala Cys Thr Gln Gly
        530                 535                 540
Gly Pro Leu Tyr Val Leu Val Glu Tyr Ala Ala Lys Gly Asn Leu Arg
545                 550                 555                 560
Glu Tyr Leu Arg Ala Arg Arg Pro Pro Gly Thr Asp Tyr Ser Phe Asp
                565                 570                 575
Thr Cys Arg Leu Pro Glu Glu Gln Leu Thr Phe Lys Asp Leu Val Ser
            580                 585                 590
Cys Ala Tyr Gln Val Ala Arg Gly Met Glu Tyr Leu Ala Ser Gln Lys
        595                 600                 605
Cys Ile His Arg Asp Leu Ala Ala Arg Asn Val Leu Val Thr Glu Asp
    610                 615                 620
Asn Val Met Lys Ile Ala Asp Phe Gly Leu Ala Arg Asp Val His Asn
625                 630                 635                 640
Leu Asp Tyr Tyr Lys Lys Thr Thr Asn Gly Arg Leu Pro Val Lys Trp
                645                 650                 655
Met Ala Pro Glu Ala Leu Phe Asp Arg Val Tyr Thr His Gln Ser Asp
            660                 665                 670
Val Trp Ser Phe Gly Val Leu Leu Trp Glu Ile Phe Thr Leu Gly Gly
        675                 680                 685
Ser Pro Tyr Pro Gly Ile Pro Val Glu Glu Leu Phe Lys Leu Leu Lys
    690                 695                 700
Glu Gly His Arg Met Asp Lys Pro Ala Asn Cys Thr His Asp Leu Tyr
705                 710                 715                 720
Met Ile Met Arg Glu Cys Trp His Ala Ala Pro Ser Gln Arg Pro Thr
                725                 730                 735
Phe Lys Gln Leu Val Glu Asp Leu Asp Arg Val Leu Thr Val Thr Ser
            740                 745                 750
Thr Asp Glu Tyr Leu Asp Leu Ser Val Pro Phe Glu Gln Tyr Ser Pro
        755                 760                 765
Gly Gly Gln Asp Thr Pro Ser Ser Gly Ser Ser Gly Asp Asp Ser Val
```

```
                770              775            780
Phe Ala His Asp Leu Leu Pro Pro Ala Pro Ser Gly Ser Gly Gly Ser
785             790             795             800
Arg Thr

<210> SEQ ID NO 9
<211> LENGTH: 2409
<212> TYPE: DNA
<213> ORGANISM: Mus musculus

<400> SEQUENCE: 9
atggtagtcc cggcctgcgt gctagtgttc tgcgtggcgg tcgtggctgg agctacttcc      60
gagcctcctg gtccagagca gcgagttgtg cggagagcgg cagaggttcc agggcctgaa     120
cctagccagc aggagcaggt ggccttcggc agtggggaca ccgtggagct gagctgccat     180
cctcctggag gtgccccac agggcccacg gtctgggcta aggatggtac aggtctggtg     240
gcctcccacc gcatcctggt ggggcctcag aggctgcaag tgctaaatgc ctcccacgaa     300
gatgcagggg tctacagctg ccagcaccgg ctcactcggc gtgtgctgtg ccacttcagt     360
gtgcgtgtaa cagatgctcc atcctcagga gatgacgaag atggggagga cgtggctgaa     420
gacacagggg ctccttattg gactcgcccg gagcgaatgg ataagaaact gctggctgtg     480
ccagccgcaa acactgtccg cttccgctgc ccagctgctg caacccta ccctccatc       540 tcctggctga gaatggcaa agaattccga ggggagcatc gcattggggg catcaagctc     600
cggcaccagc agtggagctt ggtcatggaa agtgtggtac cctccgatcg tgcaactat     660 acctgtgtag ttgagaacaa gtttggcagc atccggcaga catacacact ggatgtgctg     720
gagcgctccc cacaccggcc catcctgcag gctgggctgc cggccaacca gacagccatt     780
ctaggcagtg acgtggagtt ccactgcaag gtgtacagcg atgcacagcc acacatccag     840
tggctgaagc acgtggaagt gaacggcagc aaggtgggcc ctgacggcac gccctacgtc     900
actgtactca gtcctggat cagtgagaat gtggaggcag acgcacgcct ccgcctggcc     960
aatgtgtcgg agcgggacgg gggcgagtac ctctgtcgag ccaccaattt cataggcgtg    1020
gctgagaagg ccttttggct gcgtgttcac gggccccaag cagctgagga ggagctgatg    1080
gaaactgatg aggctggcag cgtgtacgca ggcgtcctca gctacggggt ggtcttcttc    1140
ctcttcatcc tggtggtggc agctgtgata tctctgccgc tgcgcagtcc cccaaagaag    1200
ggcttgggct cgcccaccgt gcacaaggtc tctcgcttcc cgcttaagcg acaggtgtcc    1260
ttggaatcta actcctctat gaactccaac acaccccttg tccggattgc ccggctgtcc    1320
tcaggagaag gtcctgttct ggccaatgtt tctgaacttg agctgcctgc tgaccccaag    1380
tgggagctat ccaggacccg gctgacactt ggtaagcctc ttggagaagg ctgctttgga    1440
caggtggtca tggcagaagc tattggcatc gacaaggacc gtactgccaa gcctgtcacc    1500
gtggccgtga agatgctgaa agatgatgcg actgacaagg acctgtcgga cctggtatct    1560
gagatggaga tgatgaaat gattggcaag cacaagaaca tcattaacct gctggggggcg    1620 tgcacacagg gtgggcccct gtatgtgctg gtggagtacg cagccaaggg caatctccgg    1680
gagttccttc gggcgcggcg gcctccaggc atggactact cctttgatgc ctgcaggctg    1740
ccagaggaac agctcacctg caaggatcta gtgtcctgtg cctaccaggt ggcacggggc    1800
atggaatact ggcttctca gaagtgtatt cacagagact ggctgccag aaacgtcctg    1860 gtgaccgagg acaatgtgat gaagattgcg gactttggcc tggctcgaga tgtgcacaac    1920
```

-continued

```
ctggactact acaagaagac cacaaatggc cggctacctg tgaagtggat ggcaccagag    1980 gcccttttg accgagtcta cacccaccag agtgatgttt ggtctttttgg tgtcctcctc    2040 tgggagatct ttacgctggg gggctcaccg tatcctggca tcccagtgga agagcttttc    2100
aagctgttga aagagggcca ccgcatggac aagccagcca gctgcacaca tgacctgtac    2160
atgatcatgc gggaatgttg gcatgcggtg ccttcacaga ggcccacctt caagcagttg    2220
gtagaggatt tagaccgcat cctcactgtg acatcaaccg acgagtactt ggacctctcc    2280
gtgccgtttg agcagtactc gccaggtggc caggacacgc ctagctccag ctcgtccgga    2340
gatgactcgg tgttcaccca tgacctgcta ccccaggtc cacccagtaa cggggggacct    2400 cggacgtga                                                           2409
```

<210> SEQ ID NO 10
<211> LENGTH: 802
<212> TYPE: PRT
<213> ORGANISM: Mus musculus

<400> SEQUENCE: 10

```
Met Val Val Pro Ala Cys Val Leu Val Phe Cys Val Ala Val Val Ala
1               5                   10                  15

Gly Ala Thr Ser Glu Pro Pro Gly Pro Glu Gln Arg Val Val Arg Arg
            20                  25                  30

Ala Ala Glu Val Pro Gly Pro Glu Pro Ser Gln Gln Glu Gln Val Ala
        35                  40                  45

Phe Gly Ser Gly Asp Thr Val Glu Leu Ser Cys His Pro Pro Gly Gly
    50                  55                  60

Ala Pro Thr Gly Pro Thr Val Trp Ala Lys Asp Gly Thr Gly Leu Val
65                  70                  75                  80

Ala Ser His Arg Ile Leu Val Gly Pro Gln Arg Leu Gln Val Leu Asn
                85                  90                  95

Ala Ser His Glu Asp Ala Gly Val Tyr Ser Cys Gln His Arg Leu Thr
            100                 105                 110

Arg Arg Val Leu Cys His Phe Ser Val Arg Val Thr Asp Ala Pro Ser
        115                 120                 125

Ser Gly Asp Asp Glu Asp Gly Glu Asp Val Ala Glu Asp Thr Gly Ala
    130                 135                 140

Pro Tyr Trp Thr Arg Pro Glu Arg Met Asp Lys Lys Leu Leu Ala Val
145                 150                 155                 160

Pro Ala Ala Asn Thr Val Arg Phe Arg Cys Pro Ala Ala Gly Asn Pro
                165                 170                 175

Thr Pro Ser Ile Ser Trp Leu Lys Asn Gly Lys Glu Phe Arg Gly Glu
            180                 185                 190

His Arg Ile Gly Gly Ile Lys Leu Arg His Gln Gln Trp Ser Leu Val
        195                 200                 205

Met Glu Ser Val Val Pro Ser Asp Arg Gly Asn Tyr Thr Cys Val Val
    210                 215                 220

Glu Asn Lys Phe Gly Ser Ile Arg Gln Thr Tyr Thr Leu Asp Val Leu
225                 230                 235                 240

Glu Arg Ser Pro His Arg Pro Ile Leu Gln Ala Gly Leu Pro Ala Asn
                245                 250                 255

Gln Thr Ala Ile Leu Gly Ser Asp Val Glu Phe His Cys Lys Val Tyr
            260                 265                 270

Ser Asp Ala Gln Pro His Ile Gln Trp Leu Lys His Val Glu Val Asn
        275                 280                 285
```

```
Gly Ser Lys Val Gly Pro Asp Gly Thr Pro Tyr Val Thr Val Leu Lys
    290                 295                 300

Ser Trp Ile Ser Glu Asn Val Glu Ala Asp Ala Arg Leu Arg Leu Ala
305                 310                 315                 320

Asn Val Ser Glu Arg Asp Gly Gly Glu Tyr Leu Cys Arg Ala Thr Asn
                325                 330                 335

Phe Ile Gly Val Ala Glu Lys Ala Phe Trp Leu Arg Val His Gly Pro
            340                 345                 350

Gln Ala Ala Glu Glu Glu Leu Met Glu Thr Asp Glu Ala Gly Ser Val
        355                 360                 365

Tyr Ala Gly Val Leu Ser Tyr Gly Val Val Phe Phe Leu Phe Ile Leu
    370                 375                 380

Val Val Ala Ala Val Ile Leu Cys Arg Leu Arg Ser Pro Pro Lys Lys
385                 390                 395                 400

Gly Leu Gly Ser Pro Thr Val His Lys Val Ser Arg Phe Pro Leu Lys
                405                 410                 415

Arg Gln Val Ser Leu Glu Ser Asn Ser Ser Met Asn Ser Asn Thr Pro
            420                 425                 430

Leu Val Arg Ile Ala Arg Leu Ser Ser Gly Glu Gly Pro Val Leu Ala
        435                 440                 445

Asn Val Ser Glu Leu Glu Leu Pro Ala Asp Pro Lys Trp Glu Leu Ser
    450                 455                 460

Arg Thr Arg Leu Thr Leu Gly Lys Pro Leu Gly Glu Gly Cys Phe Gly
465                 470                 475                 480

Gln Val Val Met Ala Glu Ala Ile Gly Ile Asp Lys Asp Arg Thr Ala
                485                 490                 495

Lys Pro Val Thr Val Ala Val Lys Met Leu Lys Asp Asp Ala Thr Asp
            500                 505                 510

Lys Asp Leu Ser Asp Leu Val Ser Glu Met Glu Met Met Lys Met Ile
        515                 520                 525

Gly Lys His Lys Asn Ile Ile Asn Leu Leu Gly Ala Cys Thr Gln Gly
    530                 535                 540

Gly Pro Leu Tyr Val Leu Val Glu Tyr Ala Ala Lys Gly Asn Leu Arg
545                 550                 555                 560

Glu Phe Leu Arg Ala Arg Arg Pro Pro Gly Met Asp Tyr Ser Phe Asp
                565                 570                 575

Ala Cys Arg Leu Pro Glu Glu Gln Leu Thr Cys Lys Asp Leu Val Ser
            580                 585                 590

Cys Ala Tyr Gln Val Ala Arg Gly Met Glu Tyr Leu Ala Ser Gln Lys
        595                 600                 605

Cys Ile His Arg Asp Leu Ala Ala Arg Asn Val Leu Val Thr Glu Asp
    610                 615                 620

Asn Val Met Lys Ile Ala Asp Phe Gly Leu Ala Arg Asp Val His Asn
625                 630                 635                 640

Leu Asp Tyr Tyr Lys Lys Thr Thr Asn Gly Arg Leu Pro Val Lys Trp
                645                 650                 655

Met Ala Pro Glu Ala Leu Phe Asp Arg Val Tyr Thr His Gln Ser Asp
            660                 665                 670

Val Trp Ser Phe Gly Val Leu Leu Trp Glu Ile Phe Thr Leu Gly Gly
        675                 680                 685

Ser Pro Tyr Pro Gly Ile Pro Val Glu Glu Leu Phe Lys Leu Leu Lys
    690                 695                 700
```

-continued

```
Glu Gly His Arg Met Asp Lys Pro Ala Ser Cys Thr His Asp Leu Tyr
705                 710                 715                 720

Met Ile Met Arg Glu Cys Trp His Ala Val Pro Ser Gln Arg Pro Thr
            725                 730                 735

Phe Lys Gln Leu Val Glu Asp Leu Asp Arg Ile Leu Thr Val Thr Ser
        740                 745                 750

Thr Asp Glu Tyr Leu Asp Leu Ser Val Pro Phe Glu Gln Tyr Ser Pro
    755                 760                 765

Gly Gly Gln Asp Thr Pro Ser Ser Ser Ser Gly Asp Asp Ser Val
770                 775                 780

Phe Thr His Asp Leu Leu Pro Pro Gly Pro Pro Ser Asn Gly Gly Pro
785                 790                 795                 800

Arg Thr
```

<210> SEQ ID NO 11
<211> LENGTH: 2403
<212> TYPE: DNA
<213> ORGANISM: Mus musculus

<400> SEQUENCE: 11

| | | | | | |
|---|---|---|---|---|---|
| atggtagtcc | cggcctgcgt | gctagtgttc | tgcgtggcgg | tcgtggctgg | agctacttcc | 60 |
| gagcctcctg | gtccagagca | gcgagttgtg | cggagagcgg | cagaggttcc | agggcctgaa | 120 |
| cctagccagc | aggagcaggt | ggccttcggc | agtggggaca | ccgtggagct | gagctgccat | 180 |
| cctcctggag | gtgcccccac | agggcccacg | gtctgggcta | aggatggtac | aggtctggtg | 240 |
| gcctcccacc | gcatcctggt | ggggcctcag | aggctgcaag | tgctaaatgc | ctcccacgaa | 300 |
| gatgcagggg | tctacagctg | ccagcaccgg | ctcactcggc | gtgtgctgtg | ccacttcagt | 360 |
| gtgcgtgtaa | cagatgctcc | atcctcagga | gatgacgaag | atggggagga | cgtggctgaa | 420 |
| gacacagggg | ctccttattg | gactcgcccg | gagcgaatgg | ataagaaact | gctggctgtg | 480 |
| ccagccgcaa | acactgtccg | cttccgctgc | ccagctgctg | gcaaccctac | ccctccatc | 540 |
| tcctggctga | gaatggcaa | agaattccga | ggggagcatc | gcattggggg | catcaagctc | 600 |
| cggcaccagc | agtggagctt | ggtcatggaa | agtgtggtac | cctccgatcg | tgcaactat | 660 |
| acctgtgtag | ttgagaacaa | gtttggcagc | atccggcaga | catacacact | ggatgtgctg | 720 |
| gagcgctccc | cacaccggcc | catcctgcag | gctgggctgc | cggccaacca | gacagccatt | 780 |
| ctaggcagtg | acgtggagtt | ccactgcaag | gtgtacagcg | atgcacagcc | acacatccag | 840 |
| tggctgaagc | acgtggaagt | gaacggcagc | aaggtggggc | ctgacggcac | gccctacgtc | 900 |
| actgtactca | agactgcagg | cgctaacacc | accgacaagg | agctagaggt | tctgtccttg | 960 |
| cacaatgtca | cctttgagga | cgcggggag | tacacctgcc | tggcgggcaa | ttctattggg | 1020 |
| ttttcccatc | actctgcgtg | gctggtggtg | ctgccagctg | aggaggagct | gatggaaact | 1080 |
| gatgaggctg | gcagcgtgta | cgcaggcgtc | ctcagctacg | ggtggtctt | cttcctcttc | 1140 |
| atcctggtgg | tggcagctgt | gatactctgc | cgcctgcgca | gtcccccaaa | gaagggcttg | 1200 |
| ggctcgccca | ccgtgcacaa | ggtctctcgc | ttcccgctta | agcgacaggt | gtccttggaa | 1260 |
| tctaactcct | ctatgaactc | caacacaccc | cttgtccgga | ttgcccggct | gtcctcagga | 1320 |
| gaaggtcctg | ttctggccaa | tgtttctgaa | cttgagctgc | ctgctgaccc | caagtgggag | 1380 |
| ctatccagga | cccggctgac | acttggtaag | cctcttggag | aaggctgctt | tggacaggtg | 1440 |
| gtcatggcag | aagctattgg | catcgacaag | gaccgtactg | ccaagcctgt | caccgtggcc | 1500 |
| gtgaagatgc | tgaaagatga | tgcgactgac | aaggacctgt | cggacctggt | atctgagatg | 1560 |

```
gagatgatga aaatgattgg caagcacaag aacatcatta acctgctggg ggcgtgcaca    1620
cagggtgggc ccctgtatgt gctggtggag tacgcagcca agggcaatct ccgggagttc    1680
cttcgggcgc ggcggcctcc aggcatggac tactcctttg atgcctgcag ctgccagag     1740 gaacagctca cctgcaagga tctagtgtcc tgtgcctacc aggtggcacg gggcatggaa    1800
tacttggctt ctcagaagtg tattcacaga gacttggctg ccagaaacgt cctggtgacc    1860
gaggacaatg tgatgaagat tgcggacttt ggcctggctc gagatgtgca aacctggac     1920 tactacaaga agaccacaaa tggccggcta cctgtgaagt ggatggcacc agaggccctt    1980
tttgaccgag tctacaccca ccagagtgat gtttggtctt ttggtgtcct cctctgggag    2040
atctttacgc tggggggctc accgtatcct ggcatcccag tggaagagct tttcaagctg    2100
ttgaaagagg gccaccgcat ggacaagcca gccagctgca cacatgacct gtacatgatc    2160
atgcgggaat gttggcatgc ggtgccttca cagaggccca ccttcaagca gttggtagag    2220
gatttagacc gcatcctcac tgtgacatca accgacgagt acttggacct ctccgtgccg    2280
tttgagcagt actcgccagg tggccaggac acgcctagct ccagctcgtc cggagatgac    2340
tcggtgttca cccatgacct gctaccccca ggtccaccca gtaacggggg acctcggacg    2400
tga                                                                  2403
```

<210> SEQ ID NO 12
<211> LENGTH: 800
<212> TYPE: PRT
<213> ORGANISM: Mus musculus

<400> SEQUENCE: 12

```
Met Val Val Pro Ala Cys Val Leu Val Phe Cys Val Ala Val Ala
1               5                   10                  15

Gly Ala Thr Ser Glu Pro Pro Gly Pro Glu Gln Arg Val Arg Arg
                20                  25                  30

Ala Ala Glu Val Pro Gly Pro Glu Pro Ser Gln Gln Glu Gln Val Ala
            35                  40                  45

Phe Gly Ser Gly Asp Thr Val Glu Leu Ser Cys His Pro Pro Gly Gly
        50                  55                  60

Ala Pro Thr Gly Pro Thr Val Trp Ala Lys Asp Gly Thr Gly Leu Val
65                  70                  75                  80

Ala Ser His Arg Ile Leu Val Gly Pro Gln Arg Leu Gln Val Leu Asn
                85                  90                  95

Ala Ser His Glu Asp Ala Gly Val Tyr Ser Cys Gln His Arg Leu Thr
            100                 105                 110

Arg Arg Val Leu Cys His Phe Ser Val Arg Val Thr Asp Ala Pro Ser
        115                 120                 125

Ser Gly Asp Asp Glu Asp Gly Glu Asp Val Ala Glu Asp Thr Gly Ala
    130                 135                 140

Pro Tyr Trp Thr Arg Pro Glu Arg Met Asp Lys Lys Leu Leu Ala Val
145                 150                 155                 160

Pro Ala Ala Asn Thr Val Arg Phe Arg Cys Pro Ala Ala Gly Asn Pro
                165                 170                 175

Thr Pro Ser Ile Ser Trp Leu Lys Asn Gly Lys Glu Phe Arg Gly Glu
            180                 185                 190

His Arg Ile Gly Gly Ile Lys Leu Arg His Gln Gln Trp Ser Leu Val
        195                 200                 205

Met Glu Ser Val Val Pro Ser Asp Arg Gly Asn Tyr Thr Cys Val Val
```

-continued

```
            210                 215                 220
Glu Asn Lys Phe Gly Ser Ile Arg Gln Thr Tyr Thr Leu Asp Val Leu
225                 230                 235                 240

Glu Arg Ser Pro His Arg Pro Ile Leu Gln Ala Gly Leu Pro Ala Asn
                245                 250                 255

Gln Thr Ala Ile Leu Gly Ser Asp Val Glu Phe His Cys Lys Val Tyr
                260                 265                 270

Ser Asp Ala Gln Pro His Ile Gln Trp Leu Lys His Val Glu Val Asn
                275                 280                 285

Gly Ser Lys Val Gly Pro Asp Gly Thr Pro Tyr Val Thr Val Leu Lys
290                 295                 300

Thr Ala Gly Ala Asn Thr Thr Asp Lys Glu Leu Glu Val Leu Ser Leu
305                 310                 315                 320

His Asn Val Thr Phe Glu Asp Ala Gly Glu Tyr Thr Cys Leu Ala Gly
                325                 330                 335

Asn Ser Ile Gly Phe Ser His His Ser Ala Trp Leu Val Val Leu Pro
                340                 345                 350

Ala Glu Glu Glu Leu Met Glu Thr Asp Glu Ala Gly Ser Val Tyr Ala
                355                 360                 365

Gly Val Leu Ser Tyr Gly Val Phe Phe Leu Phe Ile Leu Val Val
                370                 375                 380

Ala Ala Val Ile Leu Cys Arg Leu Arg Ser Pro Lys Lys Gly Leu
385                 390                 395                 400

Gly Ser Pro Thr Val His Lys Val Ser Arg Phe Pro Leu Lys Arg Gln
                405                 410                 415

Val Ser Leu Glu Ser Asn Ser Ser Met Asn Ser Asn Thr Pro Leu Val
                420                 425                 430

Arg Ile Ala Arg Leu Ser Ser Gly Glu Gly Pro Val Leu Ala Asn Val
                435                 440                 445

Ser Glu Leu Glu Leu Pro Ala Asp Pro Lys Trp Glu Leu Ser Arg Thr
                450                 455                 460

Arg Leu Thr Leu Gly Lys Pro Leu Gly Glu Gly Cys Phe Gly Gln Val
465                 470                 475                 480

Val Met Ala Glu Ala Ile Gly Ile Asp Lys Asp Arg Thr Ala Lys Pro
                485                 490                 495

Val Thr Val Ala Val Lys Met Leu Lys Asp Asp Ala Thr Asp Lys Asp
                500                 505                 510

Leu Ser Asp Leu Val Ser Glu Met Glu Met Met Lys Met Ile Gly Lys
                515                 520                 525

His Lys Asn Ile Ile Asn Leu Leu Gly Ala Cys Thr Gln Gly Gly Pro
                530                 535                 540

Leu Tyr Val Leu Val Glu Tyr Ala Ala Lys Gly Asn Leu Arg Glu Phe
545                 550                 555                 560

Leu Arg Ala Arg Arg Pro Pro Gly Met Asp Tyr Ser Phe Asp Ala Cys
                565                 570                 575

Arg Leu Pro Glu Glu Gln Leu Thr Cys Lys Asp Leu Val Ser Cys Ala
                580                 585                 590

Tyr Gln Val Ala Arg Gly Met Glu Tyr Leu Ala Ser Gln Lys Cys Ile
                595                 600                 605

His Arg Asp Leu Ala Ala Arg Asn Val Leu Val Thr Glu Asp Asn Val
                610                 615                 620

Met Lys Ile Ala Asp Phe Gly Leu Ala Arg Asp Val His Asn Leu Asp
625                 630                 635                 640
```

```
Tyr Tyr Lys Lys Thr Thr Asn Gly Arg Leu Pro Val Lys Trp Met Ala
            645                 650                 655
Pro Glu Ala Leu Phe Asp Arg Val Tyr Thr His Gln Ser Asp Val Trp
            660                 665                 670
Ser Phe Gly Val Leu Leu Trp Glu Ile Phe Thr Leu Gly Gly Ser Pro
            675                 680                 685
Tyr Pro Gly Ile Pro Val Glu Glu Leu Phe Lys Leu Leu Lys Glu Gly
            690                 695                 700
His Arg Met Asp Lys Pro Ala Ser Cys Thr His Asp Leu Tyr Met Ile
705                 710                 715                 720
Met Arg Glu Cys Trp His Ala Val Pro Ser Gln Arg Pro Thr Phe Lys
            725                 730                 735
Gln Leu Val Glu Asp Leu Asp Arg Ile Leu Thr Val Thr Ser Thr Asp
            740                 745                 750
Glu Tyr Leu Asp Leu Ser Val Pro Phe Glu Gln Tyr Ser Pro Gly Gly
            755                 760                 765
Gln Asp Thr Pro Ser Ser Ser Ser Gly Asp Asp Ser Val Phe Thr
            770                 775                 780
His Asp Leu Leu Pro Pro Gly Pro Pro Ser Asn Gly Gly Pro Arg Thr
785                 790                 795                 800

<210> SEQ ID NO 13
<211> LENGTH: 2349
<212> TYPE: DNA
<213> ORGANISM: Mus musculus

<400> SEQUENCE: 13
atggtagtcc cggcctgcgt gctagtgttc tgcgtggcgg tcgtggctgg agctacttcc      60
gagcctcctg gtccagagca gcgagttgtg cggagagcgg cagaggttcc agggcctgaa    120
cctagccagc aggagcaggt ggccttcggc agtggggaca ccgtggagct gagctgccat    180
cctcctggag gtgcccccac agggcccacg gtctgggcta aggatggtac aggtctggtg    240
gcctcccacc gcatcctggt ggggcctcag aggctgcaag tgctaaatgc ctcccacgaa    300
gatgcagggg tctacagctg ccagcaccgg ctcactcggc gtgtgctgtg ccacttcagt    360
gtgcgtgtaa cagggctccc ttattggact cgcccggagc gaatggataa gaaactgctg    420
gctgtgccag ccgcaaacac tgtccgcttc cgctgcccag ctgctggcaa ccctaccccc    480
tccatctcct ggctgaagaa tggcaaagaa ttccgagggg agcatcgcat tgggggcatc    540
aagctccggc accagcagtg gagcttggtc atggaaagtg tggtaccctc cgatcgtggc    600
aactatacct gtgtagttga aacaagtttt ggcagcatcc ggcagacata cactggat      660
gtgctggagc gctccccaca ccggcccatc ctgcaggctg gctgccggc caaccagaca    720
gccattctag cagtgacgt ggagttccac tgcaaggtgt acagcgatgc acagccacac    780
atccagtggc tgaagcacgt ggaagtgaac ggcagcaagg tgggccctga cggcacgccc    840
tacgtcactg tactcaagac tgcaggcgct aacaccaccg acaaggagct agaggttctg    900
tccttgcaca atgtcacctt tgaggacgcg ggggagtaca cctgcctggc gggcaattct    960
attgggtttt cccatcactc tgcgtggctg gtggtgctgc cagctgagga ggagctgatg   1020
gaaactgatg aggctggcag cgtgtacgca ggcgtcctca gctacgggt ggtcttcttc   1080
ctcttcatcc tggtggtggc agctgtgata ctctgccgcc tgcgcagtcc cccaaagaag   1140
ggcttgggct cgcccaccgt gcacaaggtc tctcgcttcc cgcttaagcg acaggtgtcc   1200
```

-continued

```
ttggaatcta actcctctat gaactccaac acaccccttg tccggattgc ccggctgtcc    1260
tcaggagaag gtcctgttct ggccaatgtt tctgaacttg agctgcctgc tgaccccaag    1320
tgggagctat ccaggacccg gctgacactt ggtaagcctc ttggagaagg ctgctttgga    1380
caggtggtca tggcagaagc tattggcatc gacaaggacc gtactgccaa gcctgtcacc    1440
gtggccgtga agatgctgaa agatgatgcg actgacaagg acctgtcgga cctggtatct    1500
gagatggaga tgatgaaaat gattggcaag cacaagaaca tcattaacct gctggggggcg    1560 tgcacacagg gtgggcccct gtatgtgctg gtggagtacg cagccaaggg caatctccgg    1620
gagttccttc gggcgcggcg gcctccaggc atggactact cctttgatgc ctgcaggctg    1680
ccagaggaac agctcacctg caaggatcta gtgtcctgtg cctaccaggt ggcacggggc    1740
atggaatact tggcttctca gaagtgtatt cacagagact ggctgccag aaacgtcctg     1800 gtgaccgagg acaatgtgat gaagattgcg actttggcc tggctcgaga tgtgcacaac     1860
ctggactact acaagaagac cacaaatggc cggctacctg tgaagtggat ggcaccagag    1920 gcccttttg accgagtcta cacccaccag agtgatgttt ggtcttttgg tgtcctcctc    1980
tgggagatct ttacgctggg gggctcaccg tatcctggca tcccagtgga agagcttttc    2040
aagctgttga agagggcca ccgcatggac aagccagcca gctgcacaca tgacctgtac    2100
atgatcatgc gggaatgttg gcatgcggtg ccttcacaga ggcccacctt caagcagttg    2160
gtagaggatt tagaccgcat cctcactgtg acatcaaccg acgagtactt ggacctctcc    2220
gtgccgtttg agcagtactc gccaggtggc caggacacgc ctagctccag ctcgtccgga    2280
gatgactcgg tgttcaccca tgacctgcta ccccaggtc cacccagtaa cgggggacct    2340
cggacgtga                                                           2349
```

<210> SEQ ID NO 14
<211> LENGTH: 782
<212> TYPE: PRT
<213> ORGANISM: Mus musculus

<400> SEQUENCE: 14

Met Val Val Pro Ala Cys Val Leu Val Phe Cys Val Ala Val Ala
1               5                   10                  15

Gly Ala Thr Ser Glu Pro Pro Gly Pro Glu Gln Arg Val Arg Arg
            20                  25                  30

Ala Ala Glu Val Pro Gly Pro Glu Pro Ser Gln Gln Glu Gln Val Ala
        35                  40                  45

Phe Gly Ser Gly Asp Thr Val Glu Leu Ser Cys His Pro Pro Gly Gly
    50                  55                  60

Ala Pro Thr Gly Pro Thr Val Trp Ala Lys Asp Gly Thr Gly Leu Val
65                  70                  75                  80

Ala Ser His Arg Ile Leu Val Gly Pro Gln Arg Leu Gln Val Leu Asn
                85                  90                  95

Ala Ser His Glu Asp Ala Gly Val Tyr Ser Cys Gln His Arg Leu Thr
            100                 105                 110

Arg Arg Val Leu Cys His Phe Ser Val Arg Val Thr Gly Ala Pro Tyr
        115                 120                 125

Trp Thr Arg Pro Glu Arg Met Asp Lys Lys Leu Leu Ala Val Pro Ala
    130                 135                 140

Ala Asn Thr Val Arg Phe Arg Cys Pro Ala Ala Gly Asn Pro Thr Pro
145                 150                 155                 160

Ser Ile Ser Trp Leu Lys Asn Gly Lys Glu Phe Arg Gly Glu His Arg

```
                165                 170                 175
Ile Gly Gly Ile Lys Leu Arg His Gln Gln Trp Ser Leu Val Met Glu
            180                 185                 190
Ser Val Val Pro Ser Asp Arg Gly Asn Tyr Thr Cys Val Val Glu Asn
            195                 200                 205
Lys Phe Gly Ser Ile Arg Gln Thr Tyr Thr Leu Asp Val Leu Glu Arg
            210                 215                 220
Ser Pro His Arg Pro Ile Leu Gln Ala Gly Leu Pro Ala Asn Gln Thr
225                 230                 235                 240
Ala Ile Leu Gly Ser Asp Val Glu Phe His Cys Lys Val Tyr Ser Asp
                245                 250                 255
Ala Gln Pro His Ile Gln Trp Leu Lys His Val Glu Val Asn Gly Ser
            260                 265                 270
Lys Val Gly Pro Asp Gly Thr Pro Tyr Val Thr Val Leu Lys Thr Ala
            275                 280                 285
Gly Ala Asn Thr Thr Asp Lys Glu Leu Glu Val Leu Ser Leu His Asn
            290                 295                 300
Val Thr Phe Glu Asp Ala Gly Glu Tyr Thr Cys Leu Ala Gly Asn Ser
305                 310                 315                 320
Ile Gly Phe Ser His His Ser Ala Trp Leu Val Val Leu Pro Ala Glu
                325                 330                 335
Glu Glu Leu Met Glu Thr Asp Glu Ala Gly Ser Val Tyr Ala Gly Val
            340                 345                 350
Leu Ser Tyr Gly Val Val Phe Phe Leu Phe Ile Leu Val Val Ala Ala
            355                 360                 365
Val Ile Leu Cys Arg Leu Arg Ser Pro Pro Lys Lys Gly Leu Gly Ser
            370                 375                 380
Pro Thr Val His Lys Val Ser Arg Phe Pro Leu Lys Arg Gln Val Ser
385                 390                 395                 400
Leu Glu Ser Asn Ser Ser Met Asn Ser Asn Thr Pro Leu Val Arg Ile
                405                 410                 415
Ala Arg Leu Ser Ser Gly Glu Gly Pro Val Leu Ala Asn Val Ser Glu
            420                 425                 430
Leu Glu Leu Pro Ala Asp Pro Lys Trp Glu Leu Ser Arg Thr Arg Leu
            435                 440                 445
Thr Leu Gly Lys Pro Leu Gly Glu Gly Cys Phe Gly Gln Val Val Met
            450                 455                 460
Ala Glu Ala Ile Gly Ile Asp Lys Asp Arg Thr Ala Lys Pro Val Thr
465                 470                 475                 480
Val Ala Val Lys Met Leu Lys Asp Asp Ala Thr Asp Lys Asp Leu Ser
                485                 490                 495
Asp Leu Val Ser Glu Met Glu Met Met Lys Met Ile Gly Lys His Lys
            500                 505                 510
Asn Ile Ile Asn Leu Leu Gly Ala Cys Thr Gln Gly Gly Pro Leu Tyr
            515                 520                 525
Val Leu Val Glu Tyr Ala Ala Lys Gly Asn Leu Arg Glu Phe Leu Arg
            530                 535                 540
Ala Arg Arg Pro Pro Gly Met Asp Tyr Ser Phe Asp Ala Cys Arg Leu
545                 550                 555                 560
Pro Glu Glu Gln Leu Thr Cys Lys Asp Leu Val Ser Cys Ala Tyr Gln
                565                 570                 575
Val Ala Arg Gly Met Glu Tyr Leu Ala Ser Gln Lys Cys Ile His Arg
            580                 585                 590
```

```
Asp Leu Ala Ala Arg Asn Val Leu Val Thr Glu Asp Asn Val Met Lys
            595                 600                 605

Ile Ala Asp Phe Gly Leu Ala Arg Asp Val His Asn Leu Asp Tyr Tyr
        610                 615                 620

Lys Lys Thr Thr Asn Gly Arg Leu Pro Val Lys Trp Met Ala Pro Glu
625                 630                 635                 640

Ala Leu Phe Asp Arg Val Tyr Thr His Gln Ser Asp Val Trp Ser Phe
                645                 650                 655

Gly Val Leu Leu Trp Glu Ile Phe Thr Leu Gly Gly Ser Pro Tyr Pro
            660                 665                 670

Gly Ile Pro Val Glu Glu Leu Phe Lys Leu Leu Lys Glu Gly His Arg
        675                 680                 685

Met Asp Lys Pro Ala Ser Cys Thr His Asp Leu Tyr Met Ile Met Arg
    690                 695                 700

Glu Cys Trp His Ala Val Pro Ser Gln Arg Pro Thr Phe Lys Gln Leu
705                 710                 715                 720

Val Glu Asp Leu Asp Arg Ile Leu Thr Val Thr Ser Thr Asp Glu Tyr
                725                 730                 735

Leu Asp Leu Ser Val Pro Phe Glu Gln Tyr Ser Pro Gly Gly Gln Asp
            740                 745                 750

Thr Pro Ser Ser Ser Ser Gly Asp Asp Ser Val Phe Thr His Asp
        755                 760                 765

Leu Leu Pro Pro Gly Pro Pro Ser Asn Gly Gly Pro Arg Thr
    770                 775                 780
```

<210> SEQ ID NO 15
<211> LENGTH: 2409
<212> TYPE: DNA
<213> ORGANISM: Rattus norvegicus

<400> SEQUENCE: 15

```
atggtagtcc cggcctgcgt gctagtgttc tgcgtggcgg tcgtggctgg agttacttcc      60
gagcctcccg ttccagagca gcgagttggt cggagagcgg cagaggttcc agggcctgaa     120
cctagccagc aggagcaggt ggccttcggc agtggggaca ctgtggagct gagctgccat     180
ccgcctggag gtgcccccac aggccccact ctctgggcta aggacggtgt ggggctggtg     240
gcctcccacc gtatcctggt ggggcctcag aggcttcaag tgctaaacgc cacccatgag     300
gatgctgggg tctacagctg ccagcagcgg ctaacccggc gtgtgctgtg ccactttagt     360
gtgcgtgtaa cagatgctcc gtcctcagga gatgacgaag atggggagga cgtggctgaa     420
gacacagggg ctccttactg gactcgaccg gagcgtatgg ataagaaact gctggctgtg     480
ccagctgcaa acactgtacg cttccgctgc ccagctgctg caaccccac ccctccatc      540
ccctggctga gaacggcaa agaattccga ggggagcacc gcattggggg cattaagctc     600
cggcaccagc agtggagctt ggtcatggaa agtgtggtgc cctctgaccg cggcaattac     660
acctgcgtgg ttgagaacaa gtttggcagc atccggcaga cgtacacccc tggatgtgctg    720
gagcgctccc cacaccggcc catcctgcag gctgggctgc cagccaacca gacagccgtt     780
ctgggcagtg acgtggagtt ccactgcaag gtgtacagcg acgcacagcc acacatccag     840
tggctgaagc acgtggaggt gaatgggagc aaggtgggcc ctgacggcac gcctacgtc      900
actgtactca gtcctggat cagtgagaat gtggaggcag acgcacgcct ccgcctggcc     960
aatgtgtcgg agcgggacgg gggcgagtac ctctgtcgag ccaccaattt cataggcgtg    1020
```

```
gccgagaagg cctttggct cgtgttcac gggccccaag cagccgagga ggagctgatg    1080
gaagttgacg aggctggcag cgtgtacgcg ggtgtcctca gctacggggt gggcttcttc    1140
ctcttcatcc tggtggtggc ggcagtgacg ctctgccgtc tgcgcagtcc cccaaagaag    1200
ggcctgggct cgcccaccgt gcacaaggtc tctcgcttcc cgcttaagcg acaggtgtcc    1260
ttggagtcta attcctctat gaactccaac acacctctcg tccggattgc ccggctgtcc    1320
tcaggagaag gtcctgtcct ggccaatgtt tctgaacttg agctgcctgc tgaccccaag    1380
tgggagctat ccaggacccg gctgacactc ggtaagcctc ttggagaagg ctgctttgga    1440
caggttgtca tggcagaagc tattggcatc gacaaggacc gcactgccaa gcctgtcacc    1500
gtggccgtga agatgctgaa agatgatgcg actgacaagg acctgtcgga cctggtgtct    1560
gagatggaga tgatgaaaat gattggcaag cacaagaaca tcattaacct gttgggggcc    1620
tgcacccagg gtgggcccct gtatgtgctg gtggagtatg cagccaaggg caacctgcga    1680
gagttcctcc gggcacggcg gcctccaggc atggattact ccttttgatgc ctgcaggctg    1740
ccagaggaac agctccacctg caaggatctg gtgtcctgtg cctaccaggt ggcacggggc    1800
atggagtact tggcttccca gaagtgtatt cacagagacc tggctgccag aaacgtgctg    1860
gtgactgagg acaatgtgat gaagattgca gactttggcc tggcccgaga tgtgcacaac    1920
ctggattact acaagaagac cacaaatggc cggctacctg tgaagtggat ggcaccagag    1980
gcccttttg accgagtcta cacccatcag agtgatgtct ggtcctttgg tgtcctcctc    2040
tgggagatct ttacactggg tgggtcacca tatcctggca tcccagtgga agagcttttc    2100
aagctgttga agaggggcca ccgcatggac aagccagcca actgcacaca tgacctgtac    2160
atgatcatgc gggaatgttg gcatgcagtg ccttcacaga ggcccacctt caagcagttg    2220
gtagaggatt tagaccgcat cctcacggtg acatcaactg acgagtactt ggacctctcg    2280
gtgccatttg aacagtactc gccaggtggc caagatactc ctagctccag ctcgtccggg    2340
gacgactctg tgttcacccc tgacctgcta cccccaggcc cacccagcaa tggggggacct    2400
cggacgtga                                                            2409
```

<210> SEQ ID NO 16  
<211> LENGTH: 802  
<212> TYPE: PRT  
<213> ORGANISM: Rattus norvegicus

<400> SEQUENCE: 16

Met Val Val Pro Ala Cys Val Leu Val Phe Cys Val Ala Val Ala
1               5                   10                  15

Gly Val Thr Ser Glu Pro Pro Gly Pro Glu Gln Arg Val Gly Arg Arg
            20                  25                  30

Ala Ala Glu Val Pro Gly Pro Glu Pro Ser Gln Gln Glu Gln Val Ala
        35                  40                  45

Phe Gly Ser Gly Asp Thr Val Glu Leu Ser Cys His Pro Pro Gly Gly
    50                  55                  60

Ala Pro Thr Gly Pro Thr Leu Trp Ala Lys Asp Gly Val Gly Leu Val
65                  70                  75                  80

Ala Ser His Arg Ile Leu Val Gly Pro Gln Arg Leu Gln Val Leu Asn
                85                  90                  95

Ala Thr His Glu Asp Ala Gly Val Tyr Ser Cys Gln Gln Arg Leu Thr
            100                 105                 110

Arg Arg Val Leu Cys His Phe Ser Val Arg Val Thr Asp Ala Pro Ser
        115                 120                 125

-continued

```
Ser Gly Asp Asp Glu Asp Gly Glu Asp Val Ala Glu Asp Thr Gly Ala
    130                 135                 140

Pro Tyr Trp Thr Arg Pro Glu Arg Met Asp Lys Lys Leu Leu Ala Val
145                 150                 155                 160

Pro Ala Ala Asn Thr Val Arg Phe Arg Cys Pro Ala Ala Gly Asn Pro
                165                 170                 175

Thr Pro Ser Ile Pro Trp Leu Lys Asn Gly Lys Glu Phe Arg Gly Glu
            180                 185                 190

His Arg Ile Gly Gly Ile Lys Leu Arg His Gln Gln Trp Ser Leu Val
        195                 200                 205

Met Glu Ser Val Val Pro Ser Asp Arg Gly Asn Tyr Thr Cys Val Val
    210                 215                 220

Glu Asn Lys Phe Gly Ser Ile Arg Gln Thr Tyr Thr Leu Asp Val Leu
225                 230                 235                 240

Glu Arg Ser Pro His Arg Pro Ile Leu Gln Ala Gly Leu Pro Ala Asn
                245                 250                 255

Gln Thr Ala Val Leu Gly Ser Asp Val Glu Phe His Cys Lys Val Tyr
            260                 265                 270

Ser Asp Ala Gln Pro His Ile Gln Trp Leu Lys His Val Glu Val Asn
        275                 280                 285

Gly Ser Lys Val Gly Pro Asp Gly Thr Pro Tyr Val Thr Val Leu Lys
    290                 295                 300

Ser Trp Ile Ser Glu Asn Val Glu Ala Asp Ala Arg Leu Arg Leu Ala
305                 310                 315                 320

Asn Val Ser Glu Arg Asp Gly Gly Glu Tyr Leu Cys Arg Ala Thr Asn
                325                 330                 335

Phe Ile Gly Val Ala Glu Lys Ala Phe Trp Leu Arg Val His Gly Pro
            340                 345                 350

Gln Ala Ala Glu Glu Glu Leu Met Glu Val Asp Glu Ala Gly Ser Val
        355                 360                 365

Tyr Ala Gly Val Leu Ser Tyr Gly Val Gly Phe Phe Leu Phe Ile Leu
    370                 375                 380

Val Val Ala Ala Val Thr Leu Cys Arg Leu Arg Ser Pro Pro Lys Lys
385                 390                 395                 400

Gly Leu Gly Ser Pro Thr Val His Lys Val Ser Arg Phe Pro Leu Lys
                405                 410                 415

Arg Gln Val Ser Leu Glu Ser Asn Ser Ser Met Asn Ser Asn Thr Pro
            420                 425                 430

Leu Val Arg Ile Ala Arg Leu Ser Ser Gly Glu Gly Pro Val Leu Ala
        435                 440                 445

Asn Val Ser Glu Leu Glu Leu Pro Ala Asp Pro Lys Trp Glu Leu Ser
    450                 455                 460

Arg Thr Arg Leu Thr Leu Gly Lys Pro Leu Gly Glu Gly Cys Phe Gly
465                 470                 475                 480

Gln Val Val Met Ala Glu Ala Ile Gly Ile Asp Lys Asp Arg Thr Ala
                485                 490                 495

Lys Pro Val Thr Val Ala Val Lys Met Leu Lys Asp Asp Ala Thr Asp
            500                 505                 510

Lys Asp Leu Ser Asp Leu Val Ser Glu Met Glu Met Met Lys Met Ile
        515                 520                 525

Gly Lys His Lys Asn Ile Ile Asn Leu Leu Gly Ala Cys Thr Gln Gly
    530                 535                 540
```

-continued

```
Gly Pro Leu Tyr Val Leu Val Glu Tyr Ala Ala Lys Gly Asn Leu Arg
545                 550                 555                 560

Glu Phe Leu Arg Ala Arg Arg Pro Pro Gly Met Asp Tyr Ser Phe Asp
                565                 570                 575

Ala Cys Arg Leu Pro Glu Glu Gln Leu Thr Cys Lys Asp Leu Val Ser
            580                 585                 590

Cys Ala Tyr Gln Val Ala Arg Gly Met Glu Tyr Leu Ala Ser Gln Lys
        595                 600                 605

Cys Ile His Arg Asp Leu Ala Ala Arg Asn Val Leu Thr Glu Asp
    610                 615                 620

Asn Val Met Lys Ile Ala Asp Phe Gly Leu Ala Arg Asp Val His Asn
625                 630                 635                 640

Leu Asp Tyr Tyr Lys Lys Thr Thr Asn Gly Arg Leu Pro Val Lys Trp
                645                 650                 655

Met Ala Pro Glu Ala Leu Phe Asp Arg Val Tyr Thr His Gln Ser Asp
                660                 665                 670

Val Trp Ser Phe Gly Val Leu Leu Trp Glu Ile Phe Thr Leu Gly Gly
            675                 680                 685

Ser Pro Tyr Pro Gly Ile Pro Val Glu Glu Leu Phe Lys Leu Leu Lys
        690                 695                 700

Glu Gly His Arg Met Asp Lys Pro Ala Asn Cys Thr His Asp Leu Tyr
705                 710                 715                 720

Met Ile Met Arg Glu Cys Trp His Ala Val Pro Ser Gln Arg Pro Thr
                725                 730                 735

Phe Lys Gln Leu Val Glu Asp Leu Asp Arg Ile Leu Thr Val Thr Ser
                740                 745                 750

Thr Asp Glu Tyr Leu Asp Leu Ser Val Pro Phe Glu Gln Tyr Ser Pro
            755                 760                 765

Gly Gly Gln Asp Thr Pro Ser Ser Ser Ser Gly Asp Asp Ser Val
        770                 775                 780

Phe Thr His Asp Leu Leu Pro Pro Gly Pro Pro Ser Asn Gly Gly Pro
785                 790                 795                 800

Arg Thr
```

<210> SEQ ID NO 17
<211> LENGTH: 2403
<212> TYPE: DNA
<213> ORGANISM: Rattus norvegicus

<400> SEQUENCE: 17

```
atggtagtcc cggcctgcgt gctagtgttc tgcgtggcgg tcgtggctgg agttacttcc      60
gagcctcccg gtccagagca gcgagttggt cggagagcgg cagaggttcc agggcctgaa     120
cctagccagc aggagcaggt ggccttcggc agtggggaca ctgtggagct gagctgccat     180
ccgcctggag gtgcccccac aggccccact ctctgggcta aggacggtgt ggggctggtg     240
gcctccacc gtatcctggt ggggcctcag aggcttcaag tgctaaacgc acccatgag      300
gatgctgggg tctacagctg ccagcagcgg ctaacccggc gtgtgctgtg ccactttagt     360
gtgcgtgtaa cagatgctcc gtcctcagga gatgacgaag atggggagga cgtggctgaa     420
gacacagggg ctccttactg gactcgaccg gagcgtatgg ataagaaact gctggctgtg     480
ccagctgcaa acactgtacg cttccgctgc ccagctgctg caacccccac ccctccatc      540
ccctggctga gaacggcaa agaattccga ggggagcacc gcattggggg cattaagctc     600
cggcaccagc agtggagctt ggtcatggaa agtgtggtgc cctctgaccg cggcaattac     660
```

-continued

```
acctgcgtgg ttgagaacaa gtttggcagc atccggcaga cgtacaccct ggatgtgctg      720
gagcgctccc cacaccggcc catcctgcag gctgggctgc cagccaacca gacagccgtt      780
ctgggcagtg acgtggagtt ccactgcaag gtgtacagcg acgcacagcc acacatccag      840
tggctgaagc acgtggaggt gaatgggagc aaggtgggcc ctgacggcac gccctacgtc      900
actgtactca agactgcagg agctaacacc accgacaggg agctagaggt tctgtccttg      960
cacaatgtca cctttgagga tgcggggag tacacctgcc tggcgggcaa ttctatcggg     1020
ttttcccatc actctgcgtg gctggtggtg ctgccagccg aggaggagct gatggaagtt     1080
gacgaggctg gcagcgtgta cgcgggtgtc ctcagctacg gggtgggctt cttcctcttc     1140
atcctggtgg tggcggcagt gacgctctgc cgtctgcgca gtcccccaaa gaagggcctg     1200
ggctcgccca ccgtgcacaa ggtctctcgc ttcccgctta agcgacaggt gtccttggag     1260
tctaattcct ctatgaactc caacacacct ctcgtccgga ttgcccggct gtcctcagga     1320
gaaggtcctg tcctggccaa tgtttctgaa cttgagctgc ctgctgaccc caagtgggag     1380
ctatccagga cccggctgac actcggtaag cctcttggag aaggctgctt tggacaggtt     1440
gtcatggcag aagctattgg catcgacaag gaccgcactg ccaagcctgt caccgtggcc     1500
gtgaagatgc tgaaagatga tgcgactgac aaggacctgt cggacctggt gtctgagatg     1560
gagatgatga aaatgattgg caagcacaag aacatcatta acctgttggg ggcctgcacc     1620
cagggtgggc cctgtatgt gctggtggag tatgcagcca agggcaacct gcgagagttc     1680
ctccgggcac ggcggcctcc aggcatggat tactcctttg atgcctgcag gctgccagag     1740
gaacagctca cctgcaagga tctggtgtcc tgtgcctacc aggtggcacg gggcatggag     1800
tacttggctt cccagaagtg tattcacaga gacctggctg ccagaaacgt gctggtgact     1860
gaggacaatg tgatgaagat tgcagacttt ggcctggccc gagatgtgca acctggat     1920 tactacaaga gaccacaaa tggccggcta cctgtgaagt ggatggcacc agaggccctt     1980
tttgaccgag tctacaccca tcagagtgat gtctggtcct tggtgtcct cctctgggag     2040 atctttacac tgggtgggtc accatatcct ggcatcccag tggaagagct tttcaagctg     2100
ttgaaagagg ccaccgcat ggacaagcca gccaactgca cacatgacct gtacatgatc     2160
atgcgggaat gttggcatgc agtgccttca cagaggccca ccttcaagca gttggtagag     2220
gatttagacc gcatcctcac ggtgacatca actgacgagt acttggaccct ctcggtgcca     2280 tttgaacagt actcgccagg tggccaagat actcctagct ccagctcgtc cggggacgac     2340
tctgtgttca cccatgacct gctacccca ggcccaccca gcaatggggg acctcggacg     2400
tga                                                                   2403
```

<210> SEQ ID NO 18
<211> LENGTH: 800
<212> TYPE: PRT
<213> ORGANISM: Rattus norvegicus

<400> SEQUENCE: 18

```
Met Val Val Pro Ala Cys Val Leu Val Phe Cys Val Ala Val Val Ala
1               5                   10                  15

Gly Val Thr Ser Glu Pro Pro Gly Pro Glu Gln Arg Val Gly Arg Arg
            20                  25                  30

Ala Ala Glu Val Pro Gly Pro Glu Pro Ser Gln Gln Glu Gln Val Ala
        35                  40                  45

Phe Gly Ser Gly Asp Thr Val Glu Leu Ser Cys His Pro Pro Gly Gly
```

```
                50                   55                   60
Ala Pro Thr Gly Pro Thr Leu Trp Ala Lys Asp Gly Val Gly Leu Val
 65                  70                  75                  80

Ala Ser His Arg Ile Leu Val Gly Pro Gln Arg Leu Gln Val Leu Asn
                    85                  90                  95

Ala Thr His Glu Asp Ala Gly Val Tyr Ser Cys Gln Gln Arg Leu Thr
                100                 105                 110

Arg Arg Val Leu Cys His Phe Ser Val Arg Val Thr Asp Ala Pro Ser
                115                 120                 125

Ser Gly Asp Asp Glu Asp Gly Glu Asp Val Ala Glu Asp Thr Gly Ala
                130                 135                 140

Pro Tyr Trp Thr Arg Pro Glu Arg Met Asp Lys Lys Leu Leu Ala Val
145                 150                 155                 160

Pro Ala Ala Asn Thr Val Arg Phe Arg Cys Pro Ala Ala Gly Asn Pro
                165                 170                 175

Thr Pro Ser Ile Pro Trp Leu Lys Asn Gly Lys Glu Phe Arg Gly Glu
                180                 185                 190

His Arg Ile Gly Gly Ile Lys Leu Arg His Gln Gln Trp Ser Leu Val
                195                 200                 205

Met Glu Ser Val Val Pro Ser Asp Arg Gly Asn Tyr Thr Cys Val Val
210                 215                 220

Glu Asn Lys Phe Gly Ser Ile Arg Gln Thr Tyr Thr Leu Asp Val Leu
225                 230                 235                 240

Glu Arg Ser Pro His Arg Pro Ile Leu Gln Ala Gly Leu Pro Ala Asn
                245                 250                 255

Gln Thr Ala Val Leu Gly Ser Asp Val Glu Phe His Cys Lys Val Tyr
                260                 265                 270

Ser Asp Ala Gln Pro His Ile Gln Trp Leu Lys His Val Glu Val Asn
                275                 280                 285

Gly Ser Lys Val Gly Pro Asp Gly Thr Pro Tyr Val Thr Val Leu Lys
                290                 295                 300

Thr Ala Gly Ala Asn Thr Thr Asp Arg Glu Leu Glu Val Leu Ser Leu
305                 310                 315                 320

His Asn Val Thr Phe Glu Asp Ala Gly Glu Tyr Thr Cys Leu Ala Gly
                325                 330                 335

Asn Ser Ile Gly Phe Ser His His Ser Ala Trp Leu Val Val Leu Pro
                340                 345                 350

Ala Glu Glu Glu Leu Met Glu Val Asp Glu Ala Gly Ser Val Tyr Ala
                355                 360                 365

Gly Val Leu Ser Tyr Gly Val Gly Phe Phe Leu Phe Ile Leu Val Val
                370                 375                 380

Ala Ala Val Thr Leu Cys Arg Leu Arg Ser Pro Pro Lys Lys Gly Leu
385                 390                 395                 400

Gly Ser Pro Thr Val His Lys Val Ser Arg Phe Pro Leu Lys Arg Gln
                405                 410                 415

Val Ser Leu Glu Ser Asn Ser Ser Met Asn Ser Asn Thr Pro Leu Val
                420                 425                 430

Arg Ile Ala Arg Leu Ser Ser Gly Glu Gly Pro Val Leu Ala Asn Val
                435                 440                 445

Ser Glu Leu Glu Leu Pro Ala Asp Pro Lys Trp Glu Leu Ser Arg Thr
                450                 455                 460

Arg Leu Thr Leu Gly Lys Pro Leu Gly Glu Gly Cys Phe Gly Gln Val
465                 470                 475                 480
```

Val Met Ala Glu Ala Ile Gly Ile Asp Lys Asp Arg Thr Ala Lys Pro
            485                 490                 495

Val Thr Val Ala Val Lys Met Leu Lys Asp Asp Ala Thr Asp Lys Asp
            500                 505                 510

Leu Ser Asp Leu Val Ser Glu Met Glu Met Met Lys Met Ile Gly Lys
            515                 520                 525

His Lys Asn Ile Ile Asn Leu Leu Gly Ala Cys Thr Gln Gly Gly Pro
            530                 535                 540

Leu Tyr Val Leu Val Glu Tyr Ala Ala Lys Gly Asn Leu Arg Glu Phe
545                 550                 555                 560

Leu Arg Ala Arg Arg Pro Pro Gly Met Asp Tyr Ser Phe Asp Ala Cys
            565                 570                 575

Arg Leu Pro Glu Glu Gln Leu Thr Cys Lys Asp Leu Val Ser Cys Ala
            580                 585                 590

Tyr Gln Val Ala Arg Gly Met Glu Tyr Leu Ala Ser Gln Lys Cys Ile
            595                 600                 605

His Arg Asp Leu Ala Ala Arg Asn Val Leu Val Thr Glu Asp Asn Val
            610                 615                 620

Met Lys Ile Ala Asp Phe Gly Leu Ala Arg Asp Val His Asn Leu Asp
625                 630                 635                 640

Tyr Tyr Lys Lys Thr Thr Asn Gly Arg Leu Pro Val Lys Trp Met Ala
            645                 650                 655

Pro Glu Ala Leu Phe Asp Arg Val Tyr Thr His Gln Ser Asp Val Trp
            660                 665                 670

Ser Phe Gly Val Leu Leu Trp Glu Ile Phe Thr Leu Gly Gly Ser Pro
            675                 680                 685

Tyr Pro Gly Ile Pro Val Glu Glu Leu Phe Lys Leu Leu Lys Glu Gly
            690                 695                 700

His Arg Met Asp Lys Pro Ala Asn Cys Thr His Asp Leu Tyr Met Ile
705                 710                 715                 720

Met Arg Glu Cys Trp His Ala Val Pro Ser Gln Arg Pro Thr Phe Lys
            725                 730                 735

Gln Leu Val Glu Asp Leu Asp Arg Ile Leu Thr Val Thr Ser Thr Asp
            740                 745                 750

Glu Tyr Leu Asp Leu Ser Val Pro Phe Glu Gln Tyr Ser Pro Gly Gly
            755                 760                 765

Gln Asp Thr Pro Ser Ser Ser Ser Gly Asp Asp Ser Val Phe Thr
            770                 775                 780

His Asp Leu Leu Pro Pro Gly Pro Pro Ser Asn Gly Gly Pro Arg Thr
785                 790                 795                 800

<210> SEQ ID NO 19
<211> LENGTH: 2421
<212> TYPE: DNA
<213> ORGANISM: Gallus gallus

<400> SEQUENCE: 19
atgcgggcgg cctggggctc cgtctggtgc ctgtgcctgg cggcggccgt cggagcgctg      60
ccggcggcgc gccggcgcgg agcggagcgg agcggcgggc aggcggcaga atacttgagg     120
agcgagaccg cctttctgga agagttggtg tttggaagtg agataccat tgaactttcc     180 tgtaacaccc agagctcttc tgtgtcagtt ttctggttta agatggtat tgggattgca     240 ccttccaaca gaactcatat tggacaaaaa ctgttgaaga taatcaatgt gtcatatgac     300

-continued

| | |
|---|---|
| gattcgggc tgtacagttg caagccaagg cattccaacg aggtcctggg aaactttaca | 360 |
| gtcagagtga cagattcccc ttcgtcaggt gatgatgaag atgatgacga tgagtcagag | 420 |
| gatacaggtg tccccttctg gacccggcca gataagatgg agaagaagct gctggcagtt | 480 |
| cctgccgcca acaccgttcg cttccgatgt ccagcaggtg gaaacccaac tcccaccatt | 540 |
| tactggctga agaatggcaa agaattcaag ggagagcaca ggatcggggg catcaagttg | 600 |
| cgacaccagc agtggagctt ggtgatggag agcgttgtgc cgtcagatcg aggaaactac | 660 |
| acctgtgttg tggagaacaa atatggcaat attaggcaca cataccagct tgatgtttta | 720 |
| gaacggtcac cccaccgacc aatcctgcaa gcaggactcc ctgccaatca gactgtggtg | 780 |
| gtcgggagca atgtggaatt tcactgcaag gtctacagcg atgcccagcc tcatatccag | 840 |
| tggctgaaac acgtagaagt caacggcagc aagtatggac ctgatgggac accctatgtc | 900 |
| acagtgctga agacggcagg tgttaacaca acggataagg agctagagat tctgtacttg | 960 |
| cgaaatgtta cttttgagga tgctggggaa tatacttgtc tcgcagggaa ttctattggg | 1020 |
| ttctcacatc actctgcttg gctgacggtg ctaccagcag aggagctgat ggaaatggat | 1080 |
| gattcgggct cagtgtacgc tggcattctc agctatggca ctggcttagt cctcttcatc | 1140 |
| ctggtgctgg tcattgtgat tatctgcagg atgaaaatgc caaacaaaaa ggccatgaac | 1200 |
| accaccactg tacagaaagt ctccaaattt ccactcaaga cacagcaggt gtcgttggag | 1260 |
| tccaactctt ccatgaattc aacacacccc tggtccgga tcactcgtct ctcctccagc | 1320 |
| gatgggccga tgctggccaa cgtctctgag ctggaacttc ctccagatcc caagtgggaa | 1380 |
| ttggcacgtt ctcgcctgac cctggggaag ccgcttggtg agggctgttt tggccaagtg | 1440 |
| gtgatgcgg aagcaattgg gattgataaa gacaagccaa acaaggccat caccgtggct | 1500 |
| gtcaagatgt taaaagatga tgccacagac aaggacctt cagacctggt ctctgagatg | 1560 |
| gaaatgatga aatgattgg gaagcacaaa aacatcatta acctgctcgg tgcttgcacg | 1620 |
| caggacggac cgctctacgt gttggttgaa tatgcatcga aggggaactt gcgggaatac | 1680 |
| ctcagggcac gtcgcccacc tggcatggac tattccttcg acacctgcaa gctgcccgag | 1740 |
| gagcagttga catttaaaga cctggttccc tgcgcctacc aggtggcccg gggcatggag | 1800 |
| tacttggcgt cacagaaatg cattcatcgt gacttggcag ccaggaatgt gttagtcact | 1860 |
| gaggacaatg tgatgaaaat agctgatttt ggccttgcta gagacgttca caacatcgac | 1920 |
| tattacaaga aaaccaccaa tggtcggctg cctgtgaaat ggatggctcc agaagcattg | 1980 |
| tttgaccggg tctatactca ccagagcgat gtctggtctt tggagtgct actatgggag | 2040 |
| atcttcactt tgggagggtc tccgtacccg ggaattcctg ttgaagaact cttcaaactc | 2100 |
| ttgaaagaag gccatcggat ggataaaccc gccaactgta cccacgacct gtacatgatc | 2160 |
| atgcgggagt gctggcacgc tgtcccctcg cagcgaccca cattcaagca gctggtggaa | 2220 |
| gacctggaca gagtcctcac catgacatcc actgatgagt acctggacct ctcggtgccc | 2280 |
| tttgagcaat actcacccgc tggccaggac acccacagca cctgctcctc aggggacgac | 2340 |
| tcggtttttg cacatgacct gctgcctgat gagccctgcc tgcccaagca cgtgccctgt | 2400 |
| aatggcgtca tccgcacgtg a | 2421 |

<210> SEQ ID NO 20
<211> LENGTH: 806
<212> TYPE: PRT
<213> ORGANISM: Gallus gallus

<400> SEQUENCE: 20

-continued

```
Met Arg Ala Ala Trp Gly Ser Val Trp Cys Leu Cys Leu Ala Ala Ala
1               5                   10                  15

Val Gly Ala Leu Pro Ala Arg Arg Arg Gly Ala Glu Arg Ser Gly
            20                  25                  30

Gly Gln Ala Ala Glu Tyr Leu Arg Ser Glu Thr Ala Phe Leu Glu Glu
        35                  40                  45

Leu Val Phe Gly Ser Gly Asp Thr Ile Glu Leu Ser Cys Asn Thr Gln
    50                  55                  60

Ser Ser Ser Val Ser Val Phe Trp Phe Lys Asp Gly Ile Gly Ile Ala
65                  70                  75                  80

Pro Ser Asn Arg Thr His Ile Gly Gln Lys Leu Leu Lys Ile Ile Asn
                85                  90                  95

Val Ser Tyr Asp Asp Ser Gly Leu Tyr Ser Cys Lys Pro Arg His Ser
            100                 105                 110

Asn Glu Val Leu Gly Asn Phe Thr Val Arg Val Thr Asp Ser Pro Ser
        115                 120                 125

Ser Gly Asp Asp Glu Asp Asp Asp Glu Ser Glu Asp Thr Gly Val
    130                 135                 140

Pro Phe Trp Thr Arg Pro Asp Lys Met Glu Lys Lys Leu Leu Ala Val
145                 150                 155                 160

Pro Ala Ala Asn Thr Val Arg Phe Arg Cys Pro Ala Gly Gly Asn Pro
                165                 170                 175

Thr Pro Thr Ile Tyr Trp Leu Lys Asn Gly Lys Glu Phe Lys Gly Glu
            180                 185                 190

His Arg Ile Gly Gly Ile Lys Leu Arg His Gln Gln Trp Ser Leu Val
        195                 200                 205

Met Glu Ser Val Val Pro Ser Asp Arg Gly Asn Tyr Thr Cys Val Val
    210                 215                 220

Glu Asn Lys Tyr Gly Asn Ile Arg His Thr Tyr Gln Leu Asp Val Leu
225                 230                 235                 240

Glu Arg Ser Pro His Arg Pro Ile Leu Gln Ala Gly Leu Pro Ala Asn
                245                 250                 255

Gln Thr Val Val Val Gly Ser Asn Val Glu Phe His Cys Lys Val Tyr
            260                 265                 270

Ser Asp Ala Gln Pro His Ile Gln Trp Leu Lys His Val Glu Val Asn
        275                 280                 285

Gly Ser Lys Tyr Gly Pro Asp Gly Thr Pro Tyr Val Thr Val Leu Lys
    290                 295                 300

Thr Ala Gly Val Asn Thr Thr Asp Lys Glu Leu Glu Ile Leu Tyr Leu
305                 310                 315                 320

Arg Asn Val Thr Phe Glu Asp Ala Gly Glu Tyr Thr Cys Leu Ala Gly
                325                 330                 335

Asn Ser Ile Gly Phe Ser His His Ser Ala Trp Leu Thr Val Leu Pro
            340                 345                 350

Ala Glu Glu Leu Met Glu Met Asp Asp Ser Gly Ser Val Tyr Ala Gly
        355                 360                 365

Ile Leu Ser Tyr Gly Thr Gly Leu Val Leu Phe Ile Leu Val Leu Val
    370                 375                 380

Ile Val Ile Ile Cys Arg Met Lys Met Pro Asn Lys Lys Ala Met Asn
385                 390                 395                 400

Thr Thr Thr Val Gln Lys Val Ser Lys Phe Pro Leu Lys Arg Gln Gln
                405                 410                 415
```

```
Val Ser Leu Glu Ser Asn Ser Ser Met Asn Ser Asn Thr Pro Leu Val
            420                 425                 430

Arg Ile Thr Arg Leu Ser Ser Ser Asp Gly Pro Met Leu Ala Asn Val
            435                 440                 445

Ser Glu Leu Glu Leu Pro Pro Asp Pro Lys Trp Glu Leu Ala Arg Ser
450                 455                 460

Arg Leu Thr Leu Gly Lys Pro Leu Gly Glu Gly Cys Phe Gly Gln Val
465                 470                 475                 480

Val Met Ala Glu Ala Ile Gly Ile Asp Lys Asp Lys Pro Asn Lys Ala
                485                 490                 495

Ile Thr Val Ala Val Lys Met Leu Lys Asp Asp Ala Thr Asp Lys Asp
                500                 505                 510

Leu Ser Asp Leu Val Ser Glu Met Glu Met Met Lys Met Ile Gly Lys
            515                 520                 525

His Lys Asn Ile Ile Asn Leu Leu Gly Ala Cys Thr Gln Asp Gly Pro
            530                 535                 540

Leu Tyr Val Leu Val Glu Tyr Ala Ser Lys Gly Asn Leu Arg Glu Tyr
545                 550                 555                 560

Leu Arg Ala Arg Arg Pro Pro Gly Met Asp Tyr Ser Phe Asp Thr Cys
                565                 570                 575

Lys Leu Pro Glu Glu Gln Leu Thr Phe Lys Asp Leu Val Ser Cys Ala
            580                 585                 590

Tyr Gln Val Ala Arg Gly Met Glu Tyr Leu Ala Ser Gln Lys Cys Ile
            595                 600                 605

His Arg Asp Leu Ala Ala Arg Asn Val Leu Val Thr Glu Asp Asn Val
610                 615                 620

Met Lys Ile Ala Asp Phe Gly Leu Ala Arg Asp Val His Asn Ile Asp
625                 630                 635                 640

Tyr Tyr Lys Lys Thr Thr Asn Gly Arg Leu Pro Val Lys Trp Met Ala
                645                 650                 655

Pro Glu Ala Leu Phe Asp Arg Val Tyr Thr His Gln Ser Asp Val Trp
            660                 665                 670

Ser Phe Gly Val Leu Leu Trp Glu Ile Phe Thr Leu Gly Gly Ser Pro
            675                 680                 685

Tyr Pro Gly Ile Pro Val Glu Glu Leu Phe Lys Leu Leu Lys Glu Gly
690                 695                 700

His Arg Met Asp Lys Pro Ala Asn Cys Thr His Asp Leu Tyr Met Ile
705                 710                 715                 720

Met Arg Glu Cys Trp His Ala Val Pro Ser Gln Arg Pro Thr Phe Lys
                725                 730                 735

Gln Leu Val Glu Asp Leu Asp Arg Val Leu Thr Met Thr Ser Thr Asp
            740                 745                 750

Glu Tyr Leu Asp Leu Ser Val Pro Phe Glu Gln Tyr Ser Pro Ala Gly
            755                 760                 765

Gln Asp Thr His Ser Thr Cys Ser Ser Gly Asp Asp Ser Val Phe Ala
770                 775                 780

His Asp Leu Leu Pro Asp Glu Pro Cys Leu Pro Lys His Val Pro Cys
785                 790                 795                 800

Asn Gly Val Ile Arg Thr
                805
```

<210> SEQ ID NO 21
<211> LENGTH: 2484
<212> TYPE: DNA

<213> ORGANISM: Xenopus laevis

<400> SEQUENCE: 21

| | | | | | |
|---|---|---|---|---|---|
| atgtctaagg | ctggagggggg | ctgtggaatt | gcccttttatc | aagggatcca | tatgggaatt | 60 |
| gtcaccctgt | tctgcactct | ctgcttttt | ctggtctctg | tgaactgtgt | cccggctgcc | 120 |
| cgactgccag | ttacgctccc | tggagaggac | agagcaaaca | gaaaagcatc | agattatctc | 180 |
| acggtagaac | agcccccatt | cgatgagctc | atgtttacaa | ttggagaaac | cattgagttg | 240 |
| tcctgctctg | cggatgatgc | atccacgacc | accaagtggt | tcaaggatgg | tatcggcatt | 300 |
| gtgccgaaca | acagaacaag | tacgaggcag | ggcctgctga | agattatcaa | catctcatac | 360 |
| gatgactctg | ggatatacag | ttgcagacta | tggcattcta | ctgaaattct | gcgcaatttt | 420 |
| accatcagag | taacagactt | accatcgtcc | ggtgatgatg | aggatgacga | tgatgaaacc | 480 |
| gaagacagag | agcctcctcg | ctggacccaa | cctgagaaga | tggagaagaa | acttattgca | 540 |
| gtccctgccg | ctaacacaat | ccgattccgg | tgcccagccg | cggggaatcc | caccccctacc | 600 |
| atccattggc | ttaagaacgg | aaaggaattc | aggggagagc | atcgtattgg | tggcatcaaa | 660 |
| ctccgacatc | agcagtggag | cctcgttatg | gagagcgtag | ttccatcgga | taaaggcaac | 720 |
| tacacgtgtg | tagtggagaa | caaatatgga | agcatccgtc | aaacctatca | acttgatgtc | 780 |
| ctggagaggt | cctctcaccg | gcccatcctt | caggccgggt | tacccgccaa | ccagacggtg | 840 |
| gtgtttggga | gcgacgtgga | attccactgc | aaagtctaca | gtgacgcaca | gccacatatt | 900 |
| cagtggctta | aacacgtgga | agtgaatggc | agcaagtacg | gcccagacgg | agatccttac | 960 |
| gtcacagtgc | tgcaatcttt | caccaatggc | actgaagtcg | attctaccct | aagtctaaaa | 1020 |
| aatgtgaccg | agacccatga | aggacagtat | gtgtgtagag | ccaacaattt | cataggagta | 1080 |
| gccgaggcat | ccttttggct | ccacatttac | aaaccagcac | cagcagaacc | agtggagaag | 1140 |
| ccagcaacca | catcttccag | ctccatcacc | gttcttattg | tggtcacctc | gactattgtg | 1200 |
| ttcatactgt | tggttatcat | tgtcatcacc | taccgcatga | aggtcccttc | taagaaggca | 1260 |
| atgagcaccc | cgccggtgca | taaagtctcc | aagttcccgc | tcaagcggca | ggtgtctcta | 1320 |
| gagtccaact | cttctatgaa | ttccaacacc | ccgctggtga | ggatcactca | cctgtcctcc | 1380 |
| agcgacggaa | ccatgttggc | taatgtgtcg | gagctcggcc | tgcccctgga | tcccaagtgg | 1440 |
| gagttattga | gatcaaggct | gactttagga | aagcccttg | gagaaggctg | ctttggtcaa | 1500 |
| gtagtgatgg | cagaagcaat | tggcattgat | aaggaaaggc | caaataagcc | tgttactgta | 1560 |
| gctgtaaaga | tgcttaaaga | tgatgctaca | gataaagatc | tctccgatct | ggtctcggag | 1620 |
| atggagatga | tgaaaatgat | tgggaagcac | aaaaatatca | tcaatctgct | aggagcatgc | 1680 |
| actcaggatg | gaccactgta | cgttcttgtg | gaatatgcat | ccaaagggaa | cctcagggag | 1740 |
| tatttaaagg | cacggcgccc | cccaggaatg | gattattctt | ttgacacctg | caaaattcca | 1800 |
| gctgagcagc | tgacgttcaa | ggacctcgtt | tcttgcgcct | accaggtagc | tcgtggcatg | 1860 |
| gagtacctgg | cgtcgcaaaa | atgtattcac | agagatctgg | cagccagaaa | tgtgttagta | 1920 |
| acagatgaca | ttgtaatgaa | gattgcagat | ttcggcttgg | ccagggacat | ccacaacata | 1980 |
| gattattaca | agaaaacaac | aaatggtcgg | ctgccagtca | aatggatggc | tccggaagct | 2040 |
| ttgttcgacc | gtatctacac | tcatcagagc | gatgtatggt | cgtacggagt | gctgctgtgg | 2100 |
| gagatattta | cactgggggg | ctcgcccctac | ccagggatcc | cagtagagga | actctttaag | 2160 |
| ctattgaaag | aaggccacag | aatggacaag | ccagcaaact | gcacacatga | actgtatatg | 2220 |
| atcatgagag | agtgctggca | cgctgtccca | tcgcaaagac | caaccttcaa | gcagctggtt | 2280 |

-continued

```
gaagaccttg accgcgttct tactgtaaca tctactgatg agtacctgga cctgtcggta    2340
ccattcgagc agtattcccc ggcgggccaa gacagtaaca gcacctgctc ctcgggggac    2400
gactcagtct tgctcatga cattttaccc gatgaaccgt gtcttcccaa acaacagcag    2460
tacaacggcg ccatccgaac atga                                          2484
```

<210> SEQ ID NO 22
<211> LENGTH: 827
<212> TYPE: PRT
<213> ORGANISM: Xenopus laevis

<400> SEQUENCE: 22

```
Met Ser Lys Ala Gly Gly Gly Cys Gly Ile Ala Leu Tyr Gln Gly Ile
1               5                   10                  15

His Met Gly Ile Val Thr Leu Phe Cys Thr Leu Cys Phe Phe Leu Val
            20                  25                  30

Ser Val Asn Cys Val Pro Ala Ala Arg Leu Pro Val Thr Leu Pro Gly
        35                  40                  45

Glu Asp Arg Ala Asn Arg Lys Ala Ser Asp Tyr Leu Thr Val Glu Gln
    50                  55                  60

Pro Pro Phe Asp Glu Leu Met Phe Thr Ile Gly Thr Ile Glu Leu
65                  70                  75                  80

Ser Cys Ser Ala Asp Asp Ala Ser Thr Thr Lys Trp Phe Lys Asp
                85                  90                  95

Gly Ile Gly Ile Val Pro Asn Asn Arg Thr Ser Thr Arg Gln Gly Leu
            100                 105                 110

Leu Lys Ile Ile Asn Ile Ser Tyr Asp Asp Ser Gly Ile Tyr Ser Cys
        115                 120                 125

Arg Leu Trp His Ser Thr Glu Ile Leu Arg Asn Phe Thr Ile Arg Val
    130                 135                 140

Thr Asp Leu Pro Ser Ser Gly Asp Asp Glu Asp Asp Asp Glu Thr
145                 150                 155                 160

Glu Asp Arg Glu Pro Pro Arg Trp Thr Gln Pro Glu Lys Met Glu Lys
                165                 170                 175

Lys Leu Ile Ala Val Pro Ala Ala Asn Thr Ile Arg Phe Arg Cys Pro
            180                 185                 190

Ala Ala Gly Asn Pro Thr Pro Thr Ile His Trp Leu Lys Asn Gly Lys
        195                 200                 205

Glu Phe Arg Gly Glu His Arg Ile Gly Gly Ile Lys Leu Arg His Gln
    210                 215                 220

Gln Trp Ser Leu Val Met Glu Ser Val Val Pro Ser Asp Lys Gly Asn
225                 230                 235                 240

Tyr Thr Cys Val Val Glu Asn Lys Tyr Gly Ser Ile Arg Gln Thr Tyr
                245                 250                 255

Gln Leu Asp Val Leu Glu Arg Ser Ser His Arg Pro Ile Leu Gln Ala
            260                 265                 270

Gly Leu Pro Ala Asn Gln Thr Val Val Phe Gly Ser Asp Val Glu Phe
        275                 280                 285

His Cys Lys Val Tyr Ser Asp Ala Gln Pro His Ile Gln Trp Leu Lys
    290                 295                 300

His Val Glu Val Asn Gly Ser Lys Tyr Gly Pro Asp Gly Asp Pro Tyr
305                 310                 315                 320

Val Thr Val Leu Gln Ser Phe Thr Asn Gly Thr Glu Val Asp Ser Thr
                325                 330                 335
```

```
Leu Ser Leu Lys Asn Val Thr Glu Thr His Glu Gly Gln Tyr Val Cys
            340                 345                 350

Arg Ala Asn Asn Phe Ile Gly Val Ala Glu Ala Ser Phe Trp Leu His
            355                 360                 365

Ile Tyr Lys Pro Ala Pro Glu Pro Val Glu Lys Pro Ala Thr Thr
            370                 375                 380

Ser Ser Ser Ser Ile Thr Val Leu Ile Val Val Thr Ser Thr Ile Val
385                 390                 395                 400

Phe Ile Leu Leu Val Ile Ile Val Ile Thr Tyr Arg Met Lys Val Pro
                405                 410                 415

Ser Lys Lys Ala Met Ser Thr Pro Pro Val His Lys Val Ser Lys Phe
            420                 425                 430

Pro Leu Lys Arg Gln Val Ser Leu Glu Ser Asn Ser Ser Met Asn Ser
            435                 440                 445

Asn Thr Pro Leu Val Arg Ile Thr His Leu Ser Ser Ser Asp Gly Thr
            450                 455                 460

Met Leu Ala Asn Val Ser Glu Leu Gly Leu Pro Leu Asp Pro Lys Trp
465                 470                 475                 480

Glu Leu Leu Arg Ser Arg Leu Thr Leu Gly Lys Pro Leu Gly Glu Gly
                485                 490                 495

Cys Phe Gly Gln Val Val Met Ala Glu Ala Ile Gly Ile Asp Lys Glu
            500                 505                 510

Arg Pro Asn Lys Pro Val Thr Val Ala Val Lys Met Leu Lys Asp Asp
            515                 520                 525

Ala Thr Asp Lys Asp Leu Ser Asp Leu Val Ser Glu Met Glu Met Met
            530                 535                 540

Lys Met Ile Gly Lys His Lys Asn Ile Ile Asn Leu Leu Gly Ala Cys
545                 550                 555                 560

Thr Gln Asp Gly Pro Leu Tyr Val Leu Val Glu Tyr Ala Ser Lys Gly
                565                 570                 575

Asn Leu Arg Glu Tyr Leu Lys Ala Arg Arg Pro Pro Gly Met Asp Tyr
            580                 585                 590

Ser Phe Asp Thr Cys Lys Ile Pro Ala Glu Gln Leu Thr Phe Lys Asp
            595                 600                 605

Leu Val Ser Cys Ala Tyr Gln Val Ala Arg Gly Met Glu Tyr Leu Ala
            610                 615                 620

Ser Gln Lys Cys Ile His Arg Asp Leu Ala Ala Arg Asn Val Leu Val
625                 630                 635                 640

Thr Asp Asp Ile Val Met Lys Ile Ala Asp Phe Gly Leu Ala Arg Asp
                645                 650                 655

Ile His Asn Ile Asp Tyr Tyr Lys Lys Thr Thr Asn Gly Arg Leu Pro
            660                 665                 670

Val Lys Trp Met Ala Pro Glu Ala Leu Phe Asp Arg Ile Tyr Thr His
            675                 680                 685

Gln Ser Asp Val Trp Ser Tyr Gly Val Leu Leu Trp Glu Ile Phe Thr
            690                 695                 700

Leu Gly Gly Ser Pro Tyr Pro Gly Ile Pro Val Glu Glu Leu Phe Lys
705                 710                 715                 720

Leu Leu Lys Glu Gly His Arg Met Asp Lys Pro Ala Asn Cys Thr His
                725                 730                 735

Glu Leu Tyr Met Ile Met Arg Glu Cys Trp His Ala Val Pro Ser Gln
            740                 745                 750
```

-continued

```
Arg Pro Thr Phe Lys Gln Leu Val Glu Asp Leu Asp Arg Val Leu Thr
        755                 760                 765
Val Thr Ser Thr Asp Glu Tyr Leu Asp Leu Ser Val Pro Phe Glu Gln
    770                 775                 780
Tyr Ser Pro Ala Gly Gln Asp Ser Asn Ser Thr Cys Ser Ser Gly Asp
785                 790                 795                 800
Asp Ser Val Phe Ala His Asp Ile Leu Pro Asp Glu Pro Cys Leu Pro
                805                 810                 815
Lys Gln Gln Gln Tyr Asn Gly Ala Ile Arg Thr
            820                 825
```

<210> SEQ ID NO 23
<211> LENGTH: 2409
<212> TYPE: DNA
<213> ORGANISM: Xenopus laevis

<400> SEQUENCE: 23

| | | | | | |
|---|---|---|---|---|---|
| atggtctctg | tgaatggtgt | cccggctgcc | cgactgccag | ttacgctccc | tggagaggac | 60 |
| agagcgagca | gaaaagcacc | agattatctc | atggtagaac | agcccccatt | cgatgaactc | 120 |
| atgtatacaa | ttggagaaac | cattgagttg | tcctgcgctg | cagaagatgc | ttccacaact | 180 |
| accaagtggt | gtaaggatgg | tattggcatt | gtaccgaaca | cagaacaag | cacaaggcag | 240 |
| ggcctgctga | agattatcaa | cgtctcctcc | gatgactccg | ggatatacag | ctgcagacta | 300 |
| tggcattcta | ccgagattct | gcgcaatttt | acaatcagag | taacagactt | gccatcatct | 360 |
| ggtgacgatg | aggatgatga | tgatgatgat | gatgatgaaa | ccgaagacag | agaacctcct | 420 |
| cgctggaccc | aacctgagag | gatggaaaag | aaacttattg | cagtccctgc | tgctaacaca | 480 |
| atccgcttcc | ggtgcccagc | cgcagggaat | cccaccccta | ccatccactg | gctaaagaac | 540 |
| ggaaaggagt | tcaggggga | acatcgtatt | ggtggcatca | aactccgaca | tcaacagtgg | 600 |
| agccttgtta | tggagagtgt | ggtcccatca | gataaaggca | actacacgtg | tgtggtggag | 660 |
| aacaaatatg | gaagcatccg | tcaaacctat | caacttgatg | tccttgagag | gtcctctcac | 720 |
| cggcccatcc | ttcaggctgg | gttacccggc | aaccagacgg | ttgtgcttgg | gagcgacgtg | 780 |
| gaattccact | gcaaagtcta | cagtgacgca | caacctcata | ttcagtggct | taaacacgtg | 840 |
| gaagtgaatg | gcagcaaata | cggcccagac | ggagatcctt | acgtctcagt | gttgcaatct | 900 |
| ttcatcaatg | gcactgaagt | cgattctacc | ctaagtctaa | aaaatgtgac | cgagaccaat | 960 |
| gaaggacagt | atgtgtgtag | agccaacaat | ttcataggag | tagccgaggc | atccttttgg | 1020 |
| ctccacattt | acaaaccagc | accagcagaa | ccagtggaga | aggcattgac | aacatcttcc | 1080 |
| agctctatca | ccgtccttat | tgtggtcacc | tcgaccattg | tgttcatact | gttggttatc | 1140 |
| atcgtcatca | cccacctcat | gaaggtccct | tccaagaagt | caatgaccgc | ccaccggtg | 1200 |
| cataaagtct | ccaagttccc | cctcaaacgg | cagcaggtgt | ctctagagtc | caactcttct | 1260 |
| atgaattcca | cacccccgtt | ggtgaggatc | actcatctgt | cctccagcga | tggaaccatg | 1320 |
| ctggctaatg | tgtcggaact | tggcctgcca | cttgacccca | gtgggagtt | attgagatca | 1380 |
| aggctgactt | taggaaagcc | cctcggggaa | ggctgcttcg | gtcaggtggt | gatggcagaa | 1440 |
| gctattggca | ttgataagga | aaggccaaat | aagcctgcta | ctgtagctgt | aaagatgctt | 1500 |
| aaagacgatg | ccacagataa | agatctctca | gatctggtct | ctgagatgga | gatgatgaaa | 1560 |
| atgattggga | agcataaaaa | tatcatcaat | ctgctgggag | catgcactca | ggatgggccg | 1620 |
| ctgtacgttc | tggtggaata | cgcatcgaaa | gggagcctca | gggagtattt | aaaggcacgg | 1680 |

-continued

```
cgccccccag gaatggatta ttcttttgat gcctgcaaaa ttccagctga gcagctgacg    1740
ttcaaggacc tagtttcttg tgcctaccag gtagctcgtg gcatggagta cctggcatca    1800
caaaaatgca ttcacagaga tctggcagcc agaaatgtgt tagtaacaga tgacaacgta    1860
atgaagattg cagatttcgg cttggccagg gacatccaca acatagatta ttacaagaaa    1920
acaacaaatg gtcggctgcc tgtgaaatgg atggctccgg aagctttgtt tgaccgtatc    1980
tacactcatc acagcgatgt atggtcgtac ggagtgctgc tgtgggagat atttacactg    2040
gggggctcac cctacccagg atcccggta gaggaacttt ttaagctatt gaaagaaggc     2100
cacagaatgg acaagccagc aaactgcaca catgaactgt atatgatcat gagagagtgc    2160
tggcacgctg tccctcaca aagacccgcc ttcaagcagc tggttgaaga ccttgaccgc     2220
gttcttactg taacatctac taatgagtac ctagacctct cggtagcatt cgagcagtat    2280
tctccaccca gccaagacag tcacagcacc tgctcctcag ggacgactc agtctttgct     2340 cacgacattt tacccgatga accgtgtctt cccaaacacc agcagcacaa cggcgccatc    2400
cccacatga                                                            2409

<210> SEQ ID NO 24
<211> LENGTH: 802
<212> TYPE: PRT
<213> ORGANISM: Xenopus laevis

<400> SEQUENCE: 24

Met Val Ser Val Asn Gly Val Pro Ala Ala Arg Leu Pro Val Thr Leu
1               5                   10                  15

Pro Gly Glu Asp Arg Ala Ser Arg Lys Ala Pro Asp Tyr Leu Met Val
                20                  25                  30

Glu Gln Pro Pro Phe Asp Glu Leu Met Tyr Thr Ile Gly Glu Thr Ile
            35                  40                  45

Glu Leu Ser Cys Ala Ala Glu Asp Ala Ser Thr Thr Thr Lys Trp Cys
        50                  55                  60

Lys Asp Gly Ile Gly Ile Val Pro Asn Asn Arg Thr Ser Thr Arg Gln
65                  70                  75                  80

Gly Leu Leu Lys Ile Ile Asn Val Ser Ser Asp Ser Gly Ile Tyr
                85                  90                  95

Ser Cys Arg Leu Trp His Ser Thr Glu Ile Leu Arg Asn Phe Thr Ile
            100                 105                 110

Arg Val Thr Asp Leu Pro Ser Ser Gly Asp Asp Glu Asp Asp Asp Asp
        115                 120                 125

Asp Asp Asp Asp Glu Thr Glu Asp Arg Glu Pro Pro Arg Trp Thr Gln
130                 135                 140

Pro Glu Arg Met Glu Lys Lys Leu Ile Ala Val Pro Ala Ala Asn Thr
145                 150                 155                 160

Ile Arg Phe Arg Cys Pro Ala Ala Gly Asn Pro Thr Pro Thr Ile His
                165                 170                 175

Trp Leu Lys Asn Gly Lys Glu Phe Arg Gly Glu His Arg Ile Gly Gly
            180                 185                 190

Ile Lys Leu Arg His Gln Gln Trp Ser Leu Val Met Glu Ser Val Val
        195                 200                 205

Pro Ser Asp Lys Gly Asn Tyr Thr Cys Val Val Glu Asn Lys Tyr Gly
    210                 215                 220

Ser Ile Arg Gln Thr Tyr Gln Leu Asp Val Leu Glu Arg Ser Ser His
225                 230                 235                 240
```

```
Arg Pro Ile Leu Gln Ala Gly Leu Pro Gly Asn Gln Thr Val Val Leu
                245                 250                 255

Gly Ser Asp Val Glu Phe His Cys Lys Val Tyr Ser Asp Ala Gln Pro
            260                 265                 270

His Ile Gln Trp Leu Lys His Val Glu Val Asn Gly Ser Lys Tyr Gly
        275                 280                 285

Pro Asp Gly Asp Pro Tyr Val Ser Val Leu Gln Ser Phe Ile Asn Gly
    290                 295                 300

Thr Glu Val Asp Ser Thr Leu Ser Leu Lys Asn Val Thr Glu Thr Asn
305                 310                 315                 320

Glu Gly Gln Tyr Val Cys Arg Ala Asn Asn Phe Ile Gly Val Ala Glu
                325                 330                 335

Ala Ser Phe Trp Leu His Ile Tyr Lys Pro Ala Pro Ala Glu Pro Val
            340                 345                 350

Glu Lys Ala Leu Thr Thr Ser Ser Ser Ile Thr Val Leu Ile Val
        355                 360                 365

Val Thr Ser Thr Ile Val Phe Ile Leu Leu Val Ile Ile Val Ile Thr
    370                 375                 380

His Leu Met Lys Val Pro Ser Lys Lys Ser Met Thr Ala Pro Pro Val
385                 390                 395                 400

His Lys Val Ser Lys Phe Pro Leu Lys Arg Gln Gln Val Ser Leu Glu
                405                 410                 415

Ser Asn Ser Ser Met Asn Ser Asn Thr Pro Leu Val Arg Ile Thr His
            420                 425                 430

Leu Ser Ser Ser Asp Gly Thr Met Leu Ala Asn Val Ser Glu Leu Gly
        435                 440                 445

Leu Pro Leu Asp Pro Lys Trp Glu Leu Leu Arg Ser Arg Leu Thr Leu
    450                 455                 460

Gly Lys Pro Leu Gly Glu Gly Cys Phe Gly Gln Val Val Met Ala Glu
465                 470                 475                 480

Ala Ile Gly Ile Asp Lys Glu Arg Pro Asn Lys Pro Ala Thr Val Ala
                485                 490                 495

Val Lys Met Leu Lys Asp Asp Ala Thr Asp Lys Asp Leu Ser Asp Leu
            500                 505                 510

Val Ser Glu Met Glu Met Met Lys Met Ile Gly Lys His Lys Asn Ile
        515                 520                 525

Ile Asn Leu Leu Gly Ala Cys Thr Gln Asp Gly Pro Leu Tyr Val Leu
    530                 535                 540

Val Glu Tyr Ala Ser Lys Gly Ser Leu Arg Glu Tyr Leu Lys Ala Arg
545                 550                 555                 560

Arg Pro Pro Gly Met Asp Tyr Ser Phe Asp Ala Cys Lys Ile Pro Ala
                565                 570                 575

Glu Gln Leu Thr Phe Lys Asp Leu Val Ser Cys Ala Tyr Gln Val Ala
            580                 585                 590

Arg Gly Met Glu Tyr Leu Ala Ser Gln Lys Cys Ile His Arg Asp Leu
        595                 600                 605

Ala Ala Arg Asn Val Leu Val Thr Asp Asp Asn Val Met Lys Ile Ala
    610                 615                 620

Asp Phe Gly Leu Ala Arg Asp Ile His Asn Ile Asp Tyr Tyr Lys Lys
625                 630                 635                 640

Thr Thr Asn Gly Arg Leu Pro Val Lys Trp Met Ala Pro Glu Ala Leu
                645                 650                 655

Phe Asp Arg Ile Tyr Thr His His Ser Asp Val Trp Ser Tyr Gly Val
```

```
                    660                 665                 670
Leu Leu Trp Glu Ile Phe Thr Leu Gly Gly Ser Pro Tyr Pro Gly Ile
            675                 680                 685

Pro Val Glu Glu Leu Phe Lys Leu Leu Lys Glu Gly His Arg Met Asp
        690                 695                 700

Lys Pro Ala Asn Cys Thr His Glu Leu Tyr Met Ile Met Arg Glu Cys
705                 710                 715                 720

Trp His Ala Val Pro Ser Gln Arg Pro Ala Phe Lys Gln Leu Val Glu
                725                 730                 735

Asp Leu Asp Arg Val Leu Thr Val Thr Ser Thr Asn Glu Tyr Leu Asp
            740                 745                 750

Leu Ser Val Ala Phe Glu Gln Tyr Ser Pro Pro Ser Gln Asp Ser His
        755                 760                 765

Ser Thr Cys Ser Ser Gly Asp Asp Ser Val Phe Ala His Asp Ile Leu
    770                 775                 780

Pro Asp Glu Pro Cys Leu Pro Lys His Gln Gln His Asn Gly Ala Ile
785                 790                 795                 800

Pro Thr

<210> SEQ ID NO 25
<211> LENGTH: 2391
<212> TYPE: DNA
<213> ORGANISM: Pleurodeles waltlii

<400> SEQUENCE: 25
atgctcgtct ggctctgcgg cttgtgtctg gtgactctgg cgggcggacg ttcggcggcc      60
aggctgcccc tcaccgaggg ccgacccaca gcagacttcc tgcccggcga cgcctccctg     120
gtggaagagc tcctgttcgg cacgggggac accatcgagc tctcctgcac caccccgggc     180
tcctctgtgt ccgtggtgtg gttcaaagac gggatctcgg tggacccacc aacctggtcc     240
cacaccggcc agaagctgct gaagatcatc aacgtgtcct acgacgactc gggagtgtac     300
agctgcaagg cccggcagtc cagcgaggtg ctccggaacg tgaccgtcag ggtgaccgat     360
tctccgtcat ccggtgatga cgaagatgat gatgaggaat ctgaaagtgc aaatgcacca     420
aaattcacgc gaccggaatg gatggagaag aaactgcttg cagtgcccgc agccaacacg     480
gtgcgcttcc gatgcccagc tgcaggaaag ccaacgccat ccatcacttg gctgaaaaac     540
ggcaaggagt tcaaaggcga gcatcggatt gggggcataa agctaagaca ccagcagtgg     600
agtttggtga tggagagtgt agtcccatcc gatcggggaa attacacatg tgtggtggca     660
aacaagtacg gcaccatccg agagacctac acattggatg tccttgaacg aactcctcac     720
cggcccatcc tccaggcggg attccgttcc aacaagactg tggtgtagg aagcgatgtg     780
gagttccatt gcaaggtata cagtgatgct cagccgcaca tccagtggct gaaacacgtg     840
gaggttaatg gcagcaagtt tggacctgat gggaacccgt atgtcacagt gcttaagacg     900
gcaggtgtta atacctcgga taaggagcta gaaattcagt tcttgcgaaa tgtaactttt     960
gaggatgctg gggagtatac ttgtctcgct gggaactcta ttggctattc ccatcattct    1020
gcttggctca cggtgctgcc accagcagag ccggtcccag acgtcgacac ctctgtcagc    1080
attcttgccg ctgcaggatg tgtcgcagtt gttatactgg tggtgatcat aatctttact    1140
tacaagatga agatgccctc caagaagacc atgaacaccg ccactgtgca aaagtctca     1200
aagttccctc tcaagagaca ggtgtcactg gagtccaact cttcaatgaa ttccaacacc    1260
cctctggtgc gaatcacccg cctgtcgtcc agcgatggtc cgatgctggc caacgtgtcc    1320
```

-continued

```
gagctggagc tacccgctga tccgaagtgg gaattgtctc gttcacgctt gactttgggc    1380
aaacctcttg gggaaggatg ctttggccag gtggtgatgg cggatgcagt tggcattgaa    1440
aaggataagc caaacaaggc cacctcggtt gccgttaaga tgttgaaaga tgatgccact    1500
gataaagacc tgtcggatct agtctctgaa atggaaatga tgaaaatgat tgggaagcac    1560
aaaaacatca ttaatctcct gggagcctgc acgcaggatg cccactcta cgtgctggtg    1620 gaatatgcat ccaaaggaaa cttgcgggag tacctgaggg cccggcgccc tcctggcatg    1680
gattactcct tcgacacctg caaacttccc gaagagcagt tgaccttcaa ggacttggta    1740
tcctgtgcct accaggtggc ccgcggcatg gagtacctgg cctctcagaa gtgcatacac    1800
cgagatctgg cagcccggaa cgtgctggtg acggatgaca acgttatgaa gattgctgat    1860
tttggcctgg cgagagatgt gcacaacatc gactactaca agaaaactac aaatggccga    1920
ctgcccgtga gtggatggc tccggaggct tgttcgacc gggtctacac tcaccaaagc      1980
gacgtctggt cgtttggagt gcttctgtgg gagatcttca cgctgggggg ctcgccgtac    2040
cctggaatcc cagtgaaga actcttcaag ctgttaaagg aaggccatcg aatggacaaa     2100
ccagcgaact gcacgcatga gctgtacatg atcatgcggg agtgctggca tgcagtgcca    2160
tcccagcggc caaccttcaa gcaactcgta gaagacttgg accgggtcct tacggtgacc    2220
tccactgatg agtacctcga tctctctgtg cccttcgagc agtattcgcc tgcctgccca    2280
gacagccaca gcagctgctc ttctggagac gattcggtct ttgcccacga cctgcccgag    2340
gagccctgcc ttccgaagca ccagcagtac aatggagtaa tccgaacatg a             2391
```

<210> SEQ ID NO 26
<211> LENGTH: 796
<212> TYPE: PRT
<213> ORGANISM: Pleurodeles waltlii

<400> SEQUENCE: 26

```
Met Leu Val Trp Leu Cys Gly Leu Cys Leu Val Thr Leu Ala Gly Gly
1               5                   10                  15

Arg Ser Ala Ala Arg Leu Pro Leu Thr Glu Gly Arg Pro Thr Ala Asp
            20                  25                  30

Phe Leu Pro Gly Asp Ala Ser Leu Val Glu Glu Leu Leu Phe Gly Thr
        35                  40                  45

Gly Asp Thr Ile Glu Leu Ser Cys Thr Thr Pro Gly Ser Ser Val Ser
    50                  55                  60

Val Val Trp Phe Lys Asp Gly Ile Ser Val Asp Pro Pro Thr Trp Ser
65                  70                  75                  80

His Thr Gly Gln Lys Leu Leu Lys Ile Ile Asn Val Ser Tyr Asp Asp
                85                  90                  95

Ser Gly Val Tyr Ser Cys Lys Ala Arg Gln Ser Ser Glu Val Leu Arg
            100                 105                 110

Asn Val Thr Val Arg Val Thr Asp Ser Pro Ser Ser Gly Asp Asp Glu
        115                 120                 125

Asp Asp Asp Glu Glu Ser Glu Ser Ala Asn Ala Pro Lys Phe Thr Arg
    130                 135                 140

Pro Glu Trp Met Glu Lys Lys Leu Leu Ala Val Pro Ala Ala Asn Thr
145                 150                 155                 160

Val Arg Phe Arg Cys Pro Ala Ala Gly Lys Pro Thr Pro Ser Ile Thr
                165                 170                 175

Trp Leu Lys Asn Gly Lys Glu Phe Lys Gly Glu His Arg Ile Gly Gly
```

```
                180             185             190
Ile Lys Leu Arg His Gln Gln Trp Ser Leu Val Met Glu Ser Val Val
        195                 200                 205
Pro Ser Asp Arg Gly Asn Tyr Thr Cys Val Val Ala Asn Lys Tyr Gly
        210                 215                 220
Thr Ile Arg Glu Thr Tyr Thr Leu Asp Val Leu Glu Arg Thr Pro His
225                 230                 235                 240
Arg Pro Ile Leu Gln Ala Gly Phe Arg Ser Asn Lys Thr Val Val Val
                245                 250                 255
Gly Ser Asp Val Glu Phe His Cys Lys Val Tyr Ser Asp Ala Gln Pro
        260                 265                 270
His Ile Gln Trp Leu Lys His Val Glu Val Asn Gly Ser Lys Phe Gly
        275                 280                 285
Pro Asp Gly Asn Pro Tyr Val Thr Val Leu Lys Thr Ala Gly Val Asn
        290                 295                 300
Thr Ser Asp Lys Glu Leu Glu Ile Gln Phe Leu Arg Asn Val Thr Phe
305                 310                 315                 320
Glu Asp Ala Gly Glu Tyr Thr Cys Leu Ala Gly Asn Ser Ile Gly Tyr
                325                 330                 335
Ser His His Ser Ala Trp Leu Thr Val Leu Pro Pro Ala Glu Pro Val
                340                 345                 350
Pro Asp Val Asp Thr Ser Val Ser Ile Leu Ala Ala Ala Gly Cys Val
        355                 360                 365
Ala Val Val Ile Leu Val Val Ile Ile Ile Phe Thr Tyr Lys Met Lys
        370                 375                 380
Met Pro Ser Lys Lys Thr Met Asn Thr Ala Thr Val His Lys Val Ser
385                 390                 395                 400
Lys Phe Pro Leu Lys Arg Gln Val Ser Leu Glu Ser Asn Ser Ser Met
                405                 410                 415
Asn Ser Asn Thr Pro Leu Val Arg Ile Thr Arg Leu Ser Ser Ser Asp
                420                 425                 430
Gly Pro Met Leu Ala Asn Val Ser Glu Leu Glu Leu Pro Ala Asp Pro
        435                 440                 445
Lys Trp Glu Leu Ser Arg Ser Arg Leu Thr Leu Gly Lys Pro Leu Gly
        450                 455                 460
Glu Gly Cys Phe Gly Gln Val Val Met Ala Asp Ala Val Gly Ile Glu
465                 470                 475                 480
Lys Asp Lys Pro Asn Lys Ala Thr Ser Val Ala Val Lys Met Leu Lys
                485                 490                 495
Asp Asp Ala Thr Asp Lys Asp Leu Ser Asp Leu Val Ser Glu Met Glu
                500                 505                 510
Met Met Lys Met Ile Gly Lys His Lys Asn Ile Ile Asn Leu Leu Gly
        515                 520                 525
Ala Cys Thr Gln Asp Gly Pro Leu Tyr Val Leu Val Glu Tyr Ala Ser
        530                 535                 540
Lys Gly Asn Leu Arg Glu Tyr Leu Arg Ala Arg Arg Pro Pro Gly Met
545                 550                 555                 560
Asp Tyr Ser Phe Asp Thr Cys Lys Leu Pro Glu Glu Gln Leu Thr Phe
                565                 570                 575
Lys Asp Leu Val Ser Cys Ala Tyr Gln Val Ala Arg Gly Met Glu Tyr
                580                 585                 590
Leu Ala Ser Gln Lys Cys Ile His Arg Asp Leu Ala Ala Arg Asn Val
        595                 600                 605
```

-continued

```
Leu Val Thr Asp Asp Asn Val Met Lys Ile Ala Asp Phe Gly Leu Ala
        610                 615                 620

Arg Asp Val His Asn Ile Asp Tyr Tyr Lys Lys Thr Thr Asn Gly Arg
625                 630                 635                 640

Leu Pro Val Lys Trp Met Ala Pro Glu Ala Leu Phe Asp Arg Val Tyr
                645                 650                 655

Thr His Gln Ser Asp Val Trp Ser Phe Gly Val Leu Leu Trp Glu Ile
            660                 665                 670

Phe Thr Leu Gly Gly Ser Pro Tyr Pro Gly Ile Pro Val Glu Glu Leu
        675                 680                 685

Phe Lys Leu Leu Lys Glu Gly His Arg Met Asp Lys Pro Ala Asn Cys
    690                 695                 700

Thr His Glu Leu Tyr Met Ile Met Arg Glu Cys Trp His Ala Val Pro
705                 710                 715                 720

Ser Gln Arg Pro Thr Phe Lys Gln Leu Val Glu Asp Leu Asp Arg Val
                725                 730                 735

Leu Thr Val Thr Ser Thr Asp Glu Tyr Leu Asp Leu Ser Val Pro Phe
            740                 745                 750

Glu Gln Tyr Ser Pro Ala Cys Pro Asp Ser His Ser Ser Cys Ser Ser
        755                 760                 765

Gly Asp Asp Ser Val Phe Ala His Asp Leu Pro Glu Glu Pro Cys Leu
    770                 775                 780

Pro Lys His Gln Gln Tyr Asn Gly Val Ile Arg Thr
785                 790                 795
```

<210> SEQ ID NO 27
<211> LENGTH: 2403
<212> TYPE: DNA
<213> ORGANISM: Danio rerio

<400> SEQUENCE: 27

| | | |
|---|---|---|
| atggtcccac tctgtctcct cctgtacctc gcaaccctcg tcttcccacc agtgtacagt | 60 |
| gcacacctgc tgtccccaga gcccacagac tgggtatcga gtgaggtgga agtgtttctg | 120 |
| gaggactatg tggcgggagt cggggataca gtagttctgt cctgcacgcc gcaagacttt | 180 |
| ctccttccca tcgtatggca aaaagacgga gacgccgttt cttcaagcaa ccgtacacga | 240 |
| gtgggccaga aagccctccg catcatcaat gtctcctatg aagactcggg tgtttactcc | 300 |
| tgcagacatg cccacaagag catgcttctg agcaactaca ccgtcaaagt catcgattcg | 360 |
| ctgtcctctg gtgatgatga ggactatgat gaagatgagg acgaggcagg taatggaaat | 420 |
| gcagaagctc catactggac ccgttcggac cggatggaga gaaactatt ggctgttcct | 480 |
| gctgccaata cagtcaagtt ccgctgtcct gctgctggca acccaacgcc cagtatccat | 540 |
| tggctgaaaa atggcaagga gttcaaggga gagcagagaa tgggcggcat taagctgagg | 600 |
| catcagcagt ggagcttggt catggagagt gccgttccat ccgaccgggg aaattacaca | 660 |
| tgtgtggtgc agaacaaata cgggtcaatc aagcacactt atcaactcga tgtgctggag | 720 |
| cgctccccct accggcccat cttacaggca ggactgccag ccaatcagac ggtagtggtg | 780 |
| ggcagtgatg tggagttcca ctgtaaggtg tacagtgatg ctcagccaca catccagtgg | 840 |
| ctgaaacaca ttgaagtcaa tggaagccaa tatgggccca tggcgccccc ctacgtcaat | 900 |
| gttcttaaga ctgctgggat aaatactacg gataaagagc tggagattct ctacctgacc | 960 |
| aatgtgtctt tcgaggatgc ggggcaatac acttgtctgg cagggaactc gattggctat | 1020 |

-continued

```
aaccatcact ctgcttggct tacagtctta ccagcggtgg agatggagag agaggatgat    1080
tatgcagaca tcctcatcta tgtgacaagc tgcgtgctct tcattctcac catggtcatc    1140
attattctct gccgaatgtg gataaacacg cagaagactc tcccggcacc acctgttcaa    1200
aaactgtcca aattccccct caagagacag gtgtccttgg aatccaactc ttccatgaat    1260
tcaaacaccc cgctggtcag gatcgcccgc ctgtcatcca gcgatgggcc gatgttgcct    1320
aacgtgtctg aacttgaact gccctctgac cccaagtggg agtttactcg aacaaagtta    1380
acgttgggga aaccgttggg agagggctgc tttgggcagg tggtgatggc tgaagccatt    1440
gggattgaca agaaaaaacc caacaaacct ctaactgttg ctgtcaagat gctcaaagat    1500
gacggcacag ataaagacct gtcagacctt gtgtctgaaa tggagatgat gaagatgatt    1560
gggaaacata agaacatcat taacttgctg ggagcatgta ctcaagacgg tcctctgtac    1620
gtgctggtag aatacgcctc taagggaat cttagggaat acttacgagc cagaaggcca    1680
cctgggatgg actactcatt cgacacctgt aagatcccga acgaaacgct aacatttaaa    1740
gacctggtgt cctgcgccta tcaggtcgcc aggggtatgg agtacctggc ctcaaagaag    1800
tgtatccata gggaccccgc agcccggaat gttctggtta ccgaggacaa cgtgatgaag    1860
attgcagact tcggccttgc cagagatgtg cacaacattg actactacaa gaagaccacc    1920
aacggtcgtc tgcccgtcaa atggatggca ccagaagcac tgttcgatcg cgtctacacg    1980
caccagagcg atgtgtggtc ttatggtgtg ttgttgtggg agattttcac tcttggtgga    2040
tccccgtatc caggtatccc agtggaggag ctctttaaac tgctgaagga aggccatcgg    2100
atggacaaac cggccaactg cactcatgaa ctgtacatga tcatgcgaga atgttggcat    2160
gctgttcctt cacaaagacc cacgttcaga cagctggtgg aggaccacga cagggttctt    2220
tccatgacct ccactgacga gtacctggac ctctctgtac cgttcgagca gtattcaccg    2280
acctgtccgg actccaacag cacctgttcc tctggcgatg actctgtgtt tgcccacgac    2340
cccttacctg aggagccatg cctccctaaa caccaccaca gcaacgggt catacgaaca    2400 taa                                                                    2403
```

<210> SEQ ID NO 28
<211> LENGTH: 800
<212> TYPE: PRT
<213> ORGANISM: Danio rerio

<400> SEQUENCE: 28

```
Met Val Pro Leu Cys Leu Leu Tyr Leu Ala Thr Leu Val Phe Pro
1               5                  10                  15

Pro Val Tyr Ser Ala His Leu Leu Ser Pro Glu Pro Thr Asp Trp Val
                20                  25                  30

Ser Ser Glu Val Glu Val Phe Leu Glu Asp Tyr Val Ala Gly Val Gly
            35                  40                  45

Asp Thr Val Val Leu Ser Cys Thr Pro Gln Asp Phe Leu Leu Pro Ile
        50                  55                  60

Val Trp Gln Lys Asp Gly Asp Ala Val Ser Ser Ser Asn Arg Thr Arg
65                  70                  75                  80

Val Gly Gln Lys Ala Leu Arg Ile Ile Asn Val Ser Tyr Glu Asp Ser
                85                  90                  95

Gly Val Tyr Ser Cys Arg His Ala His Lys Ser Met Leu Leu Ser Asn
            100                 105                 110

Tyr Thr Val Lys Val Ile Asp Ser Leu Ser Ser Gly Asp Asp Glu Asp
        115                 120                 125
```

-continued

```
Tyr Asp Glu Asp Glu Asp Glu Ala Gly Asn Gly Asn Ala Glu Ala Pro
    130                 135                 140

Tyr Trp Thr Arg Ser Asp Arg Met Glu Lys Lys Leu Leu Ala Val Pro
145                 150                 155                 160

Ala Ala Asn Thr Val Lys Phe Arg Cys Pro Ala Ala Gly Asn Pro Thr
                165                 170                 175

Pro Ser Ile His Trp Leu Lys Asn Gly Lys Glu Phe Lys Gly Glu Gln
            180                 185                 190

Arg Met Gly Gly Ile Lys Leu Arg His Gln Gln Trp Ser Leu Val Met
        195                 200                 205

Glu Ser Ala Val Pro Ser Asp Arg Gly Asn Tyr Thr Cys Val Val Gln
    210                 215                 220

Asn Lys Tyr Gly Ser Ile Lys His Thr Tyr Gln Leu Asp Val Leu Glu
225                 230                 235                 240

Arg Ser Pro His Arg Pro Ile Leu Gln Ala Gly Leu Pro Ala Asn Gln
                245                 250                 255

Thr Val Val Gly Ser Asp Val Glu Phe His Cys Lys Val Tyr Ser
            260                 265                 270

Asp Ala Gln Pro His Ile Gln Trp Leu Lys His Ile Glu Val Asn Gly
        275                 280                 285

Ser Gln Tyr Gly Pro Asn Gly Ala Pro Tyr Val Asn Val Leu Lys Thr
    290                 295                 300

Ala Gly Ile Asn Thr Thr Asp Lys Glu Leu Glu Ile Leu Tyr Leu Thr
305                 310                 315                 320

Asn Val Ser Phe Glu Asp Ala Gly Gln Tyr Thr Cys Leu Ala Gly Asn
                325                 330                 335

Ser Ile Gly Tyr Asn His His Ser Ala Trp Leu Thr Val Leu Pro Ala
            340                 345                 350

Val Glu Met Glu Arg Glu Asp Asp Tyr Ala Asp Ile Leu Ile Tyr Val
        355                 360                 365

Thr Ser Cys Val Leu Phe Ile Leu Thr Met Val Ile Ile Ile Leu Cys
    370                 375                 380

Arg Met Trp Ile Asn Thr Gln Lys Thr Leu Pro Ala Pro Pro Val Gln
385                 390                 395                 400

Lys Leu Ser Lys Phe Pro Leu Lys Arg Gln Val Ser Leu Glu Ser Asn
                405                 410                 415

Ser Ser Met Asn Ser Asn Thr Pro Leu Val Arg Ile Ala Arg Leu Ser
            420                 425                 430

Ser Ser Asp Gly Pro Met Leu Pro Asn Val Ser Glu Leu Glu Leu Pro
        435                 440                 445

Ser Asp Pro Lys Trp Glu Phe Thr Arg Thr Lys Leu Thr Leu Gly Lys
    450                 455                 460

Pro Leu Gly Glu Gly Cys Phe Gly Gln Val Val Met Ala Glu Ala Ile
465                 470                 475                 480

Gly Ile Asp Lys Glu Lys Pro Asn Lys Pro Leu Thr Val Ala Val Lys
                485                 490                 495

Met Leu Lys Asp Asp Gly Thr Asp Lys Asp Leu Ser Asp Leu Val Ser
            500                 505                 510

Glu Met Glu Met Met Lys Met Ile Gly Lys His Lys Asn Ile Ile Asn
        515                 520                 525

Leu Leu Gly Ala Cys Thr Gln Asp Gly Pro Leu Tyr Val Leu Val Glu
    530                 535                 540
```

```
Tyr Ala Ser Lys Gly Asn Leu Arg Glu Tyr Leu Arg Ala Arg Arg Pro
545                 550                 555                 560

Pro Gly Met Asp Tyr Ser Phe Asp Thr Cys Lys Ile Pro Asn Glu Thr
            565                 570                 575

Leu Thr Phe Lys Asp Leu Val Ser Cys Ala Tyr Gln Val Ala Arg Gly
        580                 585                 590

Met Glu Tyr Leu Ala Ser Lys Lys Cys Ile His Arg Asp Pro Ala Ala
    595                 600                 605

Arg Asn Val Leu Val Thr Glu Asp Asn Val Met Lys Ile Ala Asp Phe
610                 615                 620

Gly Leu Ala Arg Asp Val His Asn Ile Asp Tyr Tyr Lys Lys Thr Thr
625                 630                 635                 640

Asn Gly Arg Leu Pro Val Lys Trp Met Ala Pro Glu Ala Leu Phe Asp
                645                 650                 655

Arg Val Tyr Thr His Gln Ser Asp Val Trp Ser Tyr Gly Val Leu Leu
            660                 665                 670

Trp Glu Ile Phe Thr Leu Gly Gly Ser Pro Tyr Pro Gly Ile Pro Val
        675                 680                 685

Glu Glu Leu Phe Lys Leu Leu Lys Glu Gly His Arg Met Asp Lys Pro
690                 695                 700

Ala Asn Cys Thr His Glu Leu Tyr Met Ile Met Arg Glu Cys Trp His
705                 710                 715                 720

Ala Val Pro Ser Gln Arg Pro Thr Phe Arg Gln Leu Val Glu Asp His
                725                 730                 735

Asp Arg Val Leu Ser Met Thr Ser Thr Asp Glu Tyr Leu Asp Leu Ser
            740                 745                 750

Val Pro Phe Glu Gln Tyr Ser Pro Thr Cys Pro Asp Ser Asn Ser Thr
        755                 760                 765

Cys Ser Ser Gly Asp Asp Ser Val Phe Ala His Asp Pro Leu Pro Glu
770                 775                 780

Glu Pro Cys Leu Pro Lys His His His Ser Asn Gly Val Ile Arg Thr
785                 790                 795                 800

<210> SEQ ID NO 29
<211> LENGTH: 20
<212> TYPE: DNA
<213> ORGANISM: Artificial Sequence
<220> FEATURE:
<221> NAME/KEY: primer_bind
<222> LOCATION: (1)...(20)
<223> OTHER INFORMATION: PCR Primer 1

<400> SEQUENCE: 29
agccctcact ccttctctag                                                 20

<210> SEQ ID NO 30
<211> LENGTH: 26
<212> TYPE: DNA
<213> ORGANISM: Artificial Sequence
<220> FEATURE:
<221> NAME/KEY: primer_bind
<222> LOCATION: (1)...(26)
<223> OTHER INFORMATION: PCR Primer 2

<400> SEQUENCE: 30
acctacaggt ggggtctttc attccc                                          26

<210> SEQ ID NO 31
<211> LENGTH: 25
```

```
<212> TYPE: DNA
<213> ORGANISM: Artificial Sequence
<220> FEATURE:
<221> NAME/KEY: primer_bind
<222> LOCATION: (1)...(25)
<223> OTHER INFORMATION: PCR Primer 3

<400> SEQUENCE: 31
ccctgggtca agccctttgt acacc                                              25

<210> SEQ ID NO 32
<211> LENGTH: 25
<212> TYPE: DNA
<213> ORGANISM: Artificial Sequence
<220> FEATURE:
<221> NAME/KEY: primer_bind
<222> LOCATION: (1)...(25)
<223> OTHER INFORMATION: PCR Primer 4

<400> SEQUENCE: 32
tgccaaacct acaggtgggg tcttt                                              25
```

BOTULINUM TOXIN SCREENING ASSAYS

CROSS REFERENCE TO RELATED APPLICATIONS

This is a national stage application under 35 U.S.C. § 371 of PCT application PCT/US2005/006421, filed on Feb. 23, 2005 which claims the benefit of provisional application Ser. No. 60/547,591 filed Feb. 24, 2004, which is hereby incorporated by reference in its entirety.

All of the publications cited in this application are hereby incorporated by reference herein in their entirety.

The myorelaxant properties of Botulinum toxins (BoNTs) are being exploited in a wide variety of therapeutic and cosmetic applications, see e.g., William J. Lipham, COSMETIC AND CLINICAL APPLICATIONS OF BOTULINUM TOXIN (Slack, Inc., 2004). For example, CoNTs therapies are proposed for treating dystonia, see e.g. Kei Roger Aoki, et al., Method for treating Dystonia with Botulinum Toxin C to G, U.S. Pat. No. 6,319,505 (Nov. 20, 2001); pain, see e.g., Kei Roger Aoki, et al., Method for Treating Pain by Peripheral Administration of a Neurotoxin, U.S. Pat. No. 6,464,986 (Oct. 15, 2002); muscle injuries, see e.g. Gregory F. Brooks, Methods for Treating Muscle Injuries, U.S. Pat. No. 6,423,319 (Jul. 23, 2002); cardiovascular diseases, see e.g. Gregory F. Brooks, Methods for Treating Cardiovascular Diseases with Botulinum Toxins, U.S. Patent Publication No. 2003/0185860 (Oct. 2, 2003); neuropsychiatric disorders, see e.g. Steven Donovan, Therapeutic Treatments for Neuropsychiatric Disorders, U.S. Patent Publication No. 2003/0211121 (Nov. 13, 2003); lower back pain, see e.g., Kei Roger Aoki, et al., Botulinum Toxin Therapy for Lower Back Pain, U.S. Patent Publication No. 2004/0037852 (Feb. 26, 2004); as well as other neuromuscular disorders, see e.g., Kei Roger Aoki, et al., Multiple Botulinum Toxins for Treating Neuromuscular Disorders and Conditions, U.S. Patent Publication No. 2001/0021695 (Sep. 13, 2001); Kei Roger Aoki, et al., Treatment of Neuromuscular Disorders and Conditions with Different Botulinum, U.S. Patent Publication No. 2002/0010138 (Jan. 24, 2002); Kei Roger Aoki, et al., Use of Botulinum Toxins for Treating Various Disorders and Conditions and Associated Pain, U.S. Patent Publication No. 2004/0013692 (Jan. 22, 2004). Additional proposed uses of BoNTs as biopharmaceutical neuromodulators has expanded to cover a wide variety of treatments targeting certain disorders that lack a neuromuscular basis. For example, the effects on the autonomic nervous system has allowed the development of a Botulinum toxin serotype A (BoNT/A) therapy for treating axillary hyperhydrosis or sweating, and reports indicate BoNT/A may be an effective treatment for myofascial pain and tension, stroke, traumatic brain injury, cerebral palsy, gastrointestinal motility disorders, urinary incontinence cancer and migraine headaches. Lastly, cosmetic and other therapeutic applications are widely known. In fact, the expected use of BoNTs in both therapeutic and cosmetic treatments of humans is anticipated to expand to an ever widening range of diseases and aliments that can benefit from the myorelaxant properties of these toxins.

The growing clinical and therapeutic use of botulinum toxins necessitates the pharmaceutical industry to use accurate assays for BoNT activity in order to, for example, ensure accurate pharmaceutical formulations and monitor established quality control standards. In addition, given the potential danger associated with small quantities of BoNT in foodstuffs, the food industry requires BoNT activity assays, for example, to validate new food packaging methods and to ensure food safety. Additionally, BoNT activity assays are useful in identifying modulators of BoNT activity, for example, modulators that reduce BoNT activity which can be useful as a toxin antidote and modulators that increase BoNT activity which can be useful in creating more potent or longer lasting pharmaceutical formulations. The present invention provides novel BoNT assays for detecting the presence or activity of a BoNT useful for various industries, such as, e.g. the pharmaceutical and food industries, and provides related advantages as well.

BRIEF DESCRIPTION OF THE DRAWINGS

FIG. 3 shows the results of electroporation of PURE-A into HIT-T15 cells.

FIG. 4 shows the affects of electroporation of HIT-T15 cells over time.

FIG. 7 shows the analysis of two isolated HIT-T15 cell isolates C6 and C7.

FIG. 8 shows Western blot analysis identifying cells with high affinity uptake for a Clostridial toxin.

FIG. 9 shows Western blot analysis evaluating the effects of ganglioside treatments used to increase uptake of a botulinum toxin.

FIG. 10 shows the results of a crosslinking experiment in Neuro-2A cells using a BoNT/A-SBED toxin.

FIG. 13 shows the results FGFR3 phosphorylation studies in Neuro-2A cells.

DETAILED DESCRIPTION OF THE INVENTION

Figure 1:
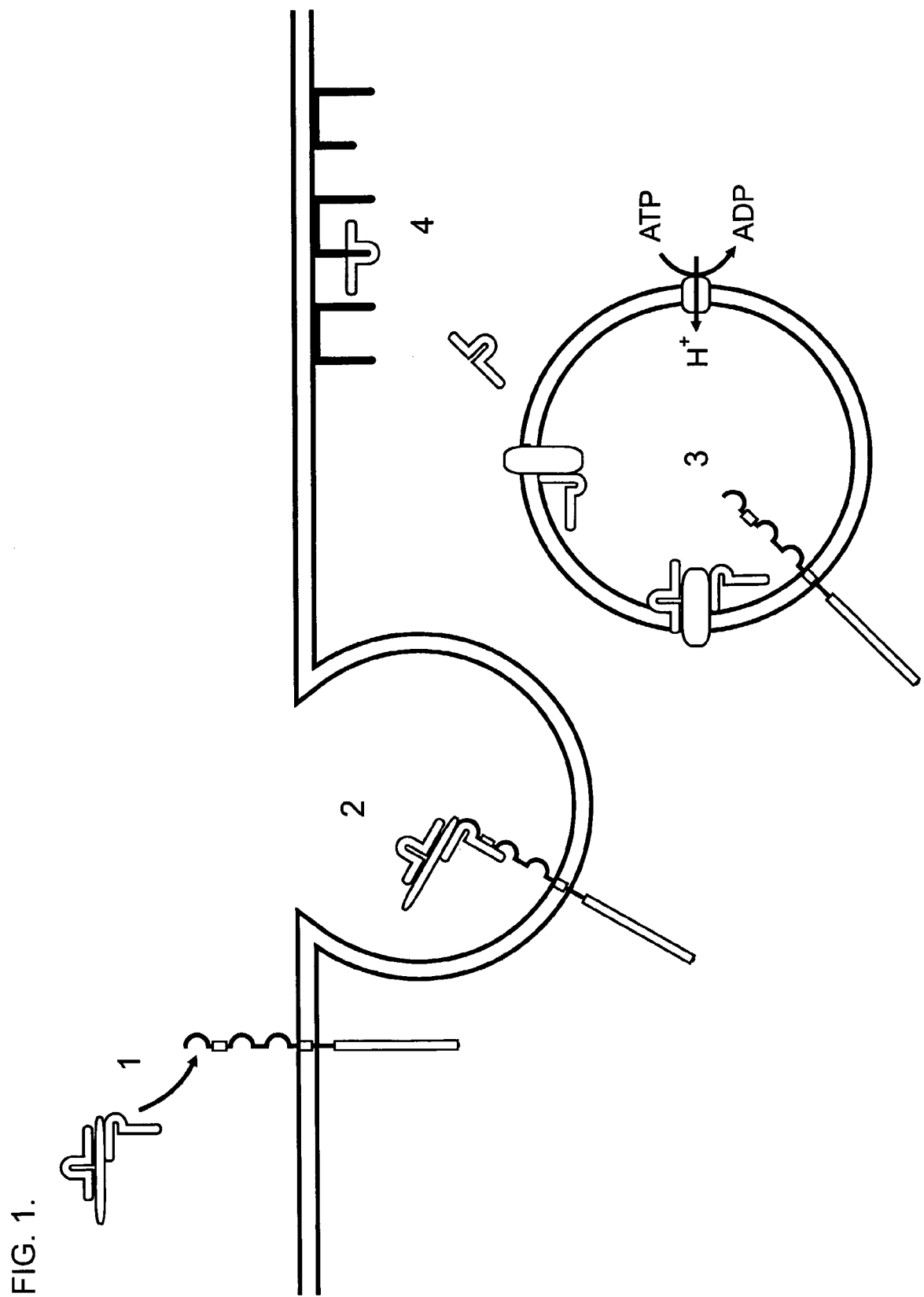
FIG. 1 shows a schematic of the current paradigm of the BoNT/A intoxication mechanism. This intoxication process can be described as comprising four steps: 1) receptor binding, where BoNT/A binds to a BoNT/A receptor system initiates the intoxication process; 2) complex internalization, where after BoNT/A binding, a vesicle containing a toxin/receptor system complex is endocytosised into the cell; 3) light chain translocation, where multiple events are thought to occur, including changes in the internal pH of the vesicle, formation of a channel pore comprising the $H_N$ domain of BoNT/A heavy chain, separation of the BoNT/A light chain from the heavy chain, enzymatic activation of the light chain; and release of the activated light chain and 4) enzymatic target modification, where the activated light chain of BoNT/A proteolytically cleaves its target SNARE substrates, such as, e.g., SNAP-25.

The present invention is based on the identification of a cell surface receptor to which BoNT/A selectively binds as the first step to the selective intoxication of a neuron. The present specification, in part, discloses that the Fibroblast Growth Factor Receptor 3 (FGFR3) is useful as a BoNT receptor, such as, e.g., a BoNT/A receptor. In addition, the present disclosure identifies specific gangliosides which facilitate binding of a BoNT to a BoNT receptor and the internalization of these toxins within a neural cell, such as, e.g. an increased binding of BoNT/A for a BoNT/A receptor using a ganglioside like GT1b; and an increased binding of BoNT/E for a BoNT/E receptor using a ganglioside like GQ1b, GD1a, GD1b or GD3.

The present invention provides novel assays for detecting the presence or absence of an active BoNT/A. The novel methods disclosed in the present specification reduce the need for animal-based toxicity studies, yet serve to analyze multiple toxin functions, namely, binding and cellular uptake of toxin, translocation into the cell cytosol, and protease activity. As discussed further below, the novel methods of the present disclosure can be used to analyze crude and bulk samples as well as highly purified dichain toxins and formulated toxin products and further are amenable to automated high throughput assay formats.

Aspects of the present invention provide methods of detecting BoNT/A activity by contacting a sample to a cell that contains an exogenous FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. Other aspects of the present invention provide methods of detecting BoNT/A activity by contacting a sample to a cell that transiently contains an exogenous FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. Other aspects of the present invention provide methods of detecting BoNT/A activity by contacting a sample to a cell that stably contains an exogenous FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity.

Other aspect of the present invention provide methods of reducing BoNT/A activity in a human comprising administering to said human a pharmaceutical composition comprising a molecule that selectively binds a FGFR3 wherein said selective binding reduces the ability of BoNT/A to bind to said FGFR3.

Other aspect of the present invention provide methods of screening for a molecule able to compete with BoNT/A for selective binding to cells susceptible to BoNT/A intoxication by contacting said sample with a composition comprising an FGFR3 and detecting whether said molecule selectively binds said FGFR3, wherein selective binding of said molecule to said FGFR3 indicates that said molecule is able to compete with BoNT/A for selective binding to cells susceptible to BoNT/A intoxication, and wherein if said molecule is BoNT/A, said method does not comprise an $LD_{50}$ assay.

Other aspect of the present invention provide methods of marketing a neurotoxin capable of selectively binding to the same FGFR3 as BoNT/A comprising obtaining marketing approval from a governmental or regional regulatory authority for a therapeutic neurotoxin, wherein said neurotoxin is assayed for selective binding to a cell comprising contacting said neurotoxin with a composition comprising a FGFR3 and detecting whether said neurotoxin selectively binds said FGFR3, wherein selective binding of said neurotoxin to said FGFR3 indicates that said neurotoxin is able to selective binding to cells susceptible to BoNT/A intoxication and wherein if said molecule is BoNT/A, said method does not comprise an $LD_{50}$ assay; packaging said neurotoxin for sale in a manner consistent with the requirements of said regulatory authority, and selling said neurotoxin.

Other aspect of the present invention provide methods of marketing a neurotoxin capable of selectively binding to the same FGFR3 as BoNT/A comprising obtaining marketing approval from a governmental or regional regulatory authority for a therapeutic neurotoxin, wherein said neurotoxin is assayed for selective binding to a cell comprising contacting said neurotoxin to a cell that contains an exogenous FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity; packaging said neurotoxin for sale in a manner consistent with the requirements of said regulatory authority, and selling said neurotoxin.

BoNTs are each translated as a single chain polypeptide of approximately 150 kDa that is subsequently cleaved by proteolytic scission within a disulphide loop by bacterial or tissue proteases. This posttranslational processing yields a di-chain molecule comprising an approximately 50 kDa light chain (LC) and an approximately 100 kDa heavy chain (HC) held together by a single disulphide bond and noncovalent interactions. Each mature di-chain molecule comprises three functionally distinct domains: 1) an enzymatic domain located in the LC that includes a metalloprotease region containing a zinc-dependent endopeptidase activity which specifically targets core components of the neurotransmitter release apparatus; 2) a translocation domain contained within the amino-terminal half of the HC ($H_N$) that facilitates release of the toxin from intracellular vesicles into the cytoplasm of the target cell; and 3) a binding domain found within the carboxy-terminal half of the HC ($H_C$) that determines the binding activity and binding specificity of the toxin to the receptor complex located at the surface of the target cell.

The binding, translocation and enzymatic activity of these three functional domains are all necessary for toxicity. While all details of this process are not yet precisely known, the overall cellular intoxication mechanism whereby BoNTs enter a neuron and inhibit neurotransmitter release is similar, regardless of type. Although the applicants have no wish to be limited by the following description, the intoxication mechanism can be described as comprising four steps: 1) receptor binding, 2) complex internalization, 3) light chain translocation, and 4) enzymatic target modification (see FIG. 1). The process is initiated when the $H_C$ domain of a BoNT binds to BoNT-specific receptor complex located on the plasma membrane surface of a target cell. The binding specificity of a receptor complex is thought to be achieved, in part, by specific combinations of gangliosides and protein receptors that appear to distinctly comprise each BoNT/A receptor complex. Once bound, the BoNT/receptor complexes are internalized by endocytosis and the internalized vesicles are sorted to specific intracellular routes. The translocation step appears to be triggered by the acidification of the vesicle compartment. This process seems to initiate two important pH-dependent structural rearrangements that increase hydrophobicity and promote enzymatic activation of the toxin. Once activated, light chain endopeptidase of the toxin is released from the intracellular vesicle into the cytosol where it specifically targets one of three known core components of the neurotransmitter release apparatus. There of these core proteins, vesicle-associated membrane protein (VAMP)/synaptobrevin, synaptosomal-associated protein of 25 kDa (SNAP-25) and Syntaxin, are necessary for synaptic vesicle docking and fusion at the nerve terminal and constitute members of the soluble N-ethylmaleimide-sensitive factor-attachment protein-receptor (SNARE) family. The selective proteolysis of synaptic SNAREs accounts for the total block of neurotransmitter release caused by clostridial toxins in vivo. The SNARE protein targets of clostridial toxins are common to exocytosis in a variety of non-neuronal types; in these cells, as in neurons, light chain peptidase activity inhibits exocytosis, see, e.g. Yann Humeau et al., *How Botulinum and Tetanus Neurotoxins Block Neurotransmitter Release*, 82(5) Biochimie. 427-446 (2000); Kathryn Turton et al., *Botulinum and Tetanus Neurotoxins: Structure, Function and Therapeutic Utility*, 27(11) Trends Biochem. Sci. 552-558. (2002); M. Zouhair Atassi, *Basic and Therapeutic Aspects of Botulinum and Tetanus Toxins*, (Dirk W. Dressler & Joseph J. Jankovic eds., 2003); Giovanna Lalli et al., *The Journey of Tetanus and Botulinum Neurotoxins in Neurons*, 11(9) Trends Microbiol. 431-437, (2003).

The three-dimensional crystal structures of BoNT/A indicate that the three functional domains of the toxin are structurally distinct, see e.g., Humeau et al., supra, (2000), Turton et al, supra, (2002); and Lalli et al., supra, (2003). The HEXXH consensus motif of the light chain forms the tetrahedral zinc binding pocket of the catalytic site located in a deep cleft on the protein surface that is accessible by a channel. This conserved zinc binding motif binds at least one zinc atom necessary for its catalytic function. The structure of the $H_N$ and $H_C$ domains consists primarily of β-sheet topologies that are linked by a single α-helix. The $H_N$ domain comprises a β-barrel, jelly-roll fold that resembles the carbohydrate binding moiety found in lectins suggesting that this domain may recognize oligosaccharide-containing molecules and play a role in the intracellular sorting. In addition to its overall structural similarity with lectins, the $H_N$ domain also contains two distinct structural features suggesting functions. First, the $H_N$ domain contains a pair of long amphipathic helices that resemble the coiled-coil motif found in some viral proteins. In viruses, these helices assist in fusing the viral membrane to the cellular membrane of the host, suggesting that the coiled-coil region may assist in inserting the $H_N$ domain into the membrane of an intracellular vescicle. Second, a long loop called the 'translocation belt,' wraps around a large negatively charged cleft of the light chain that blocks access of the zinc atom to the catalytic-binding pocket of active site. The $H_C$ domain contains a ganglioside-binding site and a five residue ganglioside-binding motif. These regions adopt a modified β-trefoil fold structure which forms four distinct carbohydrate binding regions believed to mediate the binding to specific carbohydrate containing acceptor molecules on the cell surface. Consistent with this function, the $H_C$ domain exhibits the highest sequence divergence between clostridial toxins which may account for the distinct binding properties and sorting schemes of TeNT and BoNTs. The $H_C$ domain tilts away from the $H_N$ domain exposing the surface loops and making them accessible for binding. No contact seems to occur between the light chain and the $H_C$ domain. The N-terminus of the $H_C$ region presents a jelly-roll architecture related to that of the S-lectins, a carbohydrate-binding family of proteins. By contrast, the C-terminus of $H_C$ is in a pseudo threefold trefoil conformation that presents structural similarity to the sequentially unrelated interleukins-1α and 1β, Kunitz-type trypsin inhibitors, as well as fibroblast growth factors (FGF). These proteins, mostly β-proteins, are involved in protein-protein interactions.

Cell surface gangliosides appear to be part of the receptor system for BoNT/A and appear to participate in binding of the toxin to its BoNT/A receptor. Although toxin binding is not strictly dependent on the presence of gangliosides, the presence of specific gangliosides appears to be required for high affinity binding. In particular, BoNTs have been observed to interact in vitro and in vivo with polysialogangliosides, especially those of the G1b series (GD1a, GD1b, GD3, GQ1b, or GT1b), see, e.g., Jane L. Halpern & Elaine A. Neale, Neurospecific binding, internalization, and retrograde axonal transport, 195 Curr. Top. Microbiol. Immunol. 221-241 (1995). Preincubation of the toxin with these gangliosides protects the neuromuscular junction (NMJ) of mice from BoNT toxicity. High-affinity, trypsin-sensitive, BoNT-binding sites were found in isolated synaptosomes, see, e.g. R. S. Williams et al, Radioiodination of botulinum neurotoxin type A with retention of biological activity and its binding to brain synaptosomes. 131(2) Eur. J. Biochem. 1437-1445 (1983). Since lectins with high affinity for sialic acid antagonize the binding of BoNTs, their protein receptors may be glycoproteins. Receptors for BoNTs would direct them to acidic vesicles allowing the translocation of the LC into the cytosol of the neuron. The amino acid sequence at the C-terminus of $H_C$ is poorly conserved among different clostridial neurotoxins, and competition experiments have shown that different BoNT serotypes bind to different protein receptors on the surface of neuronal cells. This analysis is therefore consistent with the hypothesis that BoNTs neurotoxins bind to receptor systems comprising at least two components; a protein component and a carbohydrate component.

Based on these findings, and as the present disclosure provided herein, the Applicants have discovered that cells expressing the fibroblast growth factor receptor 3 (FGFR3) can bind BoNT/A. Internalization of the toxin can be followed when these cell lines are exposed to the toxin. Moreover, BoNT/A internalization is inhibited in a dose-dependent manner when FGF, such as, e.g., FGF1, FGF2, FGF4, FGF8 and FGF9, is added at increasing concentrations. Cells tested by the Applicants that did not display the FGFR3 receptor were unable to internalize the toxin, although when subjected to electroporation in the presence of BoNT/A, the intracellular cleavage of SNAP-25 could be detected, indicating that the endopeptidase activity of the toxin remained intact, and that the cells remained susceptible to the endopeptidase. In addition, the Applicants have found that pre-treatment with the polysialoganglioside GT1b increases BoNT/A cellular uptake.

Fibroblast growth factors (FGF) participate in many developmental, differentiation and growth and repair processes of cells through complex combinatorial signaling pathways. Presently, at least 23 ligands (FGF1-23) are known to signal through a family of five transmembrane tyrosine kinase FGF receptors (FGFR1-4). The amino acid sequence identity is highly conserved between FGFR family members and each share a characteristic structural organization. The extracellular portion of FGFRs comprise an amino-terminal hydrophocic signal peptide, three Ig-like domains (IgI, IgII and IgIII) and an acid box domain of approximately eight acidic residues, followed by a single hydrophobic transmembrane domain, which in turn is followed by an intracellular tyrosine kinase domain (see FIG. 2). Affinity of FGFRs for their ligands is highly diverse with different affinities for each family member of growth factors, see, e.g., C. J. Powers et al., Fibroblast growth factors, their receptors and signaling 7(3) Endocr. Relat. Cancer. 165-197 (2000). Table 1 lists some of the known FGF-FGFR signaling relationships of various FGFs and their FGFRs.

TABLE 1

FGFR Variants

| | FGFR1 | | FGFR2 | | FGFR3 | | | |
|---|---|---|---|---|---|---|---|---|
| Variant | IIIb | IIIc | IIIb | IIIc | IIIb | IIIc | FGFR4 | FGFR5 |
| Ligands | FGF-1 | FGF-1 | FGF-1 | FGF-1 | FGF-1 | FGF-1 | FGF-1 | FGF-1 |
| | FGF-2 | FGF-2 | FGF-3 | FGF-2 | FGF-9 | FGF-2 | FGF-2 | FGF-2 |
| | FGF-3 | FGF-4 | FGF-7 | FGF-4 | | FGF-4 | FGF-4 | |
| | FGF-8 | FGF-5 | FGF-10 | FGF-5 | | FGF-8 | FGF-6 | |
| | FGF-10 | FGF-6 | | FGF-6 | | FGF-9 | FGF-8 | |
| | | FGF-8 | | FGF-8 | | | FGF-9 | |
| | | FGF-17 | | FGF-9 | | | | |
| | | | | FGF-17 | | | | |
| Tissues | Brain, bone, kidney, skin, lung, heart, muscle, neuron | | Brain, kidney, skin, lung, liver, glial cells | | Brain, CNS, kidney, skin, lung, testis | | Lung, liver, kidney | Brain, skin, lung testis |

Table 1 - FGFR variants and ligand affinities. FGFR variants, associated ligands, and tissue distribution, see, e.g.,. Powers et al, supra, (2000); and Reuss & von Bohlen und Halbach, supra, (2003).

Diversity in FGF signaling beyond the five receptors is achieved in part by the generation of alternatively spliced variants encoding distinct receptor isoforms, see, e.g. Bernhard Reuss & Oliver von Bohlen und Halbach, Fibroblast growth factors and their receptors in the central nervous system, 313(2) Cell Tissue Res. 139-157 (2003). The protein region that appears to have the highest influence on ligand binding specificity is a portion of the IgIII domain, for which isoforms encoded by three different splice variants have been identified. These three isoforms, designated IgIIIa, IgIIIb and IgIIIc, have relative binding affinities for different FGFR family members. Alternative splicing in the FGFR ligand binding domain, designated a and b, generates additional receptor isoforms with novel ligand affinities. Isoforms for IgIIIa, IgIIIb and IgIIIc have been identified for both FGFR1 and FGFR2. Thus far, the IgIIIa isoform of FGFR3 and the IgIIIa and IgIIIb isoforms of FGFR4 and FGFR5 have not been reported.

Figure 2:
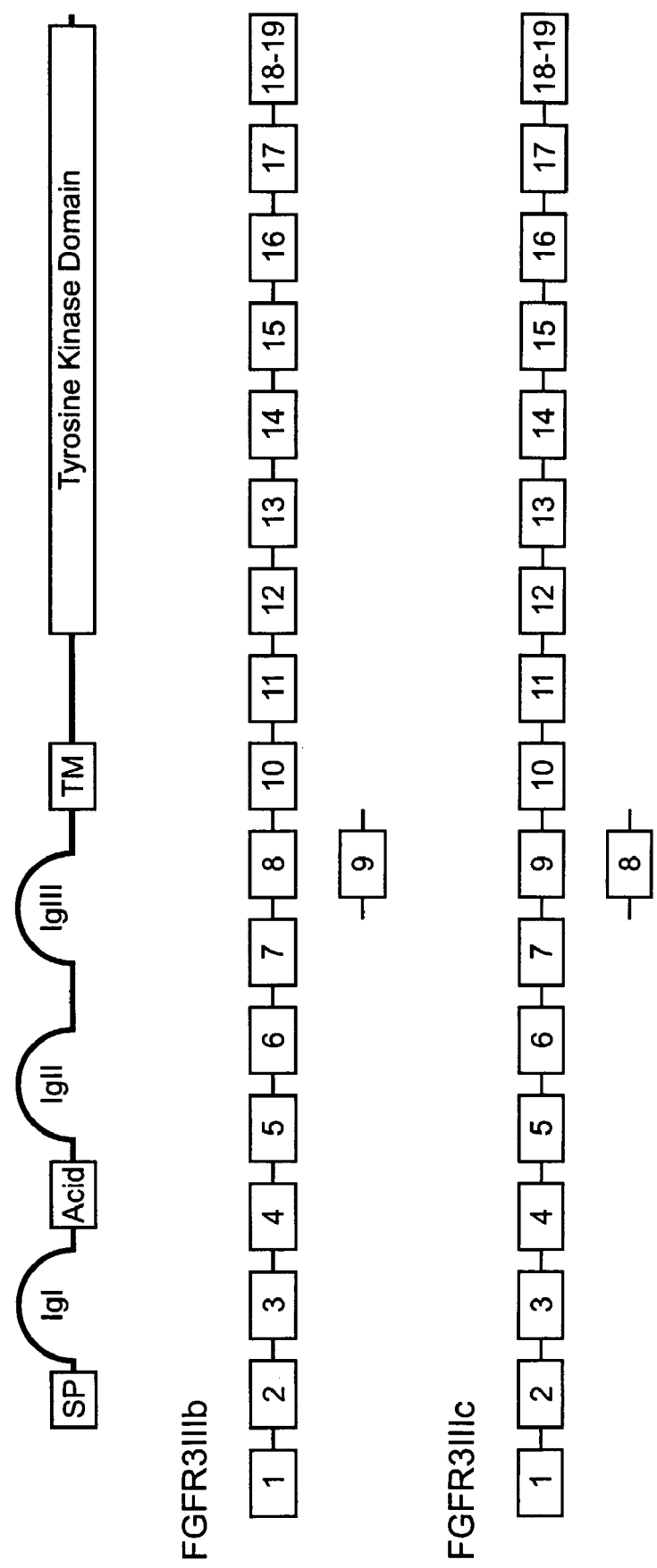
FIG. 2 shows a schematic of an FGFR3 and the alternatively spliced exons that result in FGFR3IIIb and FGFR3IIIc The top diagram shows a generalized drawing of a FGFR3. The extracellular domain comprises a signal peptide (box labeled SP), three Ig-like domains (loops labeled IgI, IgII and IgIII) and an acid box (box labeled acid). A single membrane spanning region comprises the transmembrane domain (box labeled TM). The cytoplasmic portion of the receptor comprises the tyrosine kinase domain. The middle diagram shows a generalized drawing of the exons encoding a FGFR3IIIb isoform, where exon 9 is spliced out from the primary transcript during processing. The lower diagram shows a generalized drawing of the exons encoding a FGFR3IIIc isoform, where exon 8 is spliced out from the primary transcript during processing.

As mentioned above, FGFR3 commonly exists in two isoforms, FGFR3IIIc and FGFR3IIIb, which arise following alternative splicing of the primary transcript in which either exon 8 or 9 respectively is skipped (see FIG. 2). However, additional isoforms exist. For example, an FGFR3 isoform has been described which lacks the acid box, see, e.g., Akio Shimizu et al, A novel alternatively spliced fibroblast growth factor receptor 3 isoform lacking the acid box domain is expressed during chondrogenic differentiation of ATDC5 cells, 276(14) J. Biol. Chem. 11031-11040 (2001). In another example, a novel, potentially cytoplasmic isoform was recently identified, called FGFR3S, in which exons 8, 9 and 10 are spliced out creating a FGFR3 that lacks the second half of IgIIIc and the transmembrane domain, see, e.g., L-M. Sturla et al., FGFR3IIIS: a novel soluble FGFR3 spliced variant that modulates growth is frequently expressed in tumour cells, 89(7) Br. J. Cancer 1276-1284 (2003).

Aspects of the present invention provide, in part, a method of detecting BoNT/A activity by contacting a sample to a cell that contains an exogenous FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In an embodiment, a method of detecting BoNT/A activity comprises contacting a sample to a cell that transiently contains an exogenous FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In another embodiment a method of detecting BoNT/A activity comprises contacting a sample to a cell that stably contains an exogenous FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity.

As used herein "botulinum toxin serotype A" is synonymous with "BoNT/A," "type A," or similar terminology referring unambiguously to *Clostridium botulinum* neurotoxin type A, means any of a number of polypeptide neurotoxins, and derivatives thereof, which can be purified from *Clostridium botulinum* serotype A strains and which share FGFR3 as a cell surface receptor. Such neurotoxins include those found in or corresponding to the following strains and accession numbers listed in Table 2.

TABLE 2

| Strain | Accession No. |
|---|---|
| CL138 | AAQ16535 |
| 137 | AAQ16534 |
| 129 | AAQ16533 |
| 13 | AAQ16532 |
| 42N | AAQ16531 |
| Hall A-hyper | AAM75961 |
| 667Ab | CAA61124 |
| NCTC 2916 | CAA36289 |
| Allergan-Hall A | AAQ06331 |
| 62A | AAA23262 |
| Kyoto-F | CAA51824 |
| type A NIH | BAA11051 |
| NCTC 7272 | |
| 7I03-H | |
| Kumgo | AAO21363 |

As used herein, the term "Fibroblast Growth Factor 3 Receptor" is synonymous with "FGFR3" and means a FGFR3 peptide or peptidomimetic which binds BoNT/A in a manner that elicits a BoNT/A intoxication response. FGFR3s useful in the invention encompass, without limitation, wild type FGFR3s, naturally occurring FGFR3 variants, non-naturally FGFR3 variants, such as, e.g., genetically engineered variants produced by random mutagenesis or rational designed, and active fragments derived from a FGFR3s. As a non-limiting example, a human FGFR3, naturally occurring human FGFR3 variants, non-naturally human FGFR3 variants, and human FGFR3 fragments that retain the ability to selectively bind BoNT/A and mediate the intoxication process, can be useful as a BoNT/A receptor in aspects of the present invention. In another non-limiting example, a bovine FGFR3, naturally occurring bovine FGFR3 variants, non-naturally bovine FGFR3 variants, and bovine FGFR3 fragments that retain the ability to selectively bind BoNT/A and mediate the intoxication process, can be useful as a BoNT/A receptor in aspects of the present invention. In another non-limiting example, a rat FGFR3, naturally occurring rat FGFR3 variants, non-naturally rat FGFR3 variants, and rat FGFR3 fragments that retain the ability to selectively bind BoNT/A and mediate the intoxication process, can be useful as a BoNT/A receptor in aspects of the present invention. In still another non-limiting example, a mouse FGFR3, naturally occurring mouse FGFR3 variants, non-naturally mouse FGFR3 variants, and mouse FGFR3 fragments that retain the ability to selectively bind BoNT/A and mediate the intoxication process, can be useful as a BoNT/A receptor in aspects of the present invention. In another non-limiting example, a chicken FGFR3, naturally occurring chicken FGFR3 variants, non-naturally chicken FGFR3 variants, and chicken FGFR3 fragments that retain the ability to selectively bind BoNT/A and mediate the intoxication process, can be useful as a BoNT/A receptor in aspects of the present invention. In another non-limiting example, a frog FGFR3, naturally occurring frog FGFR3 variants, non-naturally frog FGFR3 variants, and frog FGFR3 fragments that retain the ability to selectively bind BoNT/A and mediate the intoxication process, can be useful as a BoNT/A receptor in aspects of the present invention. In another non-limiting example, a newt FGFR3, naturally occurring newt FGFR3 variants, non-naturally newt FGFR3 variants, and newt FGFR3 fragments that retain the ability to selectively bind BoNT/A and mediate the intoxication process, can be useful as a BoNT/A receptor in aspects of the present invention. In another non-limiting example, a zebrafish FGFR3, naturally occurring zebrafish FGFR3 variants, non-naturally zebrafish FGFR3 variants, and zebrafish FGFR3 fragments that retain the ability to selectively bind BoNT/A and mediate the intoxication process, can be useful as a BoNT/A receptor in aspects of the present invention. In is also understood that both nucleic acid molecules, such as, e.g., DNA and RNA, that encode a FGFR3 disclosed in the present specification and peptide molecules or peptidomimetics comprising a FGFR3 disclosed in the present specification are useful in aspects of the present invention. SEQ ID NO: 1, 3, 5, 7, 9, 11, 13, 15, 17, 19, 21, 23, 25 and 27 disclose nucleic acid molecules encoding representative of FGFR3s useful in aspects on the present invention, while SEQ ID NO: 2, 4, 6, 8, 10, 12, 14, 16, 18, 20, 22, 24, 26 and 28 disclose peptide molecules representative of FGFR3s useful in aspects on the present invention.

As used herein, the term "peptidomimetic" is used broadly to mean a peptide-like molecule that selectively binds BoNT/A as the peptide BoNT/A receptor upon which it is structurally based. Such peptidomimetics include chemically modified peptides, peptide-like molecules containing non-naturally occurring amino acids, and peptoids, which are peptide-like molecules resulting from oligomeric assembly of N-substituted glycines, and selectively bind BoNT/A as the peptide substrate upon which the peptidomimetic is derived, see, e.g. Goodman and Ro, Peptidomimetics for Drug Design, in "Burger's Medicinal Chemistry and Drug Discovery" Vol. 1 (ed. M. E. Wolff; John Wiley & Sons 1995), pages 803-861).

A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; an α,α-dialkyl-glycine or α-aminocycloalkane carboxylic acid; an $N^\alpha$-$C^\alpha$ cyclized amino acid; an N-methylated amino acid; a β- or γ-amino cycloalkane carboxylic acid; an α,β-unsaturated amino acid; a β,β-dimethyl or β-methyl amino acid; a β-substituted-2,3-methano amino acid; an $NC^\delta$ or $C^\alpha$-$C^\delta$ cyclized amino acid; or a substituted proline or another amino acid mimetic. In addition, a peptidomimetic which mimics peptide secondary structure can contain, for example, a nonpeptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylenesulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Thus, in aspects of this embodiment, the FGFR3 can be a human FGFR3IIIb that selectively binds BoNT/A which has, e.g. at least 70% amino acid identity with the FGFR3 of SEQ ID NO: 2, at least 75% amino acid identity with the FGFR3 of SEQ ID NO: 2, at least 80% amino acid identity with the FGFR3 of SEQ ID NO: 2, at least 85% amino acid identity with the FGFR3 of SEQ ID NO: 2, at least 90% amino acid identity with the FGFR3 of SEQ ID NO: 2 or at least 95% amino acid identity with the FGFR3 of SEQ ID NO: 2. In other aspects of this embodiment, the FGFR3 is a human FGFR3IIIb that that selectively binds BoNT/A which has, e.g., at most one, two, three, four, five, six, seven, eight, nine, or ten amino acid substitutions relative to the FGFR3 of SEQ ID NO: 2.

In other aspects of this embodiment, the FGFR3 can be a human FGFR3IIIc that selectively binds BoNT/A which has, e.g. at least 70% amino acid identity with the FGFR3 of SEQ ID NO: 4, at least 75% amino acid identity with the FGFR3 of SEQ ID NO: 4, at least 80% amino acid identity with the FGFR3 of SEQ ID NO: 4, at least 85% amino acid identity with the FGFR3 of SEQ ID NO: 4, at least 90% amino acid identity with the FGFR3 of SEQ ID NO: 4 or at least 95% amino acid identity with the FGFR3 of SEQ ID NO: 4. In other aspects of this embodiment, the FGFR3 is a human FGFR3IIIc that that selectively binds BoNT/A which has, e.g., at most one, two, three, four, five, six, seven, eight, nine, or ten amino acid substitutions relative to the FGFR3 of SEQ ID NO: 4.

In other aspects of this embodiment, the FGFR3 can be a human FGFR3IIIS that selectively binds BoNT/A which has, e.g. at least 70% amino acid identity with the FGFR3 of SEQ ID NO: 6, at least 75% amino acid identity with the FGFR3 of SEQ ID NO: 6, at least 80% amino acid identity with the FGFR3 of SEQ ID NO: 6, at least 85% amino acid identity with the FGFR3 of SEQ ID NO: 6, at least 90% amino acid identity with the FGFR3 of SEQ ID NO: 6 or at least 95% amino acid identity with the FGFR3 of SEQ ID NO: 6. In other aspects of this embodiment, the FGFR3 is a human FGFR3IIIS that that selectively binds BoNT/A which has, e.g., at most one, two, three, four, five, six, seven, eight, nine, or ten amino acid substitutions relative to the FGFR3 of SEQ ID NO: 6.

In other aspects of this embodiment, the FGFR3 can be a bovine FGFR3IIIc that selectively binds BoNT/A which has, e.g. at least 70% amino acid identity with the FGFR3 of SEQ ID NO: 8, at least 75% amino acid identity with the FGFR3 of SEQ ID NO: 8, at least 80% amino acid identity with the FGFR3 of SEQ ID NO: 8, at least 85% amino acid identity with the FGFR3 of SEQ ID NO: 8, at least 90% amino acid identity with the FGFR3 of SEQ ID NO: 8 or at least 95% amino acid identity with the FGFR3 of SEQ ID NO: 8. In other aspects of this embodiment, the FGFR3 is a bovine FGFR3IIIc that that selectively binds BoNT/A which has, e.g., at most one, two, three, four, five, six, seven, eight, nine, or ten amino acid substitutions relative to the FGFR3 of SEQ ID NO: 8.

In other aspects of this embodiment, the FGFR3 can be a mouse FGFR3IIIb that selectively binds BoNT/A which has, e.g. at least 70% amino acid identity with the FGFR3 of SEQ ID NO: 10, at least 75% amino acid identity with the FGFR3 of SEQ ID NO: 10, at least 80% amino acid identity with the FGFR3 of SEQ ID NO: 10, at least 85% amino acid identity with the FGFR3 of SEQ ID NO: 10, at least 90% amino acid identity with the FGFR3 of SEQ ID NO: 10 or at least 95% amino acid identity with the FGFR3 of SEQ ID NO: 10. In other aspects of this embodiment, the FGFR3 is a mouse FGFR3IIIc that that selectively binds BoNT/A which has, e.g. at most one, two, three, four, five, six, seven, eight, nine, or ten amino acid substitutions relative to the FGFR3 of SEQ ID NO: 10.

In other aspects of this embodiment, the FGFR3 can be a mouse FGFR3IIIc that selectively binds BoNT/A which has, e.g. at least 70% amino acid identity with the FGFR3 of SEQ ID NO: 12, at least 75% amino acid identity with the FGFR3 of SEQ ID NO: 12, at least 80% amino acid identity with the FGFR3 of SEQ ID NO: 12, at least 85% amino acid identity with the FGFR3 of SEQ ID NO: 12, at least 90% amino acid identity with the FGFR3 of SEQ ID NO: 12 or at least 95% amino acid identity with the FGFR3 of SEQ ID NO: 12. In other aspects of this embodiment, the FGFR3 is a mouse FGFR3IIIc that that selectively binds BoNT/A which has, e.g. at most one, two, three, four, five, six, seven, eight, nine, or ten amino acid substitutions relative to the FGFR3 of SEQ ID NO: 12.

In other aspects of this embodiment, the FGFR3 can be a mouse FGFR3-delAcid that selectively binds BoNT/A which has, e.g. at least 70% amino acid identity with the FGFR3 of SEQ ID NO: 14, at least 75% amino acid identity with the FGFR3 of SEQ ID NO: 14, at least 80% amino acid identity with the FGFR3 of SEQ ID NO: 14, at least 85% amino acid identity with the FGFR3 of SEQ ID NO: 14, at least 90% amino acid identity with the FGFR3 of SEQ ID NO: 14 or at least 95% amino acid identity with the FGFR3 of SEQ ID NO: 14. In other aspects of this embodiment, the FGFR3 is a mouse FGFR3-delAcid that that selectively binds BoNT/A which has, e.g., at most one, two, three, four, five, six, seven, eight, nine, or ten amino acid substitutions relative to the FGFR3 of SEQ ID NO: 14.

In other aspects of this embodiment, the FGFR3 can be a rat FGFR3IIIb that selectively binds BoNT/A which has, e.g., at least 70% amino acid identity with the FGFR3 of SEQ ID NO: 16, at least 75% amino acid identity with the FGFR3 of SEQ ID NO: 16, at least 80% amino acid identity with the FGFR3 of SEQ ID NO: 16, at least 85% amino acid identity with the FGFR3 of SEQ ID NO: 16, at least 90% amino acid identity with the FGFR3 of SEQ ID NO: 16 or at least 95% amino acid identity with the FGFR3 of SEQ ID NO: 16. In other aspects of this embodiment, the FGFR3 is a rat FGFR3IIIb that that selectively binds BoNT/A which has, e.g., at most one, two, three, four, five, six, seven, eight, nine, or ten amino acid substitutions relative to the FGFR3 of SEQ ID NO: 16.

In other aspects of this embodiment, the FGFR3 can be a rat FGFR3IIIc that selectively binds BoNT/A which has, e.g., at least 70% amino acid identity with the FGFR3 of SEQ ID NO: 18, at least 75% amino acid identity with the FGFR3 of SEQ ID NO: 18, at least 80% amino acid identity with the FGFR3 of SEQ ID NO: 18, at least 85% amino acid identity with the FGFR3 of SEQ ID NO: 18, at least 90% amino acid identity with the FGFR3 of SEQ ID NO: 18 or at least 95% amino acid identity with the FGFR3 of SEQ ID NO: 18. In other aspects of this embodiment, the FGFR3 is a rat FGFR3IIIc that that selectively binds BoNT/A which has, e.g. at most one, two, three, four, five, six, seven, eight, nine, or ten amino acid substitutions relative to the FGFR3 of SEQ ID NO: 18.

In other aspects of this embodiment, the FGFR3 can be a chicken FGFR3 that selectively binds BoNT/A which has, e.g., at least 70% amino acid identity with the FGFR3 of SEQ ID NO: 20, at least 75% amino acid identity with the FGFR3 of SEQ ID NO: 20, at least 80% amino acid identity with the FGFR3 of SEQ ID NO: 20, at least 85% amino acid identity with the FGFR3 of SEQ ID NO: 20, at least 90% amino acid identity with the FGFR3 of SEQ ID NO: 20 or at least 95% amino acid identity with the FGFR3 of SEQ ID NO: 20. In other aspects of this embodiment, the FGFR3 is a chicken FGFR3 that that selectively binds BoNT/A which has, e.g. at most one, two, three, four, five, six, seven, eight, nine, or ten amino acid substitutions relative to the FGFR3 of SEQ ID NO: 20.

In other aspects of this embodiment, the FGFR3 can be a frog FGFR3-1 that selectively binds BoNT/A which has, e.g., at least 70% amino acid identity with the FGFR3 of SEQ ID NO: 22, at least 75% amino acid identity with the FGFR3 of SEQ ID NO: 22, at least 80% amino acid identity with the FGFR3 of SEQ ID NO: 22, at least 85% amino acid identity with the FGFR3 of SEQ ID NO: 22, at least 90% amino acid identity with the FGFR3 of SEQ ID NO: 22 or at least 95% amino acid identity with the FGFR3 of SEQ ID NO: 22. In other aspects of this embodiment, the FGFR3 is a frog FGFR3 that that selectively binds BoNT/A which has, e.g., at most one, two, three, four, five, six, seven, eight, nine, or ten amino acid substitutions relative to the FGFR3 of SEQ ID NO: 22.

In other aspects of this embodiment, the FGFR3 can be a frog FGFR3-2 that selectively binds BoNT/A which has, e.g., at least 70% amino acid identity with the FGFR3 of SEQ ID NO: 24, at least 75% amino acid identity with the FGFR3 of SEQ ID NO: 24, at least 80% amino acid identity with the FGFR3 of SEQ ID NO: 24, at least 85% amino acid identity with the FGFR3 of SEQ ID NO: 24, at least 90% amino acid identity with the FGFR3 of SEQ ID NO: 24 or at least 95% amino acid identity with the FGFR3 of SEQ ID NO: 24. In other aspects of this embodiment, the FGFR3 is a frog FGFR3 that that selectively binds BoNT/A which has, e.g., at most one, two, three, four, five, six, seven, eight, nine, or ten amino acid substitutions relative to the FGFR3 of SEQ ID NO: 24.

In other aspects of this embodiment, the FGFR3 can be a newt FGFR3 that selectively binds BoNT/A which has, e.g., at least 70% amino acid identity with the FGFR3 of SEQ ID NO: 26, at least 75% amino acid identity with the FGFR3 of SEQ ID NO: 26, at least 80% amino acid identity with the FGFR3 of SEQ ID NO: 26, at least 85% amino acid identity with the FGFR3 of SEQ ID NO: 26, at least 90% amino acid identity with the FGFR3 of SEQ ID NO: 26 or at least 95% amino acid identity with the FGFR3 of SEQ ID NO: 26. In other aspects of this embodiment, the FGFR3 is a newt FGFR3 that that selectively binds BoNT/A which has, e.g. at most one, two, three, four, five, six, seven, eight, nine, or ten amino acid substitutions relative to the FGFR3 of SEQ ID NO: 26.

In other aspects of this embodiment, the FGFR3 can be a zebrafish FGFR3 that selectively binds BoNT/A which has, e.g. at least 70% amino acid identity with the FGFR3 of SEQ ID NO: 28, at least 75% amino acid identity with the FGFR3 of SEQ ID NO: 28, at least 80% amino acid identity with the FGFR3 of SEQ ID NO: 28, at least 85% amino acid identity with the FGFR3 of SEQ ID NO: 28, at least 90% amino acid identity with the FGFR3 of SEQ ID NO: 28 or at least 95% amino acid identity with the FGFR3 of SEQ ID NO: 28. In other aspects of this embodiment, the FGFR3 is a zebrafish FGFR3 that that selectively binds BoNT/A which has, e.g. at most one, two, three, four, five, six, seven, eight, nine, or ten amino acid substitutions relative to the FGFR3 of SEQ ID NO: 28.

Other aspects of the present invention provide, in part, the optional use of a polysialogangliosides, especially those of the G1b series, such as, e.g. GD1a, GD1b, GD3, GQ1b, or GT1b. Cell compositions comprising a FGFR3 and a polysialoganglioside can increase the selective binding of BoNT/A relative to a composition not containing a polysialoganglioside. Thus, in an embodiment, a composition comprises a FGFR3 and optionally a polysialoganglioside. In aspects of this embodiment, a composition comprises a FGFR3 and optionally a G1b polysialoganglioside, such as, e.g. GD1a, GD1b, GD3, GQ1b, or GT1b.

Thus, in an embodiment, a method of detecting BoNT/A activity comprises contacting a sample to a cell that contains an exogenous FGFR3 and optionally a G1b polysialoganglioside wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In another embodiment, a method of detecting BoNT/A activity comprises contacting a sample to a cell that transiently contains an exogenous FGFR3 and a G1b polysialoganglioside wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In another embodiment a method of detecting BoNT/A activity comprises contacting a sample to a cell that stably contains an exogenous FGFR3 and a G1b polysialoganglioside wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity.

Other aspects of the present invention provide, in part, a method of detecting BoNT/A activity comprises contacting a sample to a cell that transiently contains an exogenous FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. As used herein, the term "transiently containing" means a FGFR3 that is temporarily introduced into a cell in order to perform the assays disclosed in the present specification. Thus, aspects of a cell transiently containing a FGFR3 disclosed in the specification may include a cell that contains a FGFR3 for, e.g. at most about one day, at most about two days, at most about three days, at most about four days, at most about five days, and at most about six days, at most about seven days, at most about eight days, at most about nine days and at most about ten days.

In an aspect of this embodiment, the FGFR3 can be encoded by the nucleic acid molecule from a mammalian FGFR3, such as, e.g. a human FGFR3, a bovine FGFR3, a rat FGFR3 or a mouse FGFR3; a bird FGFR3, such as, e.g. chicken FGFR3; an amphibian FGFR3, such as, e.g. a newt FGFR3 or a frog FGFR3; and a fish FGFR3, such as, e.g., a zebrafish FGFR3. In an aspect of this embodiment, a method of detecting BoNT/A activity comprises contacting a sample to a cell that transiently contains a nucleic acid molecule encoding an exogenous mammalian FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In another aspect of this embodiment, a method of detecting BoNT/A activity comprises contacting a sample to a cell that transiently contains a nucleic acid molecule encoding an exogenous bird FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In an aspect of this embodiment, a method of detecting BoNT/A activity comprises contacting a sample to a cell that transiently contains a nucleic acid molecule encoding an exogenous amphibian FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In another aspect of this embodiment, a method of detecting BoNT/A activity comprises contacting a sample to a cell that transiently contains a nucleic acid molecule encoding an exogenous fish FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity.

In another aspect of this embodiment, the FGFR3 can be a mammalian FGFR3, such as, e.g., a human FGFR3, a bovine FGFR3, a rat FGFR3 or a mouse FGFR3; a bird FGFR3, such as, e.g., chicken FGFR3; an amphibian FGFR3, such as, e.g. a newt FGFR3 or a frog FGFR3; and a fish FGFR3, such as, e.g., a zebrafish FGFR3. Thus in an embodiment, a method of detecting BoNT/A activity comprises contacting a sample to a cell that transiently contains an exogenous FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In aspect of this embodiment, the FGFR3 can be a mammalian FGFR3, such as, e.g., a human FGFR3, a bovine FGFR3, a rat FGFR3 or a mouse FGFR3; a bird FGFR3, such as, e.g., chicken FGFR3; an amphibian FGFR3, such as, e.g. a newt FGFR3 or a frog FGFR3; and a fish FGFR3, such as, e.g., a zebrafish FGFR3.

In an aspect of this embodiment, a method of detecting BoNT/A activity comprises contacting a sample to a cell that transiently contains an exogenous mammalian FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In another aspect of this embodiment, a method of detecting BoNT/A activity comprises contacting a sample to a cell that transiently contains an exogenous bird FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In an aspect of this embodiment, a method of detecting BoNT/A activity comprises contacting a sample to a cell that transiently contains an exogenous amphibian FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In another aspect of this embodiment, a method of detecting BoNT/A activity comprises contacting a sample to a cell that transiently contains an exogenous fish FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity.

Other aspects of the present invention provide, in part, a method of detecting BoNT/A activity comprises contacting a sample to a cell that stably contains an exogenous FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. As used herein, the term "stably containing" means a FGFR3 that is introduced into a cell and maintained for long periods of time in order to perform the assays of the present specification. Stably-maintained nucleic acid molecules encompass stably-maintained nucleic acid molecules that are extra-chromosomal and replicate autonomously and stably-maintained nucleic acid molecules that are integrated into the chromosomal material of the cell and replicate non-autonomously. Thus aspects of a cell stably containing a FGFR3 disclosed in the specification may include a cell that contains a FGFR3 for, e.g., at least ten days, at least 20 two days, at least 30 days, at least forty days, at least 50 days, and at least 60 days, at least 70 days, at least 80 days, at least 90 days and at least 100 days. Other aspects of a cell stably containing a FGFR3 disclosed in the specification may include a cell that contains a FGFR3 for, e.g., at least 100 days, at least 200 days, at least 300 days, at least 400 days, and at least 500 days. Still other aspects of a cell stably containing a FGFR3 disclosed in the specification may include a cell that permanently contains a FGFR3.

In an aspect of this embodiment, the FGFR3 can be encoded by the nucleic acid molecule from a mammalian FGFR3, such as, e.g. a human FGFR3, a bovine FGFR3, a rat FGFR3 or a mouse FGFR3; a bird FGFR3, such as, e.g. chicken FGFR3; an amphibian FGFR3, such as, e.g. a newt FGFR3 or a frog FGFR3; and a fish FGFR3, such as, e.g., a zebrafish FGFR3. In an aspect of this embodiment, a method of detecting BoNT/A activity comprises contacting a sample to a cell that stably contains a nucleic acid molecule encoding an exogenous mammalian FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In another aspect of this embodiment, a method of detecting BoNT/A activity comprises contacting a sample to a cell that stably contains a nucleic acid molecule encoding an exogenous bird FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In an aspect of this embodiment, a method of detecting BoNT/A activity comprises contacting a sample to a cell that stably contains a nucleic acid molecule encoding an exogenous amphibian FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In another aspect of this embodiment, a method of detecting BoNT/A activity comprises contacting a sample to a cell that stably contains a nucleic acid molecule encoding an exogenous fish FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity.

In another aspect of this embodiment, the FGFR3 can be a mammalian FGFR3, such as, e.g., a human FGFR3, a bovine FGFR3, a rat FGFR3 or a mouse FGFR3; a bird FGFR3, such as, e.g., chicken FGFR3; an amphibian FGFR3, such as, e.g. a newt FGFR3 or a frog FGFR3; and a fish FGFR3, such as, e.g., a zebrafish FGFR3. In an aspect of this embodiment, a method of detecting BoNT/A activity comprises contacting a sample to a cell that stably contains an exogenous mammalian FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In another aspect of this embodiment, a method of detecting BoNT/A activity comprises contacting a sample to a cell that stably contains an exogenous bird FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In an aspect of this embodiment, a method of detecting BoNT/A activity comprises contacting a sample to a cell that stably contains an exogenous amphibian FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity. In another aspect of this embodiment, a method of detecting BoNT/A activity comprises contacting a sample to a cell that stably contains an exogenous fish FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity.

As mentioned above, a nucleic acid molecule can be used to express a FGFR3 disclosed in the present specification. It is envisioned that any and all methods for introducing a nucleic acid molecule into a cell can be used. Methods useful for introducing a nucleic acid molecule into a cell including, without limitation, calcium phosphate-mediated, DEAE dextran-mediated, lipid-mediated, polybrene-mediated, polylysine-mediated, viral-mediated, microinjection, protoplast fusion, biolistic, electroporation and conjugation to an antibody, gramacidin S, artificial viral envelope or other intracellular carrier such as TAT., see, e.g. Introducing Cloned Genes into Cultured Mammalian Cells, pp. 16.1-16.62 (Sambrook & Russell, eds., Molecular Cloning A Laboratory Manual, Vol. 3, 3$^{rd}$ ed. 2001); Alessia Colosimo et al., Transfer and expression of foreign genes in mammalian cells, 29(2) Biotechniques 314-318, 320-322, 324 (2000); Philip Washbourne & A. Kimberley McAllister, Techniques for gene transfer into neurons, 12(5) Curr. Opin. Neurobiol. 566-573 (2002); and Current Protocols in Molecular Biology, John Wiley and Sons, pp 9.16.4-9.16.11 (2000). One skilled in the art understands that selection of a specific method to introduce a nucleic acid molecule into a cell will depend, in part, on whether the cell will transiently contain a BoNT/A receptor or whether the cell will stably contain a BoNT/A receptor.

As mentioned above, a FGFR3 disclosed in the present specification can be introduced into a cell. It is envisioned that any and all methods using a delivery agent to introduce a FGFR3 into a cell can be used. As used herein, the term "delivery agent" means any molecule that enables or enhances internalization of a covalently-linked, non-covalently-linked or in any other manner associated with a FGFR3 into a cell. Thus, the term "delivery agent" encompasses, without limitation, proteins, peptides, peptidomimetics, small molecules, nucleic acid molecules, liposomes, lipids, viruses, retroviruses and cells that, without limitation, transport a covalently or non-covalently linked substrate to the cell membrane, cell cytoplasm or nucleus. It further is understood that the term "delivery agent" encompasses molecules that are internalized by any mechanism, including delivery agents which function via receptor mediated endocytosis and those which are independent of receptor mediated endocytosis.

A delivery agent useful in the invention also can be an agent that enables or enhances cellular uptake of a covalently linked FGFR3, such as, e.g. by chemical conjugation or by genetically produced fusion proteins. Methods that covalently link delivery agents and methods of using such agents are described in, e.g., Steven F. Dowdy, Protein Transduction System and Methods of Use Thereof, International Publication No WO 00/34308 (Jun. 15, 2000); Gérard Chassaing & Alain Prochiantz, Peptides which can be Used as Vectors for the Intracellular Addresing of Active Molecuels, U.S. Pat. No. 6,080,724 (Jun. 27, 2000); Alan Frankel et al., Fusion Protein Comprising TAT-derived Transport Moiert, U.S. Pat. No. 5,674,980 (Oct. 7, 1995); Alan Frankel et al., TAT-derived Transport Polypeptide Conjugates, U.S. Pat. No. 5,747,641 (May 5, 1998); Alan Frankel et al., TAT-derived Transport Polypeptides and Fusion Proteins, U.S. Pat. No. 5,804,604 (Sep. 8, 1998); Peter F. J. O'Hare et al., Use of Transport Proteins, U.S. Pat. No. 6,734,167 (May 11, 2004); Yao-Zhong Lin & Jack J. Hawiger, Method for importing biologically active molecules into cells, U.S. Pat. No. 5,807,746 (Sep. 15, 1998); Yao-Zhong Lin & Jack J. Hawiger, Method for importing biologically active molecules into cells, U.S. Pat. No. 6,043,339 (Mar. 28, 2000); Yao-Zhong Lin et al., Sequence and Method for Genetic Engineering of Proteins with Cell Membrane Translocating Activity, U.S. Pat. No. 6,248,558 (Jun. 19, 2001); Yao-Zhong Lin et al., Sequence and Method for Genetic Engineering of Proteins with Cell Membrane Translocating Activity, U.S. Pat. No. 6,432,680 (Aug. 13, 2002); Jack J. Hawiger et al., Method for importing biologically active molecules into cells, U.S. Pat. No. 6,495,518 (Dec. 17, 2002); Yao-Zhong Lin et al., Sequence and Method for Genetic Engineering of Proteins with Cell Membrane Translocating Activity, U.S. Pat. No. 6,780,843 (Aug. 24, 2004); Jonathan B. Rothbard & Paul A Wender, Method and Composition for Enhancing Transport Across Biological Membranes, U.S. Pat. No. 6,306,993 (Oct. 23, 2001); Jonathan B. Rothbard & Paul A Wender, Method and Composition for Enhancing Transport Across Biological Membranes, U.S. Pat. No. 6,495,663 (Dec. 17, 2002); and Pamela B. Davis et al., Fusion proteins for protein delivery, U.S. Pat. No. 6,287,817 (Sep. 11, 2001).

A delivery agent useful in the invention also can be an agent that enables or enhances cellular uptake of a non-covalently associated FGFR3. Methods that function in the absence of covalent linkage and methods of using such agents are described in, e.g. Gilles Divita et al, Peptide-mediated Transfection Agents and Methods of Use, U.S. Pat. No. 6,841,535 (Jan. 11, 2005); Philip L Felgner and Olivier Zelphati, Intracellular Protein Delivery Compositions and Methods of Use, U.S. Patent Publication No. 2003/0008813); and Michael Karas Intracellular Delivery of Small Molecules, Proteins and Nucleic Acids, U.S. Patent Publication 2004/0209797 (Oct. 21, 2004). Such peptide delivery agents can be prepared and used by standard methods and are commercially available, see, e.g. the Chariot™ Reagent (Active Motif, Carlsbad, Calif.); BioPORTER® Reagent (Gene Therapy Systems, Inc., San Diego, Calif.), BioTrek™ Protein Delivery Reagent (Stratagene, La Jolla, Calif.), and Pro-Ject™ Protein Transfection Reagent (Pierce Biotechnology Inc., Rockford, Ill.).

As mentioned above, a cell can stably contain a FGFR3 disclosed in the present specification. Methods useful for making and using a cells that stably contain an FGFR3 are described in, e.g. Elizabeth E. Plowright et al., Ectopic expression of fibroblast growth factor receptor 3 promotes myeloma cell proliferation and prevents apoptosis, 95(3) Blood 992-998 (2000); TC, see, e.g., Hiroyuki Onose et al., Over-expression of fibroblast growth factor receptor 3 in a human thyroid carcinoma cell line results in overgrowth of the confluent cultures, 140(2) Eur. J. Endocrinol. 169-173 (1999); M. Kana et al., Signal transduction pathway of human fibroblast growth factor receptor 3. Identification of a novel 66-kDa phosphoprotein, 272(10) J. Biol. Chem. 6621-6628 (1997); and Janet E. Henderson et al., Expression of FGFR3 with the G380R achondroplasia mutation inhibits proliferation and maturation of CFK2 chondrocytic cells, 15(1) J. Bone Miner. Res. 155-165 (2000).

Another aspect of the present invention provides, in part, an expression construct that allow for expression of a nucleic acid molecule encoding a FGFR3 disclosed in the present specification. These expression constructs comprise an open reading frame encoding a FGFR3 disclosed in the present specification, operably-linked to control sequences from an expression vector useful for expressing a FGFR3 in a cell. The term "operably linked" as used herein, refers to any of a variety of cloning methods that can ligate a nucleic acid molecule disclosed in the present specification into an expression vector such that a peptide encoded by the composition is expressed when introduced into a cell. Well-established molecular biology techniques that may be necessary to make an expression construct disclosed in the present specification including, but not limited to, procedures involving polymerase chain reaction (PCR) amplification restriction enzyme reactions, agarose gel electrophoresis, nucleic acid ligation, bacterial transformation, nucleic acid purification, nucleic acid sequencing are routine procedures well within the scope of one skilled in the art and from the teaching herein. Non-limiting examples of specific protocols necessary to make an expression construct are described in e.g. MOLECULAR CLONING A LABORATORY MANUAL, supra, (2001); and CURRENT PROTOCOLS IN MOLECULAR BIOLOGY (Frederick M. Ausubel et al., eds. John Wiley & Sons, 2004). These protocols are routine procedures well within the scope of one skilled in the art and from the teaching herein.

A wide variety of expression vectors can be employed for expressing an open reading frame encoding a FGFR3 and include without limitation, viral expression vectors, prokaryotic expression vectors and eukaryotic expression vectors including yeast, insect and mammalian expression vectors. Non-limiting examples of expression vectors, along with well-established reagents and conditions for making and using an expression construct from such expression vectors are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; EMD Biosciences-Novagen, Madison, Wis.; QIAGEN, Inc., Valencia, Calif.; and Stratagene, La Jolla, Calif. The selection, making and use of an appropriate expression vector are routine procedures well within the scope of one skilled in the art and from the teachings herein.

It is envisioned that any of a variety of expression systems may be useful for expressing construct compositions disclosed in the present specification. An expression system encompasses both cell-based systems and cell-free expression systems. Cell-based systems include, without limited, viral expression systems, prokaryotic expression systems, yeast expression systems, baculoviral expression systems, insect expression systems and mammalian expression systems. Cell-free systems include, without limitation, wheat germ extracts, rabbit reticulocyte extracts and *E. coli* extracts. Expression using an expression system can include any of a variety of characteristics including, without limitation, inducible expression, non-inducible expression, constitutive expression, viral-mediated expression, stably-integrated expression, and transient expression. Expression systems that include well-characterized vectors, reagents, conditions and cells are well-established and are readily available from commercial vendors that include, without limitation, Ambion, Inc. Austin, Tex.; BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; Roche Applied Science, Indianapolis, Ind.; and Stratagene, La Jolla, Calif. Non-limiting examples on the selection and use of appropriate heterologous expression systems are described in e.g., PROTEIN EXPRESSION. A PRACTICAL APPROACH (S. J. Higgins and B. David Hames eds., Oxford University Press, 1999); Joseph M. Fernandez & James P. Hoeffler, GENE EXPRESSION SYSTEMS. USING NATURE FOR THE ART OF EXPRESSION (Academic Press, 1999); and Meena Rai & Harish Padh, *Expression Systems for Production of Heterologous Proteins,* 80(9) CURRENT SCIENCE 1121-1128, (2001). These protocols are routine procedures well within the scope of one skilled in the art and from the teaching herein.

An expression construct comprising a nucleic acid molecule encoding a FGFR3 disclosed in the present specification can be operationally-linked to a variety of regulatory elements that can positively or negatively modulate, either directly or indirectly, the expression of a nucleic acid molecule, such as, e.g. constitutive, tissue-specific, inducible or synthetic promoters and enhancers. Non-limiting examples of constitutive regulatory elements include, e.g. the cytomegalovirus (CMV), herpes simplex virus thymidine kinase (HSV TK), simian virus 40 (SV40) early, 5' long terminal repeat (LTR), elongation factor-1α (EF-1α) and polybiquitin (UbC) regulatory elements. Non-limiting examples of inducible regulatory elements useful in aspects of the present invention include, e.g., chemical-inducible regulatory elements such as, without limitation, alcohol-regulated, tetracycline-regulated, steroid-regulated, metal-regulated and pathogenesis-related; and physical-inducible regulatory elements such as, without limitation, temperature-regulated and light-regulated. Such inducible regulatory elements can be prepared and used by standard methods and are commercially available, including, without limitation, tetracycline-inducible and tetracycline-repressible elements such as, e.g. Tet-On™ and Tet-Off™ (BD Biosciences-Clontech, Palo Alto, Calif.) and the T-REx™ (Tetracycline-Regulated Expression) and Flp-In™ T-REx™ systems (Invitrogen, Inc., Carlsbad, Calif.); ecdysone-inducible regulatory elements such as, e.g. the Complete Control Inducible Mammalian Expression System (Stratagene, Inc., La Jolla, Calif.); isopropyl β-D-galactopyranoside (IPTG)-inducible regulatory elements such as, e.g. the LacSwitch® II Inducible Mammalian Expression System (Stratagene, Inc., La Jolla, Calif.); and steroid-inducible regulatory elements such as, e.g. the chimeric progesterone receptor inducible system, GeneSwitch™ (Invitrogen, Inc., Carlsbad, Calif.). The skilled person understands that these and a variety of other constitutive and inducible regulatory systems are commercially available or well known in the art and can be useful in the invention for controlling expression of a nucleic acid molecule which encodes a BoNT/A receptor.

In an embodiment, a nucleic acid molecule encoding a FGFR3 can optionally be linked to a regulatory element such as a constitutive regulatory element. In aspects of this embodiment, a nucleic acid molecule encoding a mammalian FGFR3 can optionally be linked to a regulatory element such as a constitutive regulatory element; a nucleic acid molecule encoding a bird FGFR3 can optionally be linked to a regulatory element such as a constitutive regulatory element; a nucleic acid molecule encoding an amphibian FGFR3 can optionally be linked to a regulatory element such as a constitutive regulatory element; and a nucleic acid molecule encoding a fish FGFR3 can optionally be linked to a regulatory element such as a constitutive regulatory element.

In another embodiment, a nucleic acid molecule encoding a FGFR3 can optionally be linked to a regulatory element such as an inducible regulatory element. In aspects of this embodiment, a nucleic acid molecule encoding a mammalian FGFR3 can optionally be linked to a regulatory element such as a inducible regulatory element; a nucleic acid molecule encoding a bird FGFR3 can optionally be linked to a regulatory element such as a inducible regulatory element; a nucleic acid molecule encoding an amphibian FGFR3 can optionally be linked to a regulatory element such as a inducible regulatory element; and a nucleic acid molecule encoding a fish FGFR3 can optionally be linked to a regulatory element such as a inducible regulatory element. In another aspect of this embodiment, expression of the nucleic acid molecule is induced using, e.g., tetracycline-inducible, ecdysone-inducible or steroid-inducible.

It is understood that a FGFR3 useful in aspects of the present invention optionally can include one or more additional components. As a non-limiting example, a flexible spacer sequence such as poly-glycine sequences can be included in a FGFR3 useful in the invention. A useful FGFR3 can further include, without limitation, one or more of the following: epitope-binding tags, such as. e.g. FLAG, Express™, human Influenza virus hemagluttinin (HA), human $p62^{c-Myc}$ protein (c-MYC), Vesicular Stomatitis Virus Glycoprotein (VSV-G), glycoprotein-D precursor of Herpes simplex virus (HSV), V5, and AU1; affinity-binding, such as. e.g. polyhistidine (HIS), streptavidin binding peptide (strep), and biotin or a biotinylation sequence; peptide-binding regions, such as. e.g., the glutathione binding domain of glutathione-S-transferase, the calmodulin binding domain of the calmodulin binding protein, and the maltose binding domain of the maltose binding protein; immunoglobulin hinge region; an N-hydroxysuccinimide linker; a peptide or peptidomimetic hairpin turn; or a hydrophilic sequence or another component or sequence that, for example, promotes the solubility or stability of a FGFR3. Non-limiting examples of specific protocols for selecting, making and using an appropriate binding peptide are described in, e.g. Epitope Tagging, pp. 17.90-17.93 (Sambrook and Russell, eds., Molecular Cloning A Laboratory Manual, Vol. 3, $3^{rd}$ ed. 2001); Antibodies: A Laboratory Manual (Edward Harlow & David Lane, eds., Cold Spring Harbor Laboratory Press, $2^{nd}$ ed. 1998); and Using Antibodies: A Laboratory Manual: Portable Protocol No. I (Edward Harlow & David Lane, Cold Spring Harbor Laboratory Press, 1998). In addition, non-limiting examples of binding peptides as well as well-characterized reagents, conditions and protocols are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; and Stratagene, La Jolla, Calif. These protocols are routine procedures well within the scope of one skilled in the art and from the teaching herein.

Aspects of the present invention provide, in part, a cell that contains an exogenous FGFR3 wherein said cell is capable of BoNT/A intoxication. As used herein, the term "cell," means any eukaryotic cell that expresses, or can be engineered to express, at least one exogenous FGFR3 that binds BoNT/A. The term cell encompasses cells from a variety of organisms, such as, e.g. murine, rat, porcine, bovine, equine, primate and human cells; from a variety of cell types such as, e.g. neural and non-neural; and can be isolated from or part of a heterogeneous cell population, tissue or organism. It is understood that cells useful in aspects of the invention can included, without limitation, primary cells; cultured cells; established cells; normal cells; transformed cells; tumor cells; infected cells; proliferating and terminally differentiated cells; and stably or transiently transfected cells, including stably and transiently transfected cells. It is further understood that cells useful in aspects of the invention can be in any state such as proliferating or quiescent; intact or permeabilized such as through chemical-mediated transfection such as, e.g. calcium phosphate-mediated, diethyl-laminoethyl (DEAE) dextran-mediated, lipid-mediated, polyethyleneimine (PEI)-mediated, polybrene-mediated, and protein delivery agents; physical-mediated tranfection, such as, e.g. biolistic particle delivery, microinjection and electroporation; and viral-mediated transfection, such as, e.g., retroviral-mediated transfection. It is further understood that cells useful in aspects of the invention may include those which express a FGFR3 under control of a constitutive, tissue-specific, cell-specific or inducible promoter element, enhancer element or both.

As used herein, the term "cell capable of BoNT/A intoxication" means a cell that can enable the overall cellular mechanism whereby BoNT/A proteolytically cleaves a substrate, such as, e.g. SNAP-25, and encompasses the binding of BoNT/A to a low or high affinity receptor, the internalization of the toxin/receptor complex, the translocation of the BoNT/A light chain into the cytoplasm and the enzymatic target modification of a BoNT/A substrate. By definition, a cell capable of BoNT/A intoxication must express a FGFR3. As a non-limiting example, a neuronal or non-neuronal cell can be transiently or stably engineered to express an exogenous nucleic acid molecule encoding a FGFR3. As another non-limiting example, a neuronal or non-neuronal cell can be transiently engineered to contain an exogenous FGFR3.

Cells useful in aspects of the invention include both neuronal and non-neuronal cells. Neuronal cells useful in aspects of the invention include, without limitation, primary neuronal cells; immortalized or established neuronal cells; transformed neuronal cells; neuronal tumor cells; stably and transiently transfected neuronal cells and further include, yet are not limited to, mammalian, murine, rat, primate and human neuronal cells. Non-limiting examples of neuronal cells useful in aspects of the invention include, e.g. peripheral neuronal cells, such as, e.g. motor neurons and sensory neurons; and CNS neuronal cells, such as, e.g. spinal cord neurons like embryonic spinal cord neurons, dorsal root ganglia (DRG) neurons, cerebral cortex neurons, cerebellar neurons, hippocampal neurons and motor neurons. Neuronal cells useful in the invention can be, for example, central nervous system (CNS) neurons; neuroblastoma cells; motor neurons, hippocampal neurons or cerebellar neurons and further can be, without limitation, Neuro-2A, SH-SY5Y, NG108-15, N1E-115 or SK-N-DZ cells. The skilled person understands that these and additional primary and established neurons can be useful in the cells and methods of the invention.

Neurons useful in aspects of the invention include, without limitation, primary cultures such as primary cultures of embryonic dorsal root ganglion (DRG) neurons. As one example, primary cultures of embryonic rat DRG neurons are described in Mary J. Welch et al., Sensitivity of embryonic rat dorsal root ganglia neurons to *Clostridium botulinum* neurotoxins, 38(2) Toxicon 245 258 (2000); and primary cultures of fetal spinal cord neurons, for example, primary cultures of murine fetal spinal cord neurons are described in Elaine A. Neale et al., Botulinum neurotoxin A blocks synaptic vesicle exocytosis but not endocytosis at the nerve terminal, 147(6) J. Cell Biol. 1249-1260 (1999), and John A. Chaddock et al., Inhibition of vesicular secretion in both neuronal and non-neuronal cells by a retargeted endopeptidase derivative of *Clostridium botulinum* neurotoxin type A, 68(5) Infect. Immun. 2587-2593 (2000). Thus, in an embodiment, a cell capable of BoNT/A intoxication can be a neuron that contains an exogenous FGFR3. In aspects of this embodiment, a neuron can be a neuron from, e.g. a primary culture, an embryonic dorsal root ganglion primary culture or a fetal spinal cord primary culture. As non-limiting examples, cells useful according to a method disclosed in the present specification can include, a primary neuronal cell that contains an exogenous FGFR3, such as, e.g., a rat embryonic dorsal root ganglion (DRG) neuron that contains an exogenous FGFR3 or a murine fetal spinal cord neuron that contains an exogenous FGFR3.

Neuronal cell lines useful in aspects of the invention include, without limitation, neuroblastoma cell lines, neuronal hybrid cell lines, spinal cord cell lines, central nervous system cell lines, cerebral cortex cell lines, dorsal root ganglion cell lines, hippocampal cell lines and pheochromocytoma cell lines.

Neuroblastoma cell lines, such as, e.g. murine, rat, primate or human neuroblastoma cell lines can be useful in aspects of the invention. Neuroblastoma cell lines useful in aspects of the invention include, without limitation, BE(2)-C (ATCC CRL-2268; ECACC 95011817), BE(2)-M17 (ATCC CRL-2267; ECACC 95011816), C1300 (ECACC 93120817), CHP-212 (ATCC CRL-2273), CHP-126 (DSMZ ACC 304), IMR 32 (ATCC CRL-127; ECACC 86041809; DSMZ ACC 165), KELLY (ECACC 92110411; DSMZ ACC 355), LA-N-2, see, e.g. Robert C. Seeger et al., Morphology, growth, chromosomal pattern and fibrinolytic activity of two new human neuroblastoma cell lines, 37(5) Cancer Res. 1364-1371 (1977); and G. J. West et al., Adrenergic, cholinergic, and inactive human neuroblastoma cell lines with the action-potential Na+ ionophore, 37(5) Cancer Res. 1372-1376 (1977), MC-IXC (ATCC CRL-2270), MHH-NB-11 (DSMZ ACC 157), N18Tg2 (DSMZ ACC 103), N1E-115 (ATCC CCL-2263; ECACC 88112303), N4TG3 (DSMZ ACC 101), Neuro-2A (ATCC CCL-131; ECACC 89121404; DSMZ ACC 148), NB41A3 (ATCC CCL-147; ECACC 89121405), NS20Y (DSMZ ACC 94), SH-SY5Y (ATCC CRL-2266; ECACC 94030304; DSMZ ACC 209), SIMA (DSMZ ACC 164), SK-N-DZ (ATCC CRL-2149; ECACC 94092305), SK-N-F1 (ATCC CRL-2142, ECACC 94092304), SK-N-MC (ATCC HTB-10, DSMZ ACC 203) and SK-N-SH (ATCC HTB-11, ECACC 86012802). Thus, in an embodiment, a cell capable of BoNT/A intoxication can be a neuroblastoma cell that contains an exogenous FGFR3. In aspects of this embodiment, a neuroblastoma cell can be, e.g., BE(2)-C, BE(2)-M17, C1300, CHP-212, CHP-126, IMR 32, KELLY, LA-N-2, MC-IXC, MHH-NB-11, N18Tg2, N1E-115, N4TG3, Neuro-2A, NB41A3, NS20Y, SH-SY5Y, SIMA, SK-N-DZ, SK-N-F1, SK-N-MC and SK-N-SH. As non-limiting examples, cells useful for detecting BoNT/A activity according to a method disclosed in the present specification can include, a neuroblastoma cell that contains an exogenous FGFR3, such as, e.g., a SH-SY5Y cell that contains an exogenous FGFR; a Neuro-2a cell that contains an exogenous FGFR3; and a N1E-115 cell that contains an exogenous FGFR3; and a SK-N-DZ cell that contains an exogenous FGFR3.

Neuronal hybrid cell lines, such as, e.g., murine, rat, primate and human hybrid neuronal cell lines can be useful in aspects of the invention. Such hybrid cell lines include neuroblastoma/glioma hybrids, such as, e.g. N18 (ECACC 88112301), NG108-15 (ATCC HB-12317, ECACC 88112302) and NG115-401L (ECACC 87032003); neuroblastoma/motor neuron hybrids, such as, e.g., NSC-19 and NSC-34, which express motor neuron characteristics, display a multipolar neuron-like phenotype, express high levels of choline acetyltransferase (CHAT), generate action potentials, express neurofilament triplet proteins and synthesize, store and release acetylcholine, see, e.g. N. R. Cashman et al., Neuroblastoma x spinal cord (NSC) hybrid cell lines resemble developing motor neurons, 194(3) Dev. Dyn. 209-221 (1992); and Christopher J. Eggett et al., Development and characterisation of a glutamate-sensitive motor neuronal cell line, 74(5) J. Neurochem. 1895-1902 (2000); neuroblastoma/root ganglion neuron hybrids, such as, e.g., F11, see, e.g., Doros Platika et al., Neuronal traits of clonal cell lines derived by fusion of dorsal root ganglia neurons with neuroblastoma cells, 82(10) Proc. Natl. Acad. Sci. U.S.A. 3499-3503 (1985), ND-E (ECACC 92090915), ND-U1 (ECACC 92090916), ND7/23 (ECACC 92090903), ND8/34 (ECACC 92090904) and ND27 (ECACC 92090912); neuroblastoma/hippocampal neuron hybrids, such as, e.g., HN-33, see, e.g., Henry J. Lee et al., Neuronal properties and trophic activities of immortalized hippocampal cells from embryonic and young adult mice. 10(6) J. Neurosci. 1779-1787 (1990). Thus, in an embodiment, a cell capable of BoNT/A toxin intoxication can be a hybrid neuron that contains an exogenous FGFR3. In aspects of this embodiment, a hybrid neuron can be, e.g., a neuroblastoma/glioma hybrid cell that contains an exogenous FGFR3, a neuroblastoma/motor neuron hybrid cell that contains an exogenous FGFR3, a neuroblastoma/root ganglion neuron hybrid cell that contains an exogenous FGFR3 and a neuroblastoma/hippocampal neuron hybrid cell that contains an exogenous FGFR3. In further aspects of this embodiment, a neuroblastoma/glioma hybrid can be, e.g., N18, NG108-15 and NG115-401L. In further aspects of this embodiment, a neuroblastoma/motor neuron hybrid can be, e.g., NSC-19 and NSC-32. In further aspects of this embodiment, a neuroblastoma/root ganglion neuron hybrid can be, e.g. F11, ND-E, ND-U1, ND7/23, ND8/34 and ND27. In further aspects of this embodiment, a neuroblastoma/hippocampal neuron hybrid can be, e.g., HN-33. As non-limiting examples, cells useful for detecting BoNT/A activity according to a method disclosed in the present specification can include, a neuronal hybrid cell, such as, e.g. a NG108-15 cell that contains an exogenous FGFR3.

Spinal cord cell lines, such as, e.g. murine, rat, primate or human spinal cord cell lines can be useful in aspects of the invention and include, without limitation, TE 189.T (ATCC CRL-7947) and M4b, see, e.g., Ana M. Cardenas et al., Establishment and characterization of immortalized neuronal cell lines derived from the spinal cord of normal and trisomy 16 fetal mice, an animal model of Down syndrome, 68(1) J. Neurosci. Res. 46-58 (2002). As an example, a human spinal cord cell line can be generated from precursors of human embryonic spinal cord cells (first trimester embryos) that are immortalized with a tetracycline repressible v-myc oncogene as described in Ronghao Li et al., Motoneuron differentiation of immortalized human spinal cord cell lines, 59(3) J. Neurosci. Res. 342-352 (2000). Such cells can be expanded indefinitely in proliferative growth conditions before rapid differentiation (4-7 days) into functional neurons that express neuronal phenotypic markers such as choline acetyltransferase. As another example, a murine spinal cord cell line can be prepared by immortalizing an embryonic spinal cord culture using transforming media. Such a spinal cord cell line can be, for example, the murine M4b line and can express neuronal markers such as NSE, synaptophysin, MAP 2 and choline acetyltransferase, and can release acetylcholine upon appropriate stimulation, see, e.g. Cardenas et al., supra, (2002). Thus, in an embodiment, a cell capable of BoNT/A intoxication can be a spinal cord cell that contains an exogenous FGFR3. In aspects of this embodiment, a spinal cord cell that contains an exogenous FGFR3 can be, e.g., a TE 189.T cell that contains an exogenous FGFR3 and a M4b cell that contains an exogenous FGFR3.

Central nervous system (CNS) cell lines, such as, e.g. murine, rat, primate and human CNS cell lines, can be useful in aspects of the invention. A useful CNS cell line can be, for example, a human CNS cell line immortalized with a tetracycline repressible v-myc oncogene as described in Dinah W. Sah et al., Bipotent progenitor cell lines from the human CNS, 15(6) Nat. Biotechnol. 574-580 (1997). Upon repression of the oncogene, the cells differentiate into neurons. Thus, in an embodiment, a cell capable of BoNT/A intoxication can be a CNS cell that contains an exogenous FGFR3.

Cerebral cortex cell lines, such as, e.g., murine, rat, primate and human cerebral cortex cell lines, can be useful in aspects of the invention and include, without limitation, CNh, see, e.g., Ana M. Cardenas et al., Calcium signals in cell lines derived from the cerebral cortex of normal and trisomy 16 mice, 10(2) Neuroreport 363-369 (1999), HCN-1a (ATCC CRL-10442) and HCN-2 (ATCC CRL-10742). As an example, murine cortex primary cultures from 12-16 days embryos can be immortalized, for example, by culturing the cells in conditioned media from a rat thyroid cell line that induces transformation in vitro. The immortalized cells can be differentiated into neurons expressing neuronal markers using the appropriate media; these differentiated cells express choline acetyltransferase and secrete acetylcholine and glutamate in response to depolarization and nicotine stimulation, see, e.g., David D. Allen et al., Impaired cholinergic function in cell lines derived from the cerebral cortex of normal and trisomy 16 mice, 12(9) Eur. J. Neurosci. 3259-3264 (2000). Thus, in an embodiment, a cell capable of BoNT/A intoxication can be a cerebral cortex cell that contains an exogenous FGFR3. In aspects of this embodiment, a cerebral cortex cell that contains an exogenous FGFR3 can be, e.g. a CNh cell that contains an exogenous FGFR3, HCN-1a cell that contains an exogenous FGFR3 and HCN-2 cell that contains an exogenous FGFR3.

Dorsal root ganglia cell lines, such as, e.g., murine, rat, primate and human dorsal root ganglia cell lines, can be useful in aspects of the invention and include, without limitation, G4b, see, e.g., David D. Allen et al., A dorsal root ganglia cell line derived from trisomy 16 fetal mice, a model for Down syndrome, 13(4) Neuroreport 491-496 (2002). Embryonic dorsal root ganglia primary cultures can be immortalized with transforming conditioned media as described above. Upon differentiation, the cell line exhibits neuronal traits and lacks glial markers by immunohistochemistry. Release of neurotransmitters such as acetylcholine can be induced in response to potassium and nicotine, see, e.g., Allen et al., supra, (2002). Thus, in an embodiment, a cell capable of BoNT/A intoxication can be a dorsal root ganglia cell that contains an exogenous FGFR3. In aspects of this embodiment, a dorsal root ganglia cell can be, e.g., a G4b cell that contains an exogenous FGFR3.

Hippocampal cell lines, such as, e.g. murine, rat, primate and human hippocampal lines can be useful in aspects of the invention and include, without limitation, HT-4, see, e.g., K. Frederiksen et al., Immortalization of precursor cells from the mammalian CNS, 1(6) Neuron 439-448 (1988) and HT-22, see, e.g. John B. Davis and Pamela Maher, Protein kinase C activation inhibits glutamate-induced cytotoxicity in a neuronal cell line, 652(1) Brain Res. 169-173 (1994). As a non-limiting example, the murine hippocampal cell line HT-22 can be useful in the invention. As a further non-limiting example, the immortalized HN33 hippocampal cell line can be useful in the invention. This hippocampal cell line was derived from the fusion of primary neurons from the hippocampus of postnatal day 21 mice with the N18TG2 neuroblastoma cell line, and, when differentiated, shares membrane properties with adult hippocampal neurons in primary culture, see, e.g., Henry J. Lee et al., Neuronal Properties and Trophic Activities of Immortalized Hippocampal Cells from Embryonic and Young Adult Mice, 19(6) J. Neurosci. 1779-1787 (1990); and Henry J. Lee et al., Immortalized young adult neurons from the septal region: generation and characterization, 52(1-2) Brain Res. Dev Brain Res. 219-228 (1990). Thus, in an embodiment, a cell capable of BoNT/A intoxication can be a hippocampal cell that contains an exogenous FGFR3. In aspects of this embodiment, a hippocampal cell that contains an exogenous FGFR3 can be, e.g., a HT-4 cell that contains an exogenous FGFR3, a HT-22 cell that contains an exogenous FGFR3 and a HN33 cell that contains an exogenous FGFR3.

A variety of non-neuronal cells are useful in aspects of the invention. Non-neuronal cells useful in aspects of the invention include, without limitation, primary non-neuronal cells; immortalized or established non-neuronal cells; transformed non-neuronal cells; non-neuronal tumor cells; stably and transiently transfected non-neuronal cells and further include, yet are not limited to, mammalian, murine, rat, primate and human non-neuronal cells. Non-neuronal cells useful in aspects of the invention further include, without limitation, any of the following primary or established cells: anterior pituitary cells; adrenal cells, such as. e.g., chromaffin cells of the adrenal medulla; pancreatic cells, such as. e.g. pancreatic acinar cells, pancreatic islet P cells and insulinoma HIT or INS-1 cells; ovarian cells, such as. e.g., steroid-producing ovarian cells; kidney cells, such as. e.g. inner medullary collecting duct (IMCD) cells; stomach cells, such as, e.g. enterochromaffin cells; blood cells, such as. e.g. eurythrocytes, leucocytes, platelets, neutrophils, eosinophils, mast cells; epithelial cells, such as. e.g., those of the apical plasma membrane; fibroblasts; thyroid cells; chondrocytes; muscle cells; hepatocytes; glandular cells such as, e.g., pituitary cells, adrenal cells, chromaffin cells; and cells involved in glucose transporter (GLUT4) translocation. Thus, in an embodiment, a cell capable of BoNT/A intoxication can be a non-neuronal cell. In aspects of this embodiment, a non-neuronal cell can be from a primary or established non-neuronal cell line from the, e.g. anterior pituitary cells, adrenal cells, pancreatic cells, ovarian cells, kidney cells, stomach cells, blood cells, epithelial cells, fibroblasts, thyroid cells, chondrocytes, muscle cells, hepatocytes and glandular cells.

As non-limiting examples, cells useful for detecting BoNT/A activity according to a method disclosed in the present specification can include, a primary or established non-neuronal cell that contains an exogenous FGFR3, such as, e.g., a chromaffin cell that contains an exogenous FGFR3 or pancreatic acinar cell that contains an exogenous FGFR3; a primary neuronal cell that contains an exogenous FGFR3.

As discussed above, cells useful in the invention include neuronal and non-neuronal cells that express low or undetectable levels of endogenous receptor but which have been transfected with, or otherwise engineered to express, one or more exogenous nucleic acid molecules encoding one or more FGFR3s. Cells useful in aspects of the present invention further include, without limitation, transformed, tumor or other cells which over-express one or more exogenous FGFR3s. It is understood that the over-expressed receptor can be a wild type form of the receptor or can include one or more amino acid modifications as compared to the wild type receptor, with the proviso that the process of BoNT/A intoxication can still occur. As a non-limiting example, cells useful for detecting BoNT/A activity encompass those which express or over-express an exogenous mammalian FGFR3, such as, e.g. a human FGFR3, a bovine FGFR3, a rat FGFR3 or a mouse FGFR3. As another non-limiting example, cells useful for detecting BoNT/A activity encompass those which express or over-express an exogenous bird FGFR3, such as, e.g. chicken FGFR3. As another non-limiting example, cells useful for detecting BoNT/A activity encompass those which express or over-express an exogenous amphibian FGFR3, such as, e.g., a newt FGFR3 or a frog FGFR3. As another non-limiting example, cells useful for detecting BoNT/A activity encompass those which express or over-express an exogenous fish FGFR3, such as, e.g. a zebrafish FGFR3.

Thus, in an embodiment, a cell capable of BoNT/A intoxication can be a cell stably expressing an exogenous FGFR3. In aspects of this embodiment, a cell capable of BoNT/A intoxication can be a cell stably expressing an exogenous mammalian FGFR3, such as, e.g. a human FGFR3, a bovine FGFR3, a rat FGFR3 or a mouse FGFR3. In other aspects of this embodiment, a cell capable of BoNT/A intoxication can be a cell stably expressing an exogenous bird FGFR3, such as, e.g., chicken FGFR3. In other aspects of this embodiment, a cell capable of BoNT/A intoxication can be a cell stably expressing an exogenous amphibian FGFR3, such as, e.g., a newt FGFR3 or a frog FGFR3. In other aspects of this embodiment, a cell capable of BoNT/A intoxication can be a cell stably expressing an exogenous fish FGFR3, such as, e.g. a zebrafish FGFR3.

Aspects of the present invention provide, in part, detecting the presence of BoNT/A activity of said contacted cell relative to a control cell, where a difference in said BoNT/A activity of said contacted cell as compared to said control cell is indicative of BoNT/A activity. As used herein, the term "control cell" means a cell of the same or similar type as the contacted cell and grown under the same conditions but which is not contacted with any sample or is contacted with a defined negative sample or a defined positive sample. One skilled in the art understands that a variety of control cells are useful in the methods disclosed in the present specification and that a control cell can be a positive control cell or a negative control cell. A control cell can be, for example, a negative control cell such as a similar or identical cell containing the same or similar FGFR3 that is contacted with a similar, defined negative sample, which is known to lack active BoNT/A, or that is not contacted with any sample. A control cell also can be, for example, a positive control cell such as a similar or identical cell containing the same or similar FGFR3 contacted with a defined positive sample, which is known to include active BoNT/A.

A wide variety of assays can be used to determine the presence of BoNT/A activity, including direct and indirect assays for toxin uptake. Assays that determine BoNT/A binding or uptake properties can be used to assess BoNT/A activity. Such assays include, without limitation, cross-linking assays using labeled BoNT/A, such as, e.g., BoNT/A-SBED, see, e.g. Example II of the present specification and [125] BoNT/A, see, e.g., Noriko Yokosawa et al., Binding of *Clostridium botulinum* type C neurotoxin to different neuroblastoma cell lines, 57(1) Infect. Immun. 272-277 (1989); Noriko Yokosawa et al., Binding of botulinum type C1, D and E neurotoxins to neuronal cell lines and synaptosomes, 29(2) Toxicon 261-264 (1991); and Tei-ichi Nishiki et al., Identification of protein receptor for *Clostridium botulinum* type B neurotoxin in rat brain synaptosomes, 269(14) J. Biol. Chem. 10498-10503 (1994). Other non-limiting assays include immunocytochemical assays that detect toxin binding using labeled or unlabeled antibodies, see, e.g., Atsushi Nishikawa et al., The receptor and transporter for internalization of *Clostridium botulinum* type C progenitor toxin into HT-29 cells, 319(2) Biochem. Biophys. Res. Commun. 327-333 (2004) and immunoprecipitation assays, see, e.g. Yukako Fujinaga et al., Molecular characterization of binding subcomponents of *Clostridium botulinum* type C progenitor toxin for intestinal epithelial cells and erythrocytes, 150(Pt 5) Microbiology 1529-1538 (2004). Antibodies useful for these assays include, without limitation, antibodies selected against a BoNT/A, antibodies selected against a BoNT/A receptor, such as, e.g., FGFR3, antibodies selected against a ganglioside, such as, e.g., GD1a, GD1b, GD3, GQ1b, or GT1b and selected against a test compound, such as, e.g., a molecule that selectively binds a BoNT/A receptor wherein selective binding modulates BoNT/A activity. If the antibody is labeled, the binding of the molecule can be detected by various means, including Western blotting, direct microscopic observation of the cellular location of the antibody, measurement of cell or substrate-bound antibody following a wash step, or electrophoresis, employing techniques well-known to those of skill in the art. If the antibody is unlabeled, one may employ a labeled secondary antibody for indirect detection of the bound molecule, and detection can proceed as for a labeled antibody. It is understood that these and similar assays that determine BoNT/A uptake properties or characteristics can be useful in detecting BoNT/A activity.

Assays that monitor the release of a molecule after exposure to BoNT/A can also be used to assess for the presence of BoNT/A activity. In these assays, inhibition of the molecule's release would occur in cells expressing a FGFR3 after BoNT/A treatment. As a non-limiting example the inhibition of insulin release assay disclosed in the present specification can monitor the release of a molecule after exposure to BoNT/A and thereby be useful in assessing whether a molecule selectively binds a BoNT/A receptor (see Example I). Other non-limiting assays include methods that measure inhibition of radio-labeled catecholamine release from neurons, such as, e.g., [$^3$H] noradrenaline or [$^3$H] dopamine release, see e.g., A Fassio et al., Evidence for calcium-dependent vesicular transmitter release insensitive to tetanus toxin and botulinum toxin type F, 90(3) Neuroscience 893-902 (1999); and Sara Stigliani et al., The sensitivity of catecholamine release to botulinum toxin C1 and E suggests selective targeting of vesicles set into the readily releasable pool, 85(2) J. Neurochem. 409-421 (2003), or measures catecholamine release using a fluorometric procedure, see, e.g., Anton de Paiva et al., A role for the interchain disulfide or its participating thiols in the internalization of botulinum neurotoxin A revealed by a toxin derivative that binds to ecto-acceptors and inhibits transmitter release intracellularly, 268(28) J. Biol. Chem. 20838-20844 (1993); Gary W. Lawrence et al., Distinct exocytotic responses of intact and permeabilised chromaffin cells after cleavage of the 25-kDa synaptosomal-associated protein (SNAP-25) or synaptobrevin by botulinum toxin A or B, 236(3) Eur. J. Biochem. 877-886 (1996); and Patrick Foran et al., Botulinum neurotoxin C1 cleaves both syntaxin and SNAP-25 in intact and permeabilized chromaffin cells: correlation with its blockade of catecholamine release, 35(8) Biochemistry 2630-2636 (1996); and methods that measure inhibition of hormone release from endocrine cells, such as, e.g. anterior pituitary cells or ovarian cells. It is understood that these and similar assays for molecule release can be useful in assessing BoNT/A activity.

As non-limiting examples, an inhibition of insulin release assay can be used to determine the presence of BoNT/A activity in cells containing a FGFR3 and capable of secreting insulin; an inhibition of noradrenaline release assay can be used to determine BoNT/A activity in cells containing a FGFR3 and capable of secreting noradrenaline; and an inhibition of estrogen release assay can be used to determine BoNT/A activity in cells containing a FGFR3 and capable of secreting estrogen.

Assays that detect the cleavage of a BoNT/A substrate after exposure to BoNT/A can also be used to assess for the presence of BoNT/A activity. In these assays, generation of a BoNT/A cleavage-product would be detected after BoNT/A treatment. As a non-limiting example the SNAP-25 cleavage assay disclosed in the present specification can detect the cleavage of a BoNT/A substrate after exposure to BoNT/A and thereby be useful in assessing BoNT/A activity (see Example I). Other non-limiting methods useful to detect the cleavage of a BoNT/A substrate after exposure to BoNT/A are described in, e.g., Lance E. Steward et al., FRET Protease Assays for Botulinum Serotype A/E Toxins, U.S. Patent Publication No. 2003/0143650 (Jul. 31, 2003); and Ester Femandez-Salas et al., Cell-based Fluorescence Resonance Energy Transfer (FRET) Assays for Clostridial Toxins, U.S. Patent Publication 2004/0072270 (Apr. 15, 2004). It is understood that these and similar assays for BoNT/A substrate cleavage can be useful in assessing BoNT/A activity.

As non-limiting examples, western blot analysis using an antibody that recognizes BoNT/A SNAP-25-cleaved product can be used to determine the presence of BoNT/A activity. Examples of anti-SNAP-25 antibodies useful for these assays include, without limitation, rabbit polyclonal anti-SNAP25$_{197}$ antiserum pAb anti-SNAP25197 #1 (Allergan, Inc., Irvine, Calif.), mouse monoclonal anti-SNAP-25 antibody SMI-81 (Sternberger Monoclonals, Lutherville, Md.), mouse monoclonal anti-SNAP-25 antibody CI 71.1 (Synaptic Systems, Goettingen, Germany), mouse monoclonal anti-SNAP-25 antibody CI 71.2 (Synaptic Systems, Goettingen, Germany), mouse monoclonal anti-SNAP-25 antibody SP12 (Abcam, Cambridge, Mass.), rabbit polyclonal anti-SNAP-25 antiserum (Synaptic Systems, Goettingen, Germany), and rabbit polyclonal anti-SNAP-25 antiserum (Abcam, Cambridge, Mass.).

The methods disclosed in the present specification include, in part, a sample. As used herein, the term "sample" means any biological matter that contains or potentially contains an active BoNT/A. A variety of samples can be assayed according to a method disclosed in the present specification including, without limitation, purified, partially purified, or unpurified BoNT/A; recombinant single chain or di-chain toxin with a naturally or non-naturally occurring sequence; recombinant BoNT/A with a modified protease specificity; recombinant BoNT/A with an altered cell specificity; chimeric toxin containing structural elements from multiple BoNT/A species or subtypes; bulk BoNT/A; formulated BoNT/A product; and foods; cells or crude, fractionated or partially purified cell lysates, for example, engineered to include a recombinant nucleic acid encoding a BoNT/A; bacterial, baculoviral and yeast lysates; raw, cooked, partially cooked or processed foods; beverages; animal feed; soil samples; water samples; pond sediments; lotions; cosmetics; and clinical formulations. It is understood that the term sample encompasses tissue samples, including, without limitation, mammalian tissue samples, livestock tissue samples such as sheep, cow and pig tissue samples; primate tissue samples; and human tissue samples. Such samples encompass, without limitation, intestinal samples such as infant intestinal samples, tissue samples obtained from a wound. Other such samples include mammalian tissue, mammalian saliva, mammalian excretions and mammalian feces. As non-limiting examples, a method of the invention can be useful for detecting the presence or activity of a BoNT/A in a food or beverage sample; to assay a sample from a human or animal, for example, exposed to a BoNT/A or having one or more symptoms of a BoNT/A exposure; to follow activity during production and purification of BoNT/A; or to assay formulated BoNT/A products such as pharmaceuticals or cosmetics.

It is envisioned that a wide variety of processing formats can be used in conjunction with the methods disclosed present specification, including, without limitation, manual processing, partial automated-processing, semi-automated-processing, full automated-processing, high throughput processing, high content processing, and the like or any combination thereof.

Other aspect of the present invention provide methods of reducing BoNT/A activity in a human comprising administering to said human a pharmaceutical composition comprising a molecule that selectively binds a FGFR3 wherein said selective binding reduces the ability of BoNT/A to bind to said FGFR3. In is envisioned that any molecule that can selectively bind to a FGFR3 in a manner that prevents BoNT/A binding to that same FGFR3 can be useful, including, without limitation, an anti-FGFR3 antibody, an FGF or an FGF agonist. In addition, a FGFR3, a FGFR3 fragment retaining BoNT/A selective binding activity, or peptidomimetic thereof can also be useful. Molecules that selectively binds a FGFR3, and thus useful in methods of reducing BoNT/A activity are described in, e.g. Avner Yayon et al., Antibodies that block receptor protein tyrosone kinase activation, methods of screening for and using thereof, International Publication No. WO 02/102972 (Dec. 27, 2002); Avner Yayon et al., Antibodies that block receptor protein tyrosone kinase activation, methods of screening for and using thereof, International Publication No. WO 02/102973 (Dec. 27, 2002); and Elisabeth Thomassen-Wolf et al., Antibodies that block receptor protein tyrosone kinase activation, methods of screening for and using thereof, International Publication No. WO 02/102854 (Dec. 27, 2002)

Aspects of the present invention provide, in part, a method of reducing BoNT/A activity in a human by administering a pharmaceutical composition comprising a molecule that selectively binds a FGFR3. The administered composition can be formulated in a variety of pharmaceutically acceptable media, as described below. An effective dose of a composition disclosed in the present specification will depend upon the particular molecule selected, the route administration, and the particular characteristics of the human or other mammal, such as age, weight, general health and the like. An effective dose can be determined in an animal model prior to administration to humans. Compositions useful in aspects of the invention can be administered by a variety of routes to stimulate an immune response. As a non-limiting example, oral tolerance is well-recognized in the art (see, for example, Weiner, *Hospital Practice*, pp. 53-58 (Sep. 15, 1995). Those skilled in the art can readily determine for a particular composition, a suitable pharmacological composition, an appropriate antigen payload; route of administration; volume of dose; and pharmaceutical regimen useful in a particular animal, for example, humans.

As disclosed herein a pharmaceutical composition is administered to a human or other mammal to reduce BoNT/A activity. As used herein, the term "reduce," when used in reference to administering to a human or other mammal an effective amount of a pharmaceutical composition, means reducing a symptom of a condition characterized by exposure BoNT/A activity, or delaying or preventing onset of a symptom of a condition characterized by exposure to BoNT/A activity in the human or other mammal. For example, the term "reducing" can mean reducing a symptom of a condition characterized by exposure to BoNT/A activity by at least 30%, 40%, 60%, 70%, 80%, 90% or 100%. The effectiveness of a pharmaceutical composition in treating a condition characterized by exposure to BoNT/A activity can be determined by observing one or more clinical symptoms or physiological indicators associated with the condition. An improvement in a condition characterized by exposure to BoNT/A activity also can be indicated by a reduced need for a concurrent therapy. Those of skill in the art will know the appropriate symptoms or indicators associated with specific conditions and will know how to determine if a human or other mammal is a candidate for treatment with a pharmaceutical composition disclosed in the present specification. In particular, it is understood that those skilled in the art will be able to determine if a condition if characterized by exposure BoNT/A activity, for example, by comparison of levels of BoNT/A activity from the human or other mammal with a normal control cells.

The appropriate effective amount to be administered for a particular application of the methods can be determined by those skilled in the art, using the guidance provided herein. For example, an effective amount can be extrapolated from assays as described herein above. One skilled in the art will recognize that the condition of the patient can be monitored throughout the course of therapy and that the effective amount of a composition that is administered can be adjusted accordingly.

A pharmaceutical composition useful in aspects of the invention generally is administered in a pharmaceutical acceptable composition. As used herein, the term "pharmaceutically acceptable" refer to any molecular entity or composition that does not produce an adverse, allergic or other untoward or unwanted reaction when administered to a human or other mammal. As used herein, the term "pharmaceutically acceptable composition" refers to a therapeutically effective concentration of an active ingredient. A pharmaceutical composition may be administered to a patient alone, or in combination with other supplementary active ingredients, agents, drugs or hormones. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilizate, tablet, pill, pellet, capsule, powder, syrup, elixir or any other dosage form suitable for administration.

It is also envisioned that a pharmaceutical composition disclosed in the present specification can optionally include a pharmaceutically acceptable carriers that facilitate processing of an active ingredient into pharmaceutically acceptable compositions. As used herein, the term "pharmacologically acceptable carrier" refers to any carrier that has substantially no long term or permanent detrimental effect when administered and encompasses terms such as "pharmacologically acceptable vehicle, stabilizer, diluent, auxiliary or excipient." Such a carrier generally is mixed with an active compound, or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g. distilled, deionized water, saline; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in PHARMACEUTICAL DOSAGE FORMS AND DRUG DELIVERY SYSTEMS (Howard C. Ansel et al., eds., Lippincott Williams & Wilkins Publishers, 7th ed. 1999); REMINGTON: THE SCIENCE AND PRACTICE OF PHARMACY (Alfonso R. Gennaro ed., Lippincott, Williams & Wilkins, 20$^{th}$ ed. 2000); GOODMAN & GILMAN'S THE PHARMACOLOGICAL BASIS OF THERAPEUTICS (Joel G. Hardman et al., eds., McGraw-Hill Professional, 10th ed. 2001); and HANDBOOK OF PHARMACEUTICAL EXCIPIENTS (Raymond C. Rowe et al., APhA Publications, 4$^{th}$ edition 2003). These protocols are routine procedures and any modifications are well within the scope of one skilled in the art and from the teaching herein.

It is further envisioned that a pharmaceutical composition disclosed in the present specification can optionally include, without limitation, other pharmaceutically acceptable components, including, without limitation, buffers, preservatives, tonicity adjusters, salts, antioxidants, physiological substances, pharmacological substances, bulking agents, emulsifying agents, wetting agents, sweetening or flavoring agents, and the like. Various buffers and means for adjusting pH can be used to prepare a pharmaceutical composition disclosed in the present specification, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate and a stabilized oxy chloro composition, for example, PURITE®. Tonicity adjustors useful in a pharmaceutical composition include, without limitation, salts such as, e.g. sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition useful in the invention.

A pharmaceutical composition useful in a method of the disclosure is administered to a human or other mammal in an effective amount. Such an effective amount generally is the minimum dose necessary to achieve the desired therapeutic effect, which can be, for example, that amount roughly necessary to reduce the symptoms associated with exposure to BoNT/A activity. For example, the term "effective amount" when used with respect to treating exposure to BoNT/A activity can be a dose sufficient to the symptoms, for example, by at least 30%, 40%, 50%, 60%, 70%, 80%, 90% or 100%. Such a dose generally is in the range of 0.1-1000 mg/day and can be, for example, in the range of 0.1-500 mg/day, 0.5-500 mg/day, 0.5-100 mg/day, 0.5-50 mg/day, 0.5-20 mg/day, 0.5-10 mg/day or 0.5-5 mg/day, with the actual amount to be administered determined by a physician taking into account the relevant circumstances including the severity of the BoNT/A exposure, the age and weight of the patient, the patient's general physical condition, the cause of the BoNT/A exposure and the route of administration. Where repeated administration is used, the frequency of administration depends, in part, on the half-life of the pharmaceutical composition. Suppositories and extended release formulations can be useful in the invention and include, for example, dermal patches, formulations for deposit on or under the skin and formulations for intramuscular injection. It is understood that slow-release formulations also can be useful in the methods of the invention. The subject receiving the pharmaceutical composition can be any mammal or other vertebrate capable of experiencing exposure to BoNT/A activity, for example, a human, primate, horse, cow, dog, cat or bird.

Various routes of administration can be useful for reducing BoNT/A activity according to a method of the invention. A pharmaceutical composition useful in the methods of the invention can be administered to a mammal by any of a variety of means depending, for example, on the type and location of BoNT/A exposure to be treated, the pharmaceutical composition, or other compound to be included in the composition, and the history, risk factors and symptoms of the subject. Routes of administration suitable for the methods of the invention include both systemic and local administration. As non-limiting examples, a pharmaceutical composition useful for reducing BoNT/A activity can be administered orally or by subcutaneous pump; by dermal patch; by intravenous, subcutaneous or intramuscular injection; by topical drops, creams, gels or ointments; as an implanted or injected extended release formulation; as a bioerodible or non-bioerodible delivery system; by subcutaneous minipump or other implanted device; by intrathecal pump or injection; or by epidural injection. An exemplary list of biodegradable polymers and methods of use are described in, e.g., HANDBOOK OF BIODEGRADABLE POLYMERS (Abraham J. Domb et al., eds., Overseas Publishers Association, 1997); CONTROLLED DRUG DELIVERY: DESIGNING TECHNOLOGIES FOR THE FUTURE (Kinam Park & Randy J. Mrsny eds., American Chemical Association, 2000); Vernon G. Wong, Method for Reducing or Preventing Transplant Rejection in the Eye and Intraocular Implants for Use Therefor, U.S. Pat. No. 6,699,493 (Mar. 2, 2004); Vernon G. Wong & Mae W. L. Hu, Methods for Treating Inflammation-mediated Conditions of the Eye, U.S. Pat. No. 6,726,918 (Apr. 27, 2004); David A. Weber et al., Methods and Apparatus for Delivery of Ocular Implants, U.S. Patent Publication No. US2004/0054374 (Mar. 18, 2004); Thierry Nivaggioli et al., Biodegradable Ocular Implant, U.S. Patent Publication No. US2004/0137059 (Jul. 15, 2004). It is understood that the frequency and duration of dosing will be dependent, in part, on the relief desired and the half-life of the tolerogizing composition.

In particular embodiments, a method of the invention is practiced by peripheral administration of a pharmaceutical composition. As used herein, the term "peripheral administration" or "administered peripherally" means introducing an agent into a subject outside of the central nervous system. Peripheral administration encompasses any route of administration other than direct administration to the spine or brain. As such, it is clear that intrathecal and epidural administration as well as cranial injection or implantation are not within the scope of the term "peripheral administration" or "administered peripherally."

Peripheral administration can be local or systemic. Local administration results in significantly more of a pharmaceutical composition being delivered to and about the site of local administration than to regions distal to the site of administration. Systemic administration results in delivery of a pharmaceutical composition to essentially the entire peripheral nervous system of the subject and may also result in delivery to the central nervous system depending on the properties of the composition.

Routes of peripheral administration useful in the methods of the invention encompass, without limitation, oral administration, topical administration, intravenous or other injection, and implanted minipumps or other extended release devices or formulations. A pharmaceutical composition useful in the invention can be peripherally administered, for example, orally in any acceptable form such as in a tablet, liquid, capsule, powder, or the like; by intravenous, intraperitoneal, intramuscular, subcutaneous or parenteral injection; by transdermal diffusion or electrophoresis; topically in any acceptable form such as in drops, creams, gels or ointments; and by minipump or other implanted extended release device or formulation.

Other aspect of the present invention provide methods of screening for a molecule able to compete with BoNT/A for selective binding to cells susceptible to BoNT/A intoxication by contacting said sample with a composition comprising an FGFR3 and detecting whether said molecule selectively binds said FGFR3, wherein selective binding of said molecule to said FGFR3 indicates that said molecule is able to compete with BoNT/A for selective binding to cells susceptible to BoNT/A intoxication, and wherein if said molecule is BoNT/A, said method does not comprise an $LD_{50}$ assay. As used herein, the term "selective" binding means that a binding agent is able to bind its target under physiological conditions, or in vitro conditions substantially approximating physiological conditions, to a statistically significantly greater degree (i.e., has a smaller $K_d$ or dissociation constant) than to other, non-target molecules on the surface of the neural cell. "$K_d$" is the molar concentration of the binding agent at which half the target molecules are bound by the binding agent. As used herein, the term "$LD_{50}$ assay" means an live animal-based in vivo assay of neurotoxin activity comprising detecting the dose of neurotoxin at which 50% of treated animals die, see, e.g., the Mouse Protection Assay (MPA), Charles L. Hatheway & Carol Dang, *Immunogenicity of the Neurotoxins of Clostridium botulinum,* 93-107 (Neurological Disease and Therapy-THERAPY WITH BOTULINUM TOXIN, Joseph Jankovic & Mark Hallett eds., Marcel Dekker, 1994).

It is envisioned that any and all assay conditions suitable for screening for a molecule able to compete with BoNT/A for selective binding to cells susceptible to BoNT/A intoxication can be useful, including, e.g., in vitro and in vivo assays. In addition, it is also foreseen that a wide variety of processing formats can be used in conjunction with the methods disclosed present specification, including, without limitation, manual processing, partial automated-processing, semi-automated-processing, full automated-processing, high throughput processing, high content processing, and the like or any combination thereof.

As disclosed above, any of the methods useful for detecting BoNT/A activity disclosed in the present specification and any of the compositions useful for practicing the methods useful for detecting BoNT/A activity disclosed in the present specification can be can be useful in screening for a molecule that competes with BoNT/A for the selectively binding to a FGFR3. Thus, in aspect of this embodiment, a FGFR3 can be encoded by the nucleic acid molecule from a mammalian FGFR3, such as, e.g., a human FGFR3, a bovine FGFR3, a rat FGFR3 or a mouse FGFR3; a bird FGFR3, such as, e.g., chicken FGFR3; an amphibian FGFR3, such as, e.g., a newt FGFR3 or a frog FGFR3; and a fish FGFR3, such as, e.g. a zebrafish FGFR3. In another aspect of this embodiment, a FGFR3 can be a mammalian FGFR3, such as, e.g. a human FGFR3, a bovine FGFR3, a rat FGFR3 or a mouse FGFR3; a bird FGFR3, such as, e.g. chicken FGFR3; an amphibian FGFR3, such as, e.g., a newt FGFR3 or a frog FGFR3; and a fish FGFR3, such as, e.g., a zebrafish FGFR3. In another aspect of this embodiment, a FGFR3 useful in screening for a molecule that competes with BoNT/A for the selectively binding to the FGFR3 can be transiently or stably contained in a cell. In another aspect of this embodiment, a composition useful in screening for a molecule that competes with BoNT/A for the selectively binding to a FGFR3 comprises a FGFR3 and optionally a G1b polysialoganglioside, such as, e.g., GD1a, GD1b, GD3, GQ1b, or GT1b.

In another aspect of this embodiment, a cell can include cells, such as, e.g., neuronal cells including, without limitation, primary neuronal cells; immortalized or established neuronal cells; transformed neuronal cells; neuronal tumor cells; stably and transiently transfected neuronal cells expressing a FGFR3, and further include, yet are not limited to, mammalian, murine, rat, primate and human neuronal cells. Other aspects of this embodiment include cells from, such as, e.g. neuronal cell lines including, without limitation, neuroblastoma cell lines, neuronal hybrid cell lines, spinal cord cell lines, central nervous system cell lines, cerebral cortex cell lines, dorsal root ganglion cell lines, hippocampal cell lines and pheochromocytoma cell lines. Non-limiting examples of neuronal cell lines include, e.g. neuroblastoma cell lines BE(2)-C, BE(2)-M17, C1300, CHP-212, CHP-126, IMR 32, KELLY, LA-N-2, MC-IXC, MHH-NB-11, N18Tg2, N1E-115, N4TG3, Neuro-2A, NB41A3, NS20Y, SH-SY5Y, SIMA, SK-N-DZ, SK-N-F1, SK-N-MC and SK-N-SH; neuroblastoma/glioma hybrid cell lines N18, NG108-15 and NG115-401L; neuroblastoma/motor neuron hybrid cell lines NSC-19 and NSC-32; neuroblastoma/root ganglion neuron hybrid cell lines F11, ND-E, ND-U1, ND7/23, ND8/34 and ND27; the neuroblastoma/hippocampal neuron hybrid cell line HN-33; spinal cord cell lines TE 189.T and M4b; cerebral cortex cell lines CNh, HCN-1a and HCN-2; dorsal root ganglia cell line G4b; hippocampal cell lines HT-4, HT-22 and HN33; FGFR3 expressing cell lines H929, JIM-3, KMS-11, KMS-18, LB278, LB375, LB1017, LB2100, LP-1, OPM-2, PCL1 and UTMC-2. In further aspects of this embodiment, an FGFR3 expressing cell can be, e.g., H929, JIM-3, KMS-11, KMS-18, LB278, LB375, LB1017, LB2100, LP-1, OPM-2, PCL1 UTMC-2, B9, TC, L6 and CFK2. Other aspects of this embodiment include cells, such as, e.g., non-neuronal cells including, without limitation, primary non-neuronal cells; immortalized or established non-neuronal cells; transformed non-neuronal cells; non-neuronal tumor cells; stably and transiently transfected non-neuronal cells expressing a FGFR3, and further include, yet are not limited to, mammalian, murine, rat, primate and human non-neuronal cells. Other aspects of this embodiment include cells, such as, e.g., non-neuronal cells useful in aspects of the invention further include, without limitation, anterior pituitary cells; adrenal cells, pancreatic cells, ovarian cells, kidney cells, stomach cell, blood cells, epithelial cells, fibroblasts, thyroid cells, chondrocytes, muscle cells, hepatocytes, glandular cells and cells involved in glucose transporter (GLUT4) translocation.

The molecule to be tested in the screening method may be a "small" organic compound of synthetic origin, or may be a macromolecule (either of synthetic or biological origin) including without limitation, a polypeptide, such as, e.g. a growth factor, a neurotoxin, a modified neurotoxin, an antibody or an antibody derivative; a nucleic acid, such as, e.g. a nucleic acid aptomer; and a polysaccharide, such as, e.g., a ganglioside or a lectin. In one embodiment, the molecule is a synthetic molecule designed based on the tertiary structure and three dimensional conformation of FGF or an antibody that inhibits BoNT/A binding to a FGFR3. Such SAR (structure/activity relationship) analysis is routine in the art of medicinal chemistry, among other fields.

A wide variety of assays can be used to determine whether a molecule selectively binds a FGFR3, including direct and indirect assays for toxin uptake. Assays that determine BoNT/A binding or uptake properties can be used to assess whether a molecule selectively binds a FGFR3. Such assays include, without limitation, cross-linking assays using labeled BoNT/A, such as, e.g., BoNT/A-SBED, see, e.g., Example II of the present specification and [$^{125}$I] BoNT/A, see, e.g. Noriko Yokosawa et al., Binding of *Clostridium botulinum* type C neurotoxin to different neuroblastoma cell lines, 57(1) Infect. Immun. 272-277 (1989); Noriko Yokosawa et al., Binding of botulinum type C1, D and E neurotoxins to neuronal cell lines and synaptosomes, 29(2) Toxicon 261-264 (1991); and Tei-ichi Nishiki et al., Identification of protein receptor for *Clostridium botulinum* type B neurotoxin in rat brain synaptosomes, 269(14) J. Biol. Chem. 10498-10503 (1994). Other non-limiting assays include immunocytochemical assays that detect toxin binding using labeled or unlabeled antibodies, see, e.g. Atsushi Nishikawa et al., The receptor and transporter for internalization of *Clostridium botulinum* type C progenitor toxin into HT-29 cells, 319(2) Biochem. Biophys. Res. Commun. 327-333 (2004) and immunoprecipitation assays, see, e.g., Yukako Fujinaga et al., Molecular characterization of binding subcomponents of *Clostridium botulinum* type C progenitor toxin for intestinal epithelial cells and erythrocytes, 150(Pt 5) Microbiology 1529-1538 (2004). Antibodies useful for these assays include, without limitation, antibodies selected against a BoNT/A, antibodies selected against a BoNT/A receptor, such as, e.g., FGFR3, antibodies selected against a ganglioside, such as, e.g., GD1a, GD1b, GD3, GQ1b, or GT1b and selected against a test compound, such as, e.g., a molecule that selectively binds a BoNT/A receptor wherein selective binding modulates BoNT/A activity. If the antibody is labeled, the binding of the molecule can be detected by various means, including Western blotting, direct microscopic observation of the cellular location of the antibody, measurement of cell or substrate-bound antibody following a wash step, or electrophoresis, employing techniques well-known to those of skill in the art. If the antibody is unlabeled, one may employ a labeled secondary antibody for indirect detection of the bound molecule, and detection can proceed as for a labeled antibody. It is understood that these and similar assays that determine BoNT/A uptake properties or characteristics can be useful in selecting a neuron or other cells useful in aspects of the invention.

Assays that monitor the release of a molecule after exposure to BoNT/A can also be used to assess whether a molecule selectively binds a FGFR3. In these assays, inhibition of the molecule's release would occur in cells expressing a FGFR3 after BoNT/A treatment. As a non-limiting example the inhibition of insulin release assay disclosed in the present specification can monitor the release of a molecule after exposure to BoNT/A and thereby be useful in assessing whether a molecule selectively binds a FGFR3 (see Example I). Other non-limiting assays include methods that measure inhibition of radio-labeled catecholamine release from neurons, such as, e.g., [$^3$H] noradrenaline or [$^3$H] dopamine release, see e.g., A Fassio et al., Evidence for calcium-dependent vesicular transmitter release insensitive to tetanus toxin and botulinum toxin type F, 90(3) Neuroscience 893-902 (1999); and Sara Stigliani et al., The sensitivity of catecholamine release to botulinum toxin Cl and E suggests selective targeting of vesicles set into the readily releasable pool, 85(2) J. Neurochem. 409-421 (2003), or measures catecholamine release using a fluorometric procedure, see, e.g., Anton de Paiva et al., A role for the interchain disulfide or its participating thiols in the internalization of botulinum neurotoxin A revealed by a toxin derivative that binds to ecto-acceptors and inhibits transmitter release intracellularly, 268(28) J. Biol. Chem. 20838-20844 (1993); Gary W. Lawrence et al., Distinct exocytotic responses of intact and permeabilised chromaffin cells after cleavage of the 25-kDa synaptosomal-associated protein (SNAP-25) or synaptobrevin by botulinum toxin A or B, 236(3) Eur. J. Biochem. 877-886 (1996); and Patrick Foran et al., Botulinum neurotoxin Cl cleaves both syntaxin and SNAP-25 in intact and permeabilized chromaffin cells: correlation with its blockade of catecholamine release, 35(8) Biochemistry 2630-2636 (1996); and methods that measure inhibition of hormone release from endocrine cells, such as, e.g., anterior pituitary cells or ovarian cells. It is understood that these and similar assays for molecule release can be useful in assessing whether a molecule selectively binds a FGFR3.

As non-limiting examples, an inhibition of insulin release assay can be used to test whether a molecule selectively binds a FGFR3 in a FGFR3 containing cells capable of secreting insulin; an inhibition of noradrenaline release assay using can be used to test whether a molecule selectively binds a FGFR3 in a FGFR3 containing cells capable of secreting noradrenaline; and an inhibition of estrogen release assay can be used to assay whether a molecule selectively binds a FGFR3 in a FGFR3 containing cells and capable of secreting estrogen.

Assays that detect the cleavage of a BoNT/A substrate after exposure to BoNT/A can also be used to assess whether a molecule selectively binds a FGFR3. In these assays, generation of a BoNT/A cleavage-product would be detected in cells expressing a FGFR3 after BoNT/A treatment. As a non-limiting example the SNAP-25 cleavage assay disclosed in the present specification can detect the cleavage of a BoNT/A substrate after exposure to BoNT/A and thereby be useful in assessing whether a molecule selectively binds a BoNT/A receptor (see Example I). Other non-limiting methods useful to detect the cleavage of a BoNT/A substrate after exposure to BoNT/A are described in, e.g. Lance E. Steward et al., FRET Protease Assays for Botulinum Serotype A/E Toxins, U.S. Patent Publication No. 2003/0143650 (Jul. 31, 2003); and Ester Femandez-Salas et al., Cell-based Fluorescence Resonance Energy Transfer (FRET) Assays for Clostridial Toxins, U.S. Patent Publication 2004/0072270 (Apr. 15, 2004). It is understood that these and similar assays for BoNT/A substrate cleavage can be useful in assessing whether a molecule selectively binds a FGFR3.

As non-limiting examples, western blot analysis using an antibody that recognizes BoNT/A SNAP-25-cleaved product can be used to assay whether a molecule selectively binds a FGFR3. Examples of anti-SNAP-25 antibodies useful for these assays include, without limitation, rabbit polyclonal anti-SNAP25$_{197}$ antiserum pAb anti-SNAP25197 #1 (Allergan, Inc., Irvine, Calif.), mouse monoclonal anti-SNAP-25 antibody SMI-81 (Sternberger Monoclonals, Lutherville, Md.), mouse monoclonal anti-SNAP-25 antibody CI 71.1 (Synaptic Systems, Goettingen, Germany), mouse monoclonal anti-SNAP-25 antibody CI 71.2 (Synaptic Systems, Goettingen, Germany), mouse monoclonal anti-SNAP-25 antibody SP12 (Abcam, Cambridge, Mass.), rabbit polyclonal anti-SNAP-25 antiserum (Synaptic Systems, Goettingen, Germany), and rabbit polyclonal anti-SNAP-25 antiserum (Abcam, Cambridge, Mass.).

Assays that detect competitive binding of a molecule with BoNT/A for selective binding to a FGFR3 can also be used to assess whether a molecule selectively binds a FGFR3. In these assays, a reduction in BoNT/A activity would be detected as the amount of a molecule that competes with BoNT/A for selective binding to a BoNT/A would increase. In a non-limiting example, the competitive inhibition assay using FGF ligands disclosed in the present specification can be used to detect the competitive binding of a molecule with BoNT/A for selective binding to a FGFR3 and thereby be useful in assessing whether a molecule selectively binds a BoNT/A receptor (see Example II). Thus in one aspect of this embodiment, competitive binding assays using a FGFR3-binding molecule with BoNT/A for selective binding to a FGFR3 can be used to assess whether a molecule selectively binds a FGFR3.

Other aspect of the present invention provide methods of rendering a cell susceptible to cleavage of SNARE proteins by BoNT/A, comprising inducing said cell to express a FGFR3. Other aspect of the present invention provide methods of transiently rendering a cell susceptible to cleavage of SNARE proteins by BoNT/A, comprising transiently inducing said cell to express a FGFR3. Other aspect of the present invention provide methods of stably rendering a cell susceptible to cleavage of SNARE proteins by BoNT/A, comprising stably inducing said cell to express a FGFR3.

Other aspect of the present invention provide methods of marketing a neurotoxin capable of selectively binding to the same FGFR3 as BoNT/A comprising obtaining marketing approval from a governmental or regional regulatory authority for a therapeutic neurotoxin, wherein said neurotoxin is assayed for selective binding to a cell comprising contacting said neurotoxin with a composition comprising a FGFR3 and detecting whether said neurotoxin selectively binds said FGFR3, wherein selective binding of said neurotoxin to said FGFR3 indicates that said neurotoxin is able to selective binding to cells susceptible to BoNT/A intoxication and wherein if said molecule is BoNT/A, said method does not comprise an $LD_{50}$ assay; packaging said neurotoxin for sale in a manner consistent with the requirements of said regulatory authority, and selling said neurotoxin.

Other aspect of the present invention provide methods of marketing a neurotoxin capable of selectively binding to the same FGFR3 as BoNT/A comprising obtaining marketing approval from a governmental or regional regulatory authority for a therapeutic neurotoxin, wherein said neurotoxin is assayed for selective binding to a cell comprising contacting said neurotoxin to a cell that contains an exogenous FGFR3 wherein said contacted cell is capable of BoNT/A intoxication and detecting the presence of BoNT/A activity of said contacted cell relative to a control cell, where a difference in said BoNT/A activity of said contacted cell as compared to said control cell is indicative of BoNT/A activity; packaging said neurotoxin for sale in a manner consistent with the requirements of said regulatory authority, and selling said neurotoxin.

In another embodiment, the invention is drawn to a polypeptide comprising at least the $H_C$ region of BONT/A, which is produced from a bulk or formulated preparation wherein the bulk or formulated preparation is assayed for specific binding to neural cells using a method comprising contacting said polypeptide with a composition comprising FGFR3 receptor and, optionally, GT1b ganglioside, and detecting whether said polypeptide selectively binds FGFR3.

In another embodiment similar to the above aspect of the invention, the polypeptide comprises at least an FGFR3 binding domain, other than the $H_C$ domain of BoNT/A. Such a binding domain may comprise, for example, an FGF, such as FGF 1, FGF2, FGF4, FGF8 or FGF 9, or an anti-FGFR3 antibody. Further, the polypeptide may optionally contain a translocation domain such as the $H_N$ domain of BoNT/A. Additionally, the polypeptide will generally contain a clostridial neurotoxin light chain or variation thereof—the nature and/or source of the light chain can provide differences in the extent and half-life of the therapeutic effect of the polypeptide.

Thus, in this embodiment the claimed polypeptide is produced (which production may include purification, enzymatic treatment, and/or oxidation steps) from a bulk or formulation preparation. In one embodiment the preparation may be, for example, a cell lysate from fermentation of a BoNT/A-producing strain of *Clostridium botulinum*, or from a suitable mammalian, insect or bacterial host cell producing a recombinant version of BoNT/A. Such a bulk preparation may also be produced using cell-free transcription methodologies. In another embodiment the preparation may be purified BoNT/A formulated with associated stabilizing proteins, such as serum albumin. In each case, the preparation may comprise BoNT/A molecules which are denatured or otherwise incorrectly folded so as not to bind to the target cells. The potency and/or specific activity of the preparation, or of fractions purified from the preparation, can be detected by using the claimed assay method.

Alternatively, the polypeptide to be assayed may comprise only a portion of the entire BoNT/A molecule. For example, the bulk preparation may contain only the heavy chain of BoNT/A, as separate production of the heavy and light chains of the toxin may be a preferred way of avoiding accidental exposure to the neurotoxin by laboratory workers.

As another example of the above embodiment, the polypeptide may comprise a chimeric recombinant polypeptide which contains the Hc region of the heavy chain of BoNT/A (or some other FGFR3-binding moiety, such as FGF itself). The chimeric polypeptide comprises amino acid sequence regions additional to, or other than, those present in the wild-type BoNT/A BoNT/A molecule. For example, botulinum and tetanus toxins may be used as the basis for the creation of transport proteins, see, e.g., James Oliver Dolly et al., Modification of clostridial toxins for use as transport proteins, U.S. Pat. No. 6,203,794 (Mar. 20, 2001). The light chain of these transport proteins are generally either replaced by a therapeutic moiety or inactivated and coupled to such a therapeutic moiety. Additionally, chimeric neurotoxins can be made comprising polypeptides containing domains of more than one neurotoxin see, e.g., James Oliver Dolly et al., Activatable Recombinant Neurotoxins, International Publication No. WO 01/14570 (Mar. 1, 2001). Thus, this aspect of the invention also encompasses, as a embodiment, chimeric neurotoxins containing at least the $H_C$ domain of BoNT/A. Such molecules may be useful in modulating the time or extent of the inhibition of secretory vesicle release. Further, it may be desirable to target agents, such as therapeutic agents, to the extracellular surface of the neural cell membrane. Thus, such an agent may be joined (e.g., as a fusion protein or via post translational conjugation) to the $H_C$ portion of BoNT/A. In such a case the cell lysate or conjugation reaction mixture may comprise a batch preparation in accordance with this aspect of the invention.

The above-referenced polypeptides are screened for binding and/or internalization essentially as mentioned above in the described screening method embodiment.

In yet another embodiment, the present invention is drawn to a method of marketing a polypeptide which contains a region capable of binding the FGFR3 receptor comprising obtaining permission from a governmental or regional drug regulatory authority to sell said polypeptide, wherein said polypeptide is first produced from a bulk preparation which is assayed for selective binding of said polypeptide to neural cells by contacting the bulk preparation containing said polypeptide with a composition comprising FGFR3 receptor, and optionally GT1b ganglioside, and detecting whether said polypeptide selectively binds FGFR3 under such conditions, packaging said polypeptide for sale in a manner consistent with the requirements of said regulatory authority, and offering said polypeptide for sale.

In this embodiment the invention is drawn to a method of marketing a polypeptide containing the $H_C$ region of a BoNT/A toxin. The polypeptide at issue in this embodiment of the invention is produced from a bulk preparation which is assayed for purity or activity using the screening method described previously. In a step of this method, permission is obtained from a regulatory body for the marketing of such polypeptide. In this context "permission" may be tacit or express; that is, permission or approval may be obtained from the regulatory authority for the sale of a therapeutic agent or composition comprising said polypeptide, in which case "permission" is marketing approval for the sale of such agent or composition. Alternatively, "permission", as used herein, may comprise the assent, either affirmatively given or manifested by its lack of objection, of such regulatory authority to the continued sale of a product containing a polypeptide assayed in this new manner. As before, the polypeptide may comprise BoNT/A, or a derivative thereof, or a fusion protein or conjugate containing the $H_C$ region of the BoNT/A heavy chain.

The therapeutic product comprising the polypeptide originally contained in the bulk preparation so assayed is labeled in accordance with the requirements of the regulatory authority. The product is then offered for sale. Offering for sale may comprise advertising or sales activity, educational seminars directed at doctors, hospitals, insurers, or patients, conversations with state, regional or governmental officials concerning subsidy reimbursement (such as Medicare or Medical).

EXAMPLES

Example I

Identification of a BoNT/A Receptor Using a Genetic Complementation Procedure

1. Identification of Cells Useful in Screening for a BoNT/A Receptor

1a. Identification of BoNT/A Receptor Lacking Cells Using an Inhibition Assay for Insulin Release To determine whether HIT-T15 cells express a receptor for BoNT/A, an inhibition assay for insulin release was performed. In response to glucose stimulation, the hamster insulinoma cell line HIT-T15 secretes insulin in a exocytic process that depends on the activity of SNAP-25 for vesicle docking and fusion. If HIT-T15 cells lack a BoNT/A receptor, these cells would be unable to uptake BoNT/A upon exposure to this toxin and insulin secretion could occur in the presence of high glucose in the media. However, if HIT-T15 cells contain a BoNT/A receptor, insulin secretion would be inhibited after BoNT/A treatment since the toxin could intoxicate the cell and cleave SNAP-25.

Figure 3A:
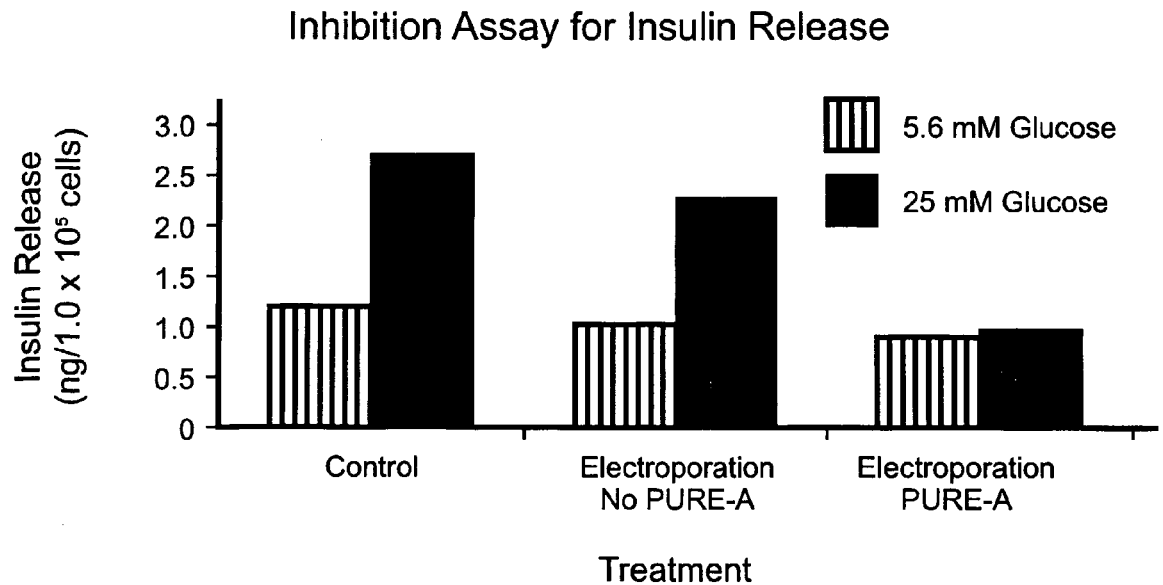
FIG. 3a shows the results of an inhibition of insulin release assay. The graph indicates that the addition of glucose to 25 mM induced insulin secretion from untreated cells (control) and cells subjected to electroporation without the addition of PURE-A (Electroporation No PURE-A). However, HIT-TI5 cells into which PURE-A was introduced (Electroporation PURE-A) showed a decrease in insulin secretion from indicating these cells were unresponsive to induction of insulin secretion.
Figure 3B:
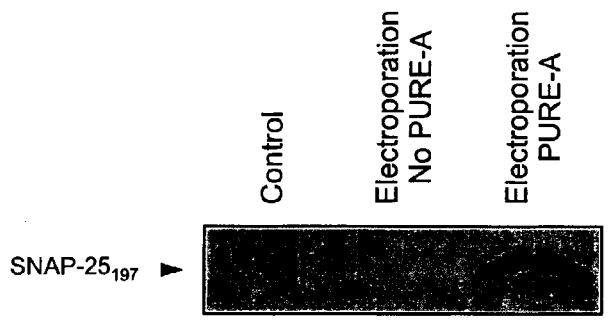
FIG. 3b shows the results of a SNAP-25 cleavage assay. Western blot analysis identified the presence of a BoNT/A SNAP-$25_{197}$ cleavage product in PURE-A treated cells (Electroporation PURE-A), but not in either control (Control and Electroporation No PURE-A), with equal amounts of protein loaded per lane and probed with an antibody that detects the BoNT/A SNAP-$25_{197}$ cleavage product.
Figure 4A:
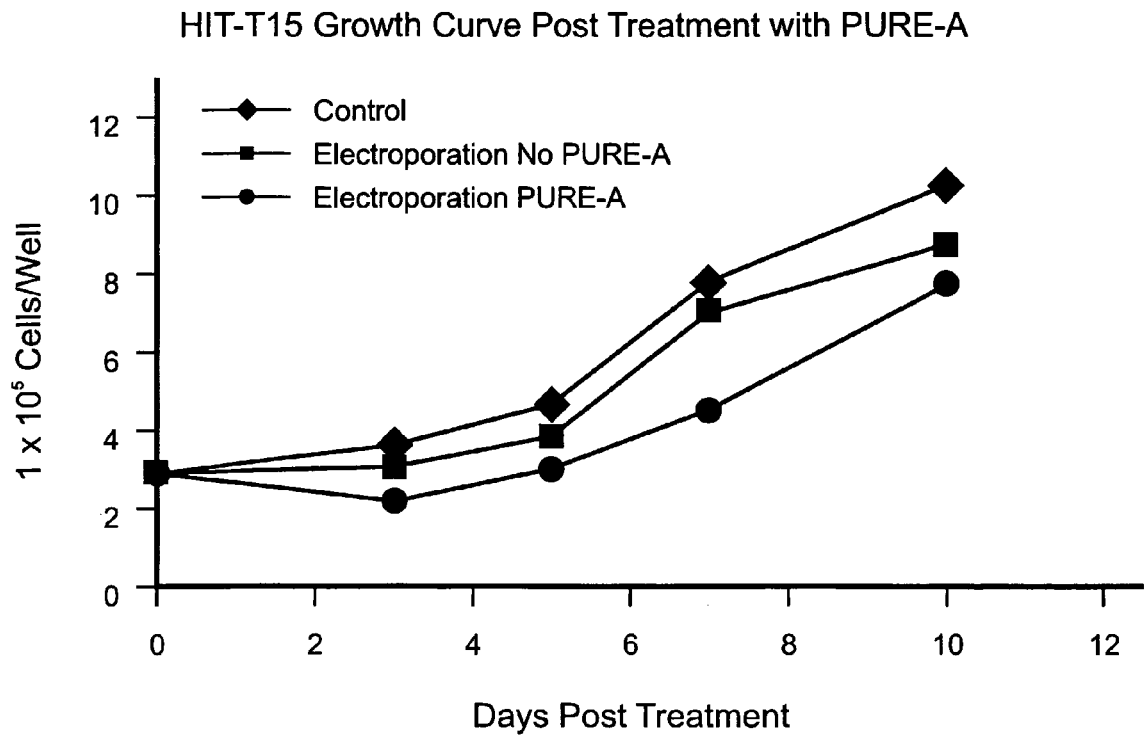
FIG. 4a shows the results on an inhibition release for insulin assay demonstrating that the presence of the toxin delayed growth in HIT-T15 cells when compared to controls, but toxin-treated cells were able to replicate normally after a recovery period.
Figure 4B:
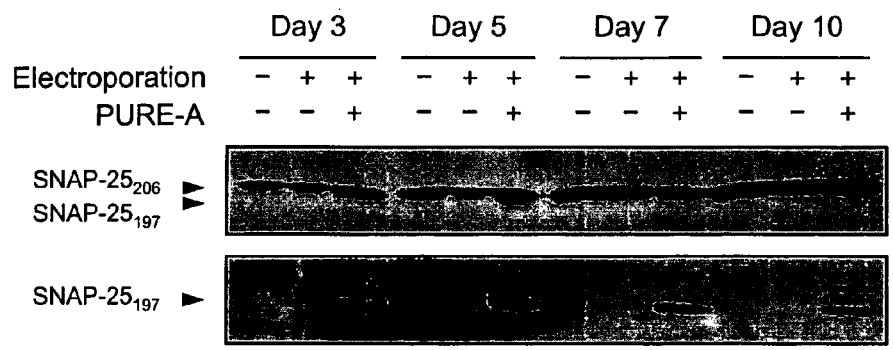
FIG. 4b shows a western blot analysis demonstrating that cleavage of SNAP-25 was detected at all time points tested when PURE-A was introduced into the cells, with equal amounts of protein loaded per lane and probed with an antibody that detects the BoNT/A SNAP-$25_{197}$ cleavage product.

To conduct an inhibition assay for insulin release, a suitable seed density of approximately $1.5 \times 10^5$ cells/mL of HIT-T15 cells was plated into individual wells of 6-well, poly-D-lysine/Laminin coated, tissue culture plates containing 3 mL of complete Dulbecco's Modified Eagle Media (DMEM), supplemented with 10% fetal bovine serum (FBS), 1× penicillin/streptomycin solution (Invitrogen, Inc, Carlsbad, Calif.) and 4 mM Glutamine (Invitrogen, Inc, Carlsbad, Calif.), and grown in a 37° C. incubator under 5% carbon dioxide until the cells reach a density of about $5 \times 10^5$ cells/ml (6-16 hours). A group of HIT-T15 cells were treated with approximately 1 nM of PURE-A by introducing the toxin using electroporation using a GENE PULSER® II set at 960 μF and 0.28 kV (Bio-Rad Laboratories, Hercules, Calif.). An untreated control group underwent electroporation without PURE-A. The media from the wells containing treated and untreated electroporated cells was replaced with 3 mL of fresh complete DMEM supplement with either 5.6 mM glucose (low glucise) or 25 mM glucose (high glucose) and these cells were incubated in a 37° C. incubator under 5% carbon dioxide for approximately 1 hour to induce insulin secretion. The conditioned media was transferred to 15 mL tubes and the amount of insulin present in the condition media samples was determined using an Insulin ELISA assay (Peninsula Laboratories, Inc., San Carlos, Calif.). Exocytosis is expressed as the amount of insulin secreted per $1.5 \times 10^5$ cell/hr. Insulin release was detected in BoNT/A-untreated cells simulated by 25 mM glucose, but insulin secretion was inhibited in BoNT/A-treated cells (see FIG. 3a). These data indicate that the release of insulin in HIT-T15 cells is mediated, in part, by SNAP-25, but that these cells lack a BoNT/A receptor.

1b. Identification of BoNT/A Receptor Lacking Cells Using an Using a SNAP-25 Cleavage Assay To determine whether HIT-T15 cells express a receptor for BoNT/A, a SNAP-25 cleavage assay was performed. If HIT-T15 cells lack a BoNT/A receptor, then only the presence of the uncleaved SNAP-25 substrate would be detected after Western blot analysis. However, if HIT-T15 cells contain a BoNT/A receptor, then the toxin could intoxicate the cell and the presence of the cleaved BoNT/A SNAP-$25_{197}$ product would be detected.

To conduct a SNAP-25 cleavage assay, cells were grown in poly-D-lysine/Laminin coated 6-well plates and treated with PURE-A as described above in Example I, 1a. Cells were collected in 15 ml tubes, washed once with 1 ml of phosphate-buffered saline, pH 7.4, and then transferred to 1.5 ml microcentrifuge tubes. Cells were lysed in 0.5 ml of lysis buffer containing 50 mM N-(2-hydroxyethyl) piperazine-N'-(2-ethanesulfonic acid) (HEPES), pH 6.8, 150 mM sodium chloride, 1.5 mM magnesium chloride, 1 mM ethylene glycol bis(β-aminoethyl ether) N,N,N',N'-tetraacetic acid (EGTA), 10% glycerol and 1% (v/v) Triton-X® 100 (4-octylphenol polyethoxylate), with rotation for 1 hour at 4° C. Lysed cells were centrifuged at 5000 rpm for 10 min at 4° C. to eliminate debris and the supernatants were transferred to fresh siliconized tubes. Protein concentrations were measured by Bradford's method and resuspended in 1×SDS sample buffer at 1 mg/mL or higher concentration.

To detect for the presence of a cleaved BoNT/A substrate, samples were boiled for 5 min, and 40 μl aliquots were separated by MOPS polyacrylamide gel electrophoresis using NuPAGE® Novex 4-12% Bis-Tris precast polyacrylamide gels (Invitrogen, Inc, Carlsbad, Calif.) under denaturing, reducing conditions. Separated peptides were transferred from the gel onto polyvinylidene fluoride (PVDF) membranes (Invitrogen, Inc, Carlsbad, Calif.) by Western blotting using a Trans-Blot® SD semi-dry electrophoretic transfer cell apparatus (Bio-Rad Laboratories, Hercules, Calif.). PVDF membranes were blocked by incubating at room temperature for 2 hours in a solution containing 25 mM Tris-Buffered Saline (25 mM 2-amino-2-hydroxymethyl-1,3-propanediol hydrochloric acid (Tris-HCl) (pH 7.4), 137 mM sodium chloride, 2.7 mM potassium chloride), 0.1% TWEEN-20, polyoxyethylene (20) sorbitan monolaureate, 2% bovine serum albumin, 5% nonfat dry milk. Blocked membranes were incubated at 4° C. for overnight in Tris-Buffered Saline TWEEN-20® (25 mM Tris-Buffered Saline, 0.1% TWEEN-20', polyoxyethylene (20) sorbitan monolaureate) containing a 1:5,000 dilution of rabbit polyclonal anti-SNAP25 antiserum pAb anti-SNAP25 197 #1, a polyclonal antibody which is specific for the $SNAP25_{197}$-cleavage product and does not cross-react with full-length $SNAP25_{206}$, (Allergan, Inc., generated under contract with Zymed Laboratories Inc., South San Francisco, Calif.). Primary antibody probed blots were washed three times for 15 minutes each time in Tris-Buffered Saline TWEEN-20. Washed membranes were incubated at room temperature for 2 hours in Tris-Buffered Saline TWEEN-20® containing a 1:20,000 dilution of goat polyclonal anti-rabbit immunoglobulin G, heavy and light chains (IgG, H+L) antibody conjugated to horseradish peroxidase (HRP; Pierce Biotechnology, Inc., Rockford, Ill.) as a secondary antibody. Secondary antibody-probed blots were washed three times for 15 minutes each time in Tris-Buffered Saline TWEEN-20®. Signal detection of the labeled BoNT/A $SNAP25_{197}$-cleavage product was visualized using the ECL Plus™ Western Blot Detection System (Amersham Biosciences, Piscataway, N.J.) and the membrane was imaged and cleavage product quantitated with a Typhoon 9410 Variable Mode Imager and Imager Analysis software (Amersham Biosciences, Piscataway, N.J.). The choice of pixel size (100 to 200 pixels) and PMT voltage settings (350 to 600, normally 400) depended on the individual blot. A BoNT/A $SNAP25_{197}$-cleavage product was detected in HIT-T15 cell treated with BoNT/A but not untreated cells, indicating that HIT-T15 cells express SNAP-25 but not the BoNT/A receptor (see FIG. 3*b*).

1c. Assessment of BoNT/A Exposure on HIT-T15 Growth

To evaluate if the presence of the toxin in the cells affect cell growth, HIT-T15 cells were electroporated as described above in Example I, 1a and monitored for 10 days. FIG. 4*a* demonstrates that the presence of the toxin delayed growth when compared to controls, but toxin-treated cells were able to replicate normally after a recovery period. Cell aliquots for days 3, 5, 7 and 10 were also tested for the presence of the BoNT/A SNAP-$25_{197}$ cleavage product using the SNAP-25 cleavage assay as described above in Example I, 1b. FIG. 4*b* shows that cleavage of SNAP-25 was detected by Western blot analysis at all time points assayed when PURE-A was introduced into the cells.

2. Identification of BoNT/A Receptor Using Genetic Complementation

To identify a BoNT/A receptor, a nucleic acid molecule encoding a BoNT/A receptor was cloned by genetic complementation. This procedure involves introducing a nucleic acid molecule encoding the BoNT/A receptor into a cell line that does not contain the receptor naturally by retroviral transduction, see, e.g. Mitchell H. Finer et al., Methods for Production of High Titer Virus and High Efficiency Retroviral Mediated Transduction of Mammalian Cells, U.S. Pat. No. 5,858,740 (Jul. 12, 1999).

2a. Production of a Retroviral Stock Containing pLIB Expression Constructs

To produce an retroviral stock containing expression constructs encoding human brain nucleic acid molecules, about $5\times10^5$ HEK 293-based cells (AmphoPack™ 293 cells; BD Biosciences Clontech, Palo Alto, Calif.) were plated in 60 mm tissue culture dishes containing 5 mL of complete Dulbecco's Modified Eagle Media (DMEM), supplemented with 10% fetal bovine serum (FBS), 1× penicillin/streptomycin solution (Invitrogen, Inc, Carlsbad, Calif.) and 4 mM Glutamine (Invitrogen, Inc, Carlsbad, Calif.), and grown in a 37° C. incubator under 5% carbon dioxide until the cells reach 60% to 80% confluency or a density of about 1 to $2\times10^6$ cells/ml (12-24 hours). On the day of transfection, the complete, supplemented DMEM media was replaced with 3 mL of OPTI-MEM Reduced Serum Medium. A 500 μL transfection solution is prepared by adding 250 μL of OPTI-MEM Reduced Serum Medium containing 15 μL of LipofectAmine 2000 (Invitrogen, Carlsbad, Calif.) incubated at room temperature for 5 minutes to 250 μL of OPTI-MEM Reduced Serum Medium containing 5 μg of pLIB retroviral expression constructs containing nucleic acid molecules derived from human brain cells (BD Biosciences Clontech, Palo Alto, Calif.). This transfection is incubated at room temperature for approximately 20 minutes. The 500 µL transfection solution was then added to the AmphoPack™ 293 cells and the cells were incubated in a 37° C. incubator under 5% carbon dioxide for approximately 8-10 hours. The transfection media was replaced with 3 mL of fresh complete, supplemented DMEM and cells were incubated in a 37° C. incubator under 5% carbon dioxide for approximately 48-72 hours. The retrovirus-containing cells are harvested by detaching the cells using the culture media and scraping cells from the culture plate. Detached cells and media are transferred to a 15 mL tube and centrifuged (5,000×g at 20° C. for 15 minutes) to pellet the cellular debris. The clarified supernatant containing the retroviral particles is transferred to 2 mL cryovials in 1 mL aliquots and should contain approximately $5 \times 10^4$ to $5 \times 10^6$ tu/mL of retroviral particles. Aliquots can be stored at −80° C. until needed.

2b. Transduction of Cells with a Retroviral Stock Containing pLIB Expression Constructs To transduce cells with a retroviral stock containing expression constructs encoding human brain nucleic acid molecules, about $1.5 \times 10^5$ HIT-T15 cells were plated in 60 mm tissue culture dishes containing 5 mL of complete Dulbecco's Modified Eagle Media (DMEM), supplemented with 10% fetal bovine serum (FBS), 1× penicillin/streptomycin solution (Invitrogen, Inc, Carlsbad, Calif.) and 4 mM Glutamine (Invitrogen, Inc, Carlsbad, Calif.), and grown in a 37° C. incubator under 5% carbon dioxide until the cells reach 60% to 80% confluency or a density of about $5 \times 10^5$ cells/mL (6-16 hours). Cells are inoculated with the retroviral stock containing nucleic acid molecules derived from human brain cells (see Example I, 2a), using a suitable multiplicity of infection. Approximately 4-8 µg/mL of polybrene was then added and the cells were incubated for approximately 16-24 hours in a 37° C. incubator under 5% carbon dioxide. The tranduction media is replaced with 5 mL of fresh complete, supplemented DMEM and the cells were incubated in a 37° C. incubator under 5% carbon dioxide for approximately four days. The transduced cells were then used to conduct a screening assay to identify a BoNT/A receptor. For greater details on procedures described in this example, see Retroviral Gene Transfer and Expresion User Manual PT3132-1 (PR43789), BD Biosciences Clontech, Palo Alto, Calif., (Mar. 3, 2004).

2c. Screening of HIT-T15 Cells Expressing a Retroviral cDNA Library

Figure 5:
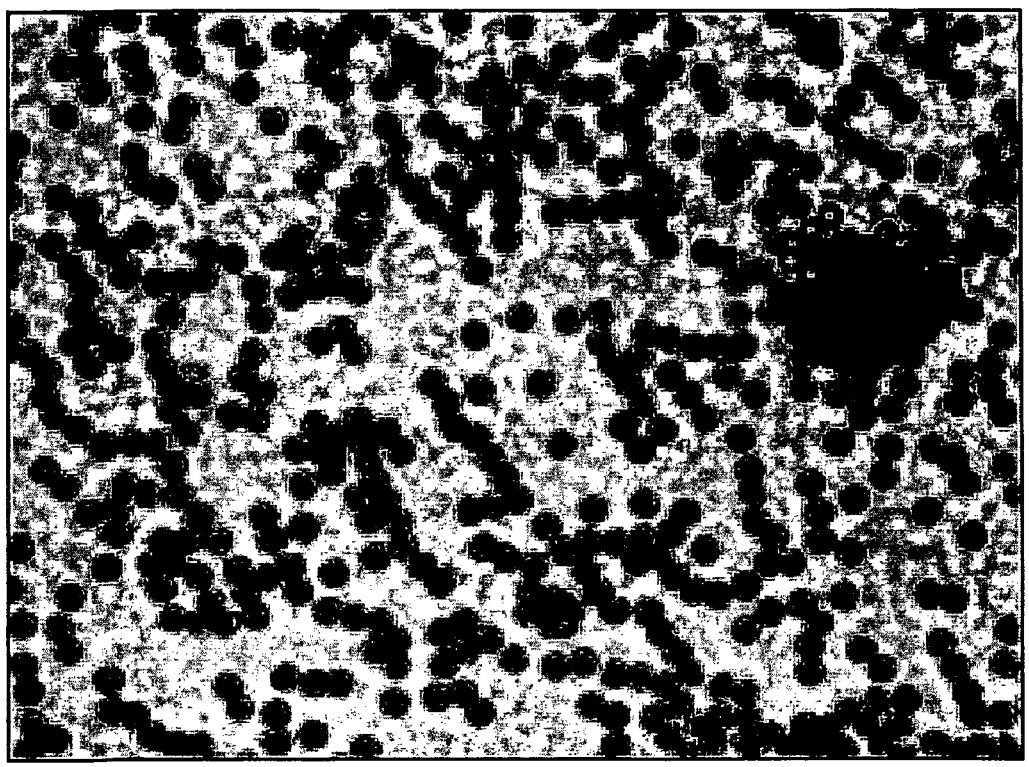
FIG. 5 shows HIT-T15 cells, transformed with a human brain cDNA library and selected using magnetic beads to which BONT/A had been bound. Individual colonies are visible in the dish and are surrounded by magnetic beads.

To screen for cells expressing a BoNT/A receptor, transduced HIT-T15 cells as described above in Example I, 2b were screened based on their ability to bind Dynex Beads coated with Pure A (ref). Approximately 7.5 mg of Dynabeads® magnetic beads (Dynal Biotechnology, LLC, Brown Deer, Wis.) coated with an antibody against the light chain of BONT/A was added to the media for 30 minutes at 4° C. and cells binding to the BoNT/A light chain were isolated as clumps of cells after exposure to a magnet. These isolated cells were washed once with PBS and transferred to new 60 mm tissue culture dishes containing 5 mL of complete DMEM. These cells were re-screened with 7.5 mg of Dynabeads® magnetic beads coated with PURE-A for 30 minutes at 4° C. and cells binding to PURE-A were isolated as clumps of cells after exposure to a magnet (see FIG. 5). These re-isolated cell colonies were transferred to 96-well plates containing 0.25 mL of complete DMEM and the cells were grown in a 37° C. incubator under 5% carbon dioxide until confluent.

Figure 6:
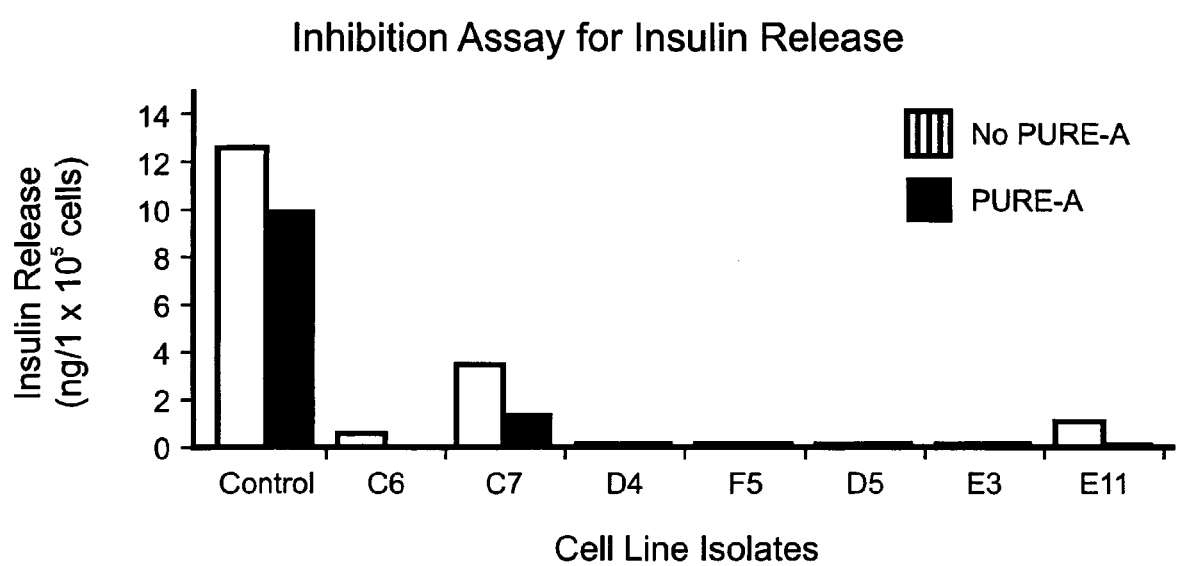
FIG. 6 shows the results of an assay of insulin release from HIT-T15 cells containing the putative BONT/A receptor. Cells were exposed to 1 nM PURE-A and assayed for inhibition of insulin release upon glucose stimulation.
Figure 7A:
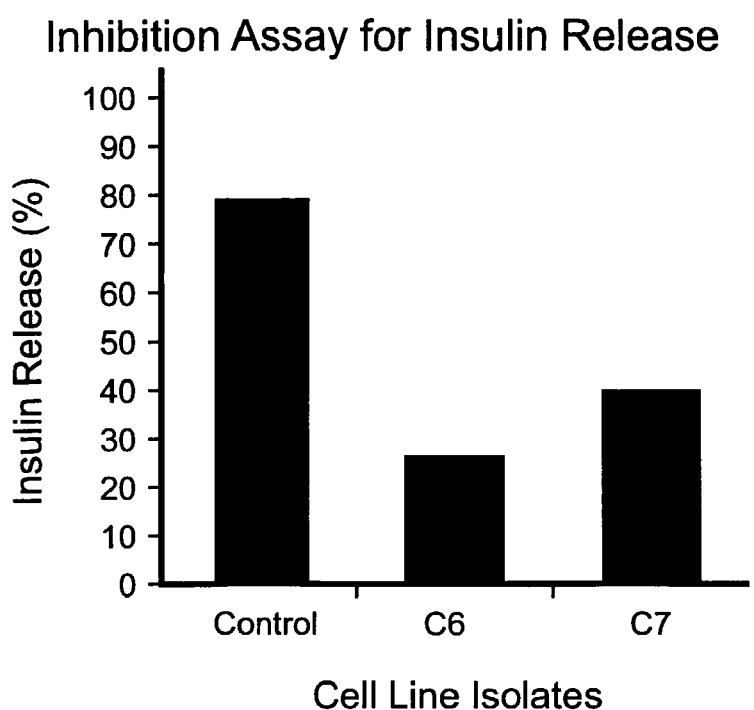
FIG. 7a shows the reduction of insulin release in representative HIT-T15 transformants C6 and C7 upon incubation with BONT/A.
Figure 7B:
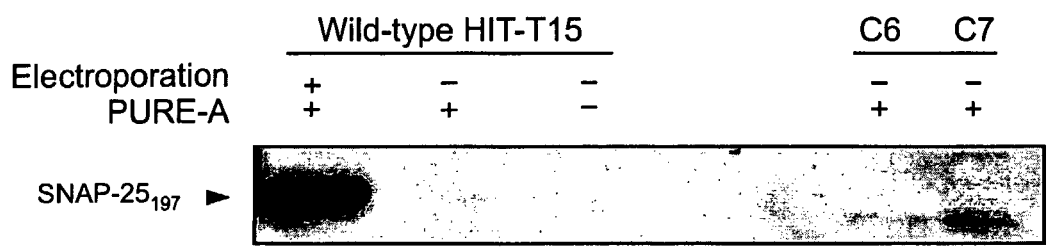
FIG. 7b shows a western blot analysis demonstrating that cleavage of SNAP-25 was detected in clones C6 and C7 incubated with BONT/A, with equal amounts of protein loaded per lane and probed with an antibody that detects the BoNT/A SNAP-$25_{197}$ cleavage product.

To test for the presence of a BoNT/A receptor, individual, cells contained in the 96-well plates were assayed using the inhibition assay for insulin release assay, as describes above in Example I, 1a. Cell lines containing a candidate BoNT/A receptor were selected based on the detection of the inhibition of insulin release. FIG. 6 show that transduced HIT-T15 cell lines C6 and C7 as candidate cell lines expressing a BoNT/A receptor. To confirm these results, expanded cultures of clones C6 and C7 as described above in Example I, 2a and tested using the inhibition of insulin release assay and the SNAP-25 cleavage assay, as described above in Example I, 1b. The results indicate that a BoNT/A receptor is present in these cell lines based on the inhibition of insulin release (see FIG. 7a) and the presence of a BoNT/A $SNAP25_{197}$-cleavage product (see FIG. 7b).

2d. Cloning of BoNT/A Receptor

To isolate nucleic acid molecules encoding the BoNT/A receptor, DNA will be purified from the BoNT/A receptor-containing HIT-T15 cell isolates identified above in Example I, 2c and the nucleic acid molecule encoding the BoNT/A receptor will be cloned using polymerase chain reaction (PCR) method. Genomic DNA from the C7 cell line will be isolated by an alkaline lysis procedure and will be amplified in PCR reactions using the ADVANTAGE® Genomic PCR kit (BD Biosciences Clontech, Palo Alto, Calif.) and the following two oligonucleotides 5'-AGCCCTCACTCCT-TCTCTAG-3' (SEQ ID NO: 29) and 5'-ACCTACAG-GTGGGGTCTTTC ATTCCC-3' (SEQ ID NO: 30). Reactions will be incubated at 95° C. for 1 minute, followed by 25 cycles at 68° C. for 30 seconds and 95° C. for 30 seconds, followed by 1 cycle at 68° C. for 6 minutes and final incubation at 4° C. The resulting PCR product will be purified from the PCR reaction by the QIAquick Gel Extraction Kit (QIAGEN, Inc., Valencia, Calif.), and will subjected to a second PCR amplification. The oligonucleotides used in the second PCR will be nested primers designed to anneal to sequences found within the PCR product originally purified, and will have the following nucleotide sequences: 5'-CCCTGGGTCAAGCCCTTTGTACACC-3' (SEQ ID NO: 31) and 5'-TGCCAAACCTACA GGTGGGGTCTTT-3' (SEQ ID NO: 32). The resulting nested DNA product will be subcloned into a pTOPO®-XL vector using the TOPO® TA cloning method (Invitrogen, Inc, Carlsbad, Calif.). The ligation mixture will be transformed into chemically competent *E. coli* TOP10 cells (Invitrogen, Inc, Carlsbad, Calif.) using a heat shock method, will be plated on 1.5% Luria-Bertani agar plates (pH 7.0) containing 100 µg/mL of Ampicillin, and will be placed in a 37° C. incubator for overnight growth. Ampicillin-resistant colonies will be analyzed using an alkaline lysis plasmid mini-preparation procedure and candidate receptor constructs will be screened by restriction endonuclease mapping to determine the presence and orientation of the correct insert fragment. Cultures containing the desired expression construct will be used to inoculate 1 L baffled flasks containing 200 mL of Luria-Bertani media containing 100 µg/mL of Ampicillin and will be placed in a 37° C. incubator, shaking at 250 rpm, for overnight growth. Purified plasmid DNA corresponding to an expression construct will be isolated using the QIAGEN Maxi-prep method (QIAGEN, Inc., Valencia, Calif.) and will be sequenced to verify that the correct expression construct was made (service contract with Sequetech Corp., Mountain View, Calif.). This cloning strategy will identified the sequence composition of the BoNT/A receptor contained in HIT-T15 C7 isolate.

Example II

Identification of a BoNT/A Receptor Using a Cross-Linking Procedure

1. Identification of Cell Lines with High Affinity Uptake for BoNT/A

Distinct sensitivities to each of the BoNT serotypes might be expected based on the individual receptor systems for each different toxin serotype and their differing expression in different cell lines. The presence of a high affinity receptor system in a cell for BoNT can be characterized by two attributes: a rapid uptake of the neurotoxin by the cell, and a low neurotoxin concentration needed for cell intoxication. To identify a cell line having a high affinity receptor system for a BoNT/A, we tested cell lines using one of two different in vitro cleavage assay, one to determine the amount of toxin required for intoxication, the other to determine the length of time necessary for the cell to uptake the neurotoxin.

1a. Assay to Determine the BoNT/A Concentration Necessary for Cell Intoxication

In order to assess the amount of BoNT/A needed to intoxicate a cell, a panel of mammalian cell lines of neuronal origin (see Table 3) was screened to determine whether toxin exposure would result in the cleavage of endogenously expressed SNAP-25. A suitable seed density of cells from each line was plated into individual wells of 6-well, poly-D-lysine/Laminin coated, tissue culture plates containing 3 mL of a suitable medium (see Table 3), and grown in a 37° C. incubator under 5% carbon dioxide for approximately 24 hours. BoNT/A (Metabiologics, Inc., Madison, Wis.) was added at different concentrations (0 nM, 1 nM, 5 nM, 12.5 nM, 25 nM, 50 nM) in the culture medium containing the cells for approximately 8 or approximately 16 hours. Cells were collected in 15 ml tubes, washed once with 1 ml of phosphate-buffered saline, pH 7.4, and then transferred to 1.5 ml microcentrifuge tubes. Cells were lysed in 0.5 ml of lysis buffer containing 50 mM N-(2-hydroxyethyl) piperazine-N'-(2-ethanesulfonic acid) (HEPES), pH 6.8, 150 mM sodium chloride, 1.5 mM magnesium chloride, 1 mM ethylene glycol bis(β-aminoethyl ether) N,N,N',N'-tetraacetic acid (EGTA), 10% glycerol and 1% (v/v) Triton-X® 100 (4-octylphenol polyethoxylate), with rotation for 1 hour at 4° C. Lysed cells were centrifuged at 5000 rpm for 10 min at 4° C. to eliminate debris and the supernatants were transferred to fresh siliconized tubes. Protein concentrations were measured by Bradford's method and resuspended in 1×SDS sample buffer at 1 mg/ml or higher concentration.

Figure 8A:
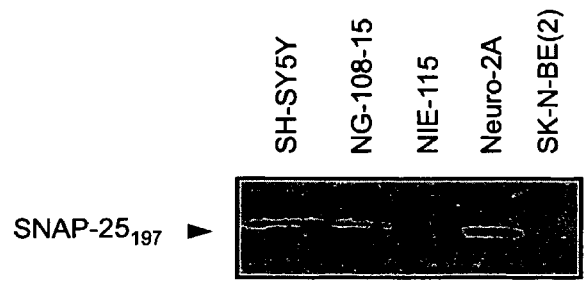
FIG. 8a shows a Western blot analysis used to identify cells capable of BoNT/A uptake. The blot shows five cell lines treated with 1 nM of PURE-A overnight, with equal amounts of protein loaded per lane and probed with an antibody that detects the BoNT/A SNAP-25197 cleavage product.

The presence of a BoNT/A SNAP25$_{197}$-cleavage product was determined by Western blot analysis as described above in Example I, 1b. A BoNT/A SNAP25$_{197}$-cleavage product was detected in the cell lines SH-SY5Y, NG108-15, N1E-115, Neuro-2A and SK-N-BE(2) after at least an 8 hour incubation with at least 5 nM BoNT/A, thereby indicating the ability of BoNT/A to intoxicate these cell lines (see FIG. 8a).

Figure 8B:
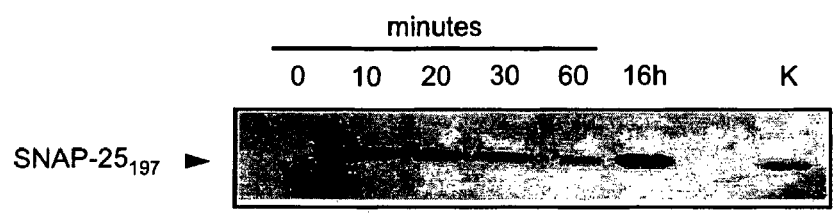
FIG. 8b shows Western blot analysis used to evaluate the time necessary for BoNT/A uptake. The blots show either Neuro-2A cells or SH-SY5Y cells treated with 1 nM of PURE-A for various lengths of time, with equal amounts of protein loaded per lane and probed with an antibody that detects the BoNT/A SNAP-$25_{197}$ cleavage product.
Figure 8B:
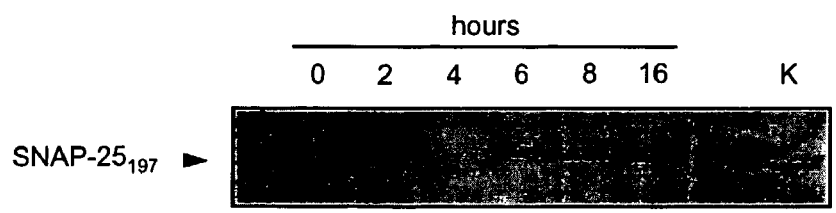
Figure 8C:
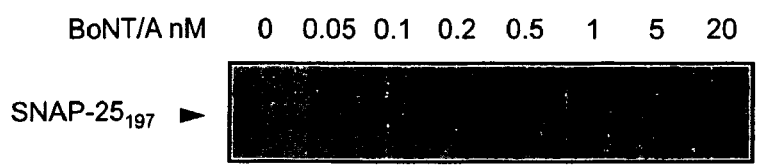
FIG. 8c shows a Western blot analysis used to evaluate the concentration range necessary of BoNT/A uptake. The blots show Neuro-2A cells treated with a range of PURE-A concentrations overnight, with equal amounts of protein loaded per lane and probed with an antibody that detects the BoNT/A SNAP-$25_{197}$ cleavage product.

The mouse neuroblastoma cell line Neuro-2A was further analyzed with lower concentrations of BoNT/A to determine the concentration of neurotoxin necessary to cleave endogenously expressed SNAP-25. Cells were grown in poly-D-lysine/Laminin coated 6-well plates as described above in Example II, 1a. BoNT/A (Metabiologics, Inc., Madison, Wis.) was added at different concentrations (0 nM, 0.05 nM, 0.1 nM, 0.2 nM, 0.5 nM, 1 nM, 5 nM and 20 nM) in the culture medium containing cells for either approximately 8 or approximately 16 hours. Toxin treated cells were harvested and lysed as described above in Example II, 1a. The presence of a BoNT/A SNAP25$_{197}$-cleavage product was determined by Western blot analysis as described above in Example II, 1a. A BoNT/A SNAP25$_{197}$-cleavage product was detected in the cell line Neuro-2A after at least a 8 hour incubation with at least 0.5 nM BoNT/A, thereby indicating the ability of BoNT/A to intoxicate these cell lines (see FIG. 8c).

1b. Assay to Determine the Time Required by a Cell to Uptake BoNT/A

In order to assess the amount of time needed by a cell line to uptake BoNT/A, a panel of mammalian cell lines of neuronal origin was screened to determine the length of toxin exposure necessary to cleave endogenously expressed SNAP-25. Cells from each line were grown in poly-D-lysine/Laminin coated 6-well plates as described above in Example II, 1a. Approximately 1 nM BoNT/A (Metabiologics, Inc., Madison, Wis.) was added to the culture medium for 10 min, 20 min, 30 min, 60 min 2 hours, 4 hours, 6 hours, 8 hours or 16 hours. Toxin treated cells were collected and lysed as described above in Example II, 1a. The presence of a BoNT/A SNAP25$_{197}$-cleavage product was determined by Western blot analysis as described above in Example II, 1a. A BoNT/A SNAP25$_{197}$-cleavage product was detected in the cell lines Neuro-2A, SH-SY5Y, and NG108-15 after at least an 8 hour incubation with 1 nM BoNT/A, thereby indicating the ability of these cell lines to rapidly uptake BoNT/A (see FIG. 8b).

TABLE 3

Culture Conditions for Cell Lines

| Cell Line | Complete Culture Media | Passage Conditions | Seed Density (cells/mm$^2$) |
|---|---|---|---|
| SK-N-DZ | 90% DMEM, A | Trypsin/EDTA treatment, 1:4 dilution split every 2-3 day | $4.25 \times 10^3$ |
| SK-N-F1 | 90% DMEM, A | Trypsin/EDTA treatment, 1:4 dilution spilt twice a week | $4.25 \times 10^3$ |
| SK-N-SH | Ham's F12, DMEM or EMEM, B | Trypsin/EDTA treatment, 1:20 dilution split every 4-7 day | $4.25 \times 10^3$ |
| SH-SY5Y | EMEM and Ham's F12 1:1, C | Trypsin/EDTA treatment, 1:6 dilution split every 2-3 day | $4.25 \times 10^3$ |
| SK-N-BE(2) | EMEM and Ham's F12 1:1, D | Trypsin/EDTA treatment, 1:6 dilution split every 3 day | $4.25 \times 10^3$ |
| BE(2)-C | EMEM and Ham's F12 1:1, D | Trypsin/EDTA treatment, 1:4 dilution split every 2-3 day | $4.25 \times 10^3$ |
| BE(2)-M17 | EMEM and Ham's F12 1:1, D | Trypsin/EDTA treatment, 1:20 dilution split every 4-7 day | $4.25 \times 10^3$ |
| Neuro 2a | EMEM, E | Trypsin/EDTA treatment, 1:3 dilution split every 3 day | $4.25 \times 10^3$ |
| C1300 | RPMI 1640, B | Trypsin/EDTA treatment, 1:3 dilution split every 3 day | $4.25 \times 10^3$ |
| NB4 1A3 | Ham's F10, F | Trypsin/EDTA treatment, 1:3 dilution split every 3 day | $4.25 \times 10^3$ |
| N1E-115 | DMEM, G | Trypsin/EDTA treatment, 1:3 dilution split every 3 day | $4.25 \times 10^3$ |
| NG108-15 | DMEM, B | 1:4 dilution split every 1-2 days | $4.25 \times 10^3$ |
| HCN-1A | DMEM, H | Trypsin/EDTA treatment, 1:3 dilution split every 3 day | $4.25 \times 10^3$ |
| HCN-2 | DMEM, H | Trypsin/EDTA treatment, 1:3 dilution split every 3 day | $4.25 \times 10^3$ |

TABLE 3-continued

Culture Conditions for Cell Lines

| Cell Line | Complete Culture Media | Passage Conditions | Seed Density (cells/mm$^2$) |
| --- | --- | --- | --- |
| TE 189.T | DMEM, H | Trypsin/EDTA treatment, 1:3 dilution split every 3 day | $4.25 \times 10^3$ |
| ND8/34 | DMEM, B | Trypsin/EDTA treatment, 1:3 dilution split every 3 day | $4.25 \times 10^3$ |

Figure 9A:
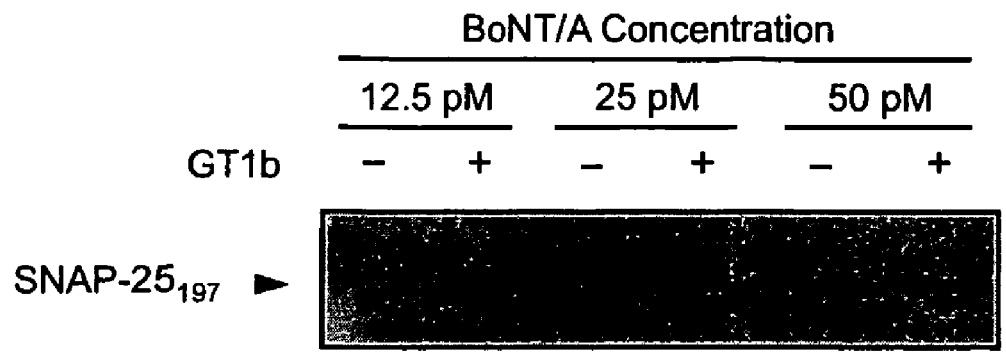
FIG. 9a shows a Western blot analysis evaluating the effects of ganglioside treatment on the uptake of BoNT/A. The blot shows Neuro-2A cells treated without or with 25 µg/mL of GT1b (− or +) and exposed overnight to three different concentrations of BoNT/A (12.5 pM, 25 pM or 50 pM), with equal amounts of protein loaded per lane and probed with an antibody that detects the BoNT/A SNAP-$25_{197}$ cleavage product.

A contains 1.5 g/L sodium bicarbonate, 0.1 mM Non-essential amino acids (NEAA), 4 mM Glutamine & 10% Fetal Calf serum (FCS)
B contains 2 mM Glutamine & 10% FCS
C contains 1.5 g/L sodium bicarbonate, 0.1 mM NEAA, 4 mM Glutamine, 1% sodium pyruvate, 1% penicillin/streptomycin (P/S) & 10% FCS
D contains 0.1 mM NEAA, 4 mM Glutamine, & 10% FCS
E contains 1.5 g/L sodium bicarbonate, 0.1 mM NEAA, 2 mM Glutamine, 1 mM sodium pyruvate & 10% FCS
F contains 2 mM Glutamine, 15% Horse Serum & 2.5% FCS
G contains 4.5 g/L glucose & 10% FCS
H contains 4 mM glucose & 10% FCS
Freeze medium comprises 95% culture medium and 5% DMSO 1c. Ganglioside Treatment to Increase High Affinity Uptake of BoNT/A by a Cell In order to assess the effect of ganglioside treatment on the ability of BoNT/A to intoxicate a cell, a Neuro-2A cell line was pre-treated with different gangliosides to determine whether these sugar moieties could increase the uptake of BoNT/A by these cells. Neuro-2A cells were plated at a suitable density into individual wells of 6-well, poly-D-lysine/Laminin coated, tissue culture plates containing 3 mL of a suitable medium (see Table 3), and grown in a 37° C. incubator under 5% carbon dioxide. After approximately 24 hours, the medium was replaced by a serum-free media and 25 µg/mL of one of the following gangliosides was added to individual wells: GD1a, GD1b, GD3, GQ1b, or GT1b (AXXORA, LLC, San Diego, Calif.). After an overnight 37° C. incubation period, the ganglioside-treated cells were washed three times with 1 ml of phosphate-buffered saline, pH 7.4 and then incubated at 37° C. with 1% serum media containing different concentrations (0 nM, 12.5 nM, 25 nM, 50 nM) of BoNT/A (Metabiologics, Inc., Madison, Wis.) for approximately 8 or approximately 16 hours. Cells were collected in 15 ml tubes, washed once with 1 ml of phosphate-buffered saline, pH 7.4, and then transferred to 1.5 ml microcentrifuge tubes. Cells were lysed in 0.5 ml of lysis buffer containing 50 mM N-(2-hydroxyethyl) piperazine-N'-(2-ethanesulfonic acid) (HEPES), pH 6.8, 150 mM sodium chloride, 1.5 mM magnesium chloride, 1 mM ethylene glycol bis(β-aminoethyl ether) N, N, N',N'-tetraacetic acid (EGTA), 10% glycerol and 1% (v/v) Triton-X® 100 (4-octylphenol polyethoxylate), with rotation for 1 hour at 4° C. Lysed cells were centrifuged at 5000 rpm for 10 min at 4° C. to eliminate debris and the supernatants were transferred to fresh siliconized tubes. Protein concentrations were measured by Bradford's method and resuspended in 1×SDS sample buffer at 1 mg/ml or higher concentration. The presence of a BoNT/A SNAP25$_{197}$-cleavage product was determined by Western blot analysis as described above in Example II, 1a. An increase in BoNT/A SNAP25$_{197}$-cleavage product was detected in the Neuro-2A cell line treated with the ganglioside GT1b, thereby indicating that GT1b-treatment can increase the uptake of BoNT/A by Neuro-2A cells (see FIG. 9a).

1d. Ganglioside Treatment to Increase High Affinity Uptake of BoNT/E by a Cell

Figure 9B:
FIG. 9b shows a Western blot analysis evaluating the effects of ganglioside treatment on the uptake of BoNT/E. The blot shows Neuro-2A cells treated with either 25 µg/mL of GT1b, GQ1b, GD1a, GD1b or GD3 and exposed for approximately 5 hours to 14 nM of BoNT/E di-chain, with equal amounts of protein loaded per lane and probed with an antibody (SMI-81; Sternberger Monoclonals, Lutherville, Md.) that detects the uncleaved SNAP-$25_{206}$ substrate and the BoNT/E SNAP-$25_{180}$ cleavage product.

In order to assess the effect of ganglioside treatment on the ability of BoNT/E to intoxicate a cell, a Neuro-2A cell line was pre-treated with different gangliosides to determine whether these sugar moieties could increase the uptake of BoNT/E by these cells. Neuro-2A cells were grown in poly-D-lysine/Laminin coated 6-well plates and treated with gangliosides as described above in Example II, 1c. The ganglioside-treated cells were incubated with BoNT/E (Metabiologics, Inc., Madison, Wis.) at different concentrations (0 nM, 12.5 nM, 25 nM, 50 nM) in 1% serum media for either approximately 6 or approximately 16 hours. Toxin treated cells were harvested and lysed as described above in Example II, 1c. The presence of a BoNT/E SNAP25$_{180}$-cleavage product was determined by Western blot analysis as described above in Example I, 1b, with the exception that blocked PVDF membranes were incubated in a primary antibody solution containing a 1:50,000 dilution of mouse monoclonal anti-SNAP-25 antibody (SMI-81; Sternberger Monoclonals, Lutherville, Md.) rather than the rabbit polyclonal anti-SNAP25 antiserum pAb anti-SNAP25197 #1 and a secondary antibody solution containing a 1:20,000 dilution of goat polyclonal anti-mouse immunoglobulin G, heavy and light chains (IgG, H+L) antibody conjugated to horseradish peroxidase (HRP; Pierce Biotechnology, Inc., Rockford, Ill.) rather than the goat polyclonal anti-rabbit IgG-HRP antibody in order to detect a BoNT/E SNAP25$_{180}$-cleavage product. An increase in BoNT/E SNAP25$_{180}$-cleavage product was detected in the Neuro-2A cell lines treated with the gangliosides GD3, GD1b and GD1a, thereby indicating that GD3-treatment, GD1b-treatment or GD1a-treatment can increase the uptake of BoNT/E by Neuro-2A cells (see FIG. 9b).

2. Isolation of BoNT/A Receptor from Neuro-2A Cells

Neuro-2A cells were chosen to conduct ligand cross-linking experiments using BoNT/A since these cells had a rapid toxin uptake profile (about 10 minutes) and high affinity for BoNT/A. The trifunctional sulfo-SBED (Pierce Biotechnology, Inc., Rockford, Ill.) were used. The reagent sulfo-SBED contains three reactive groups (one of them designed to be UV-activated) and is designed to biotinylate a target protein.

To conjugate a cross-linking agent to a BoNT/A, approximately 100 µg of Pure A is centrifuged at 10,000×g at 4° C. for 10 minutes to pellet the toxin and brought up in a final volume of 900 µL of phosphate-buffered saline (pH 7.4). The solution is then transferred to the dark and 900 µL of 0.25 mM SBED, 1% DMSO solution is added and incubated in a 4° C. for two hours in a secondary container on shaking apparatus. The reaction is stopped by adding 50 µL of 1M TRIS (pH 7.4). The solution is inverted 6 times and incubated on ice for 30 minutes. The resulting PURE-A-SBED solution was used to conduct cross-linking experiments to identify a BoNT/A receptor.

To cross-link PURE-A to BoNT/A receptors present on Neuro-2A cells, about 1.5×10$^5$ Neuro-2A cells were plated in a 35 mm tissue culture dish containing 3 mL of complete EMEM, supplemented with 10% FBS, 2 mM glutamine (Invitrogen, Inc, Carlsbad, Calif.), 1 mM sodium pyruvate (Invitrogen, Inc, Carlsbad, Calif.), 1.5 g/L sodium bicarbonate and 1×MEM non-essential amino acids solution (Invitrogen, Inc, Carlsbad, Calif.), and grown in a 37° C. incubator under 5% carbon dioxide until the cells reached a density of about $5 \times 10^5$ cells/ml. The Neuro-2A cells were harvested by detaching the cells with a trypsin treatment, transferring the cells to 15 ml tubes, and centrifuging the cells at 5,000×g at 4° C. for 10 min. The cell pellet is washed three times with 9 mL of Tris-buffered saline, and then divided into aliquots of $4 \times 10^8$ cells. Each aliquot of cells is suspended in 12 mL cold Tris-buffered saline for a final density of $2 \times 10^7$ cells/mL, and placed on ice for 15 minutes. To one aliquot of cell suspension, 1 mL of PURE-A-SBED is added, final concentratin is approximately 100 ug PURE A (33 nM). To a second cell aliquot, sulfo-SBED only is added and serves as a control for false positives. Both Neuro-2 cell suspensions were incubated at 4° C. for two hours in a secondary container using a shaking apparatus and then each cell solution is distributed in 13 aliquots of 1.0 mL. These aliquots were exposed to ultraviolet radiation (365 nm) at 4° C. for 15 minutes.

Figure 10A:
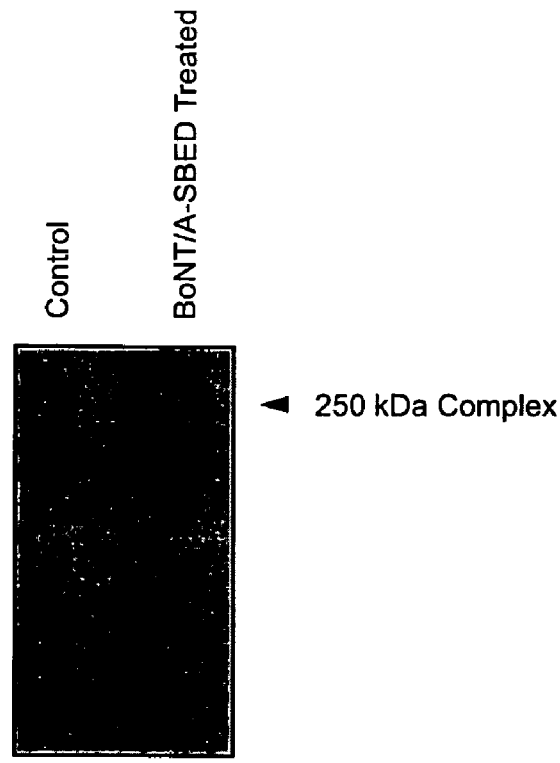
FIG. 10a shows the isolation of a complex of approximately 250 kDa from Neuro-2A cells containing the 150 kDa neurotoxin cross-linked to the putative BONT/A receptor. Bands were visualized with silver staining.

The cells were centrifugation at 5,000×g at 4° C. for 15 minutes and washed once with 1 mL cold Tris-buffered saline. Washed cells were lysed in 0.5 ml of lysis buffer containing 50 mM N-(2-hydroxyethyl) piperazine-N'-(2-ethanesulfonic acid) (HEPES), pH 6.8, 150 mM sodium chloride, 1.5 mM magnesium chloride, 1 mM ethylene glycol bis(β-aminoethyl ether) N,N,N',N'-tetraacetic acid (EGTA), 10% glycerol, 1% (v/v) Triton-X® 100 (4-octylphenol polyethoxylate) and suitable protease inhibitors, with rotation overnight at 4° C. Lysed cells were centrifuged at 5,000 rpm at 4° C. for 10 min to eliminate debris, the supernatants were transferred to fresh siliconized tubes and 0.05 mL of avidin-beads were added to the cleared supernatants. This mixture was incubated at 4° C. for 3 hours. The avidin beads were then washed twice by centrifuging at 1000×g at 4° C. for 10 min to pellet beads, decanting the supernatant, adding 0.5 mL lysis buffer and incubating the solution at 4° C. for 10 minutes. The avidin beads were then washed twice with 0.5 mL phosphate-buffered saline (pH 7.4). Approximately 100 μL of SDS-PAGE loading buffer was added to the washed, pelleted avidin beads and boiled for 10 minutes. A 40 μL aliquot was then subjected to MOPS polyacrylamide gel electrophoresis using NuPAGE® Novex 4-12% Bis-Tris precast polyacrylamide gels (Invitrogen, Inc, Carlsbad, Calif.) under non-denaturing and denaturing, reducing conditions. FIG. 10a shows an approximately 250 kDa protein in non-reducing gels which represents the intact cross-linking reagent PURE-A-SBED toxin bound to the putative BoNT/A receptor. Same samples run under denaturing conditions and reveals an approximately 100 kDa protein was co-purified with PURE-A-SBED.

Figure 10B:
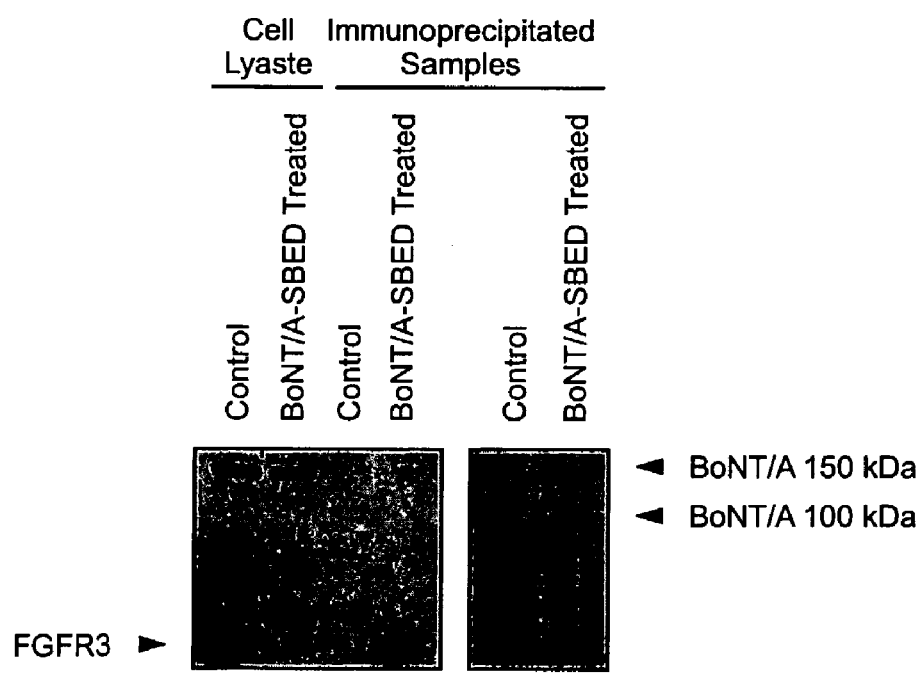
FIG. 10b shows a Western blot analysis used to identify a BoNT/A receptor. The blots shows the presence of a single band corresponding to the 97 kDa FGFR3 (first panel) and two bands corresponding to the 150 kDa BoNT/A holotoxin and the 100 kDa BoNT/A heavy chain (second panel), with equal amounts of protein loaded per lane and probed with an antibody that detects either FGFR3 or BoNT/A.

To determine the identity of the BoNT/A receptor isolated from the cross-linking experiments, western blot analysis was performed using antibodies to the cytoplasmic region of the polypeptides FGF 1 receptor (FGFR1), FGF 2 receptor (FGFR2), FGF 3 receptor (FGFR3) and FGF 4 receptor (FGFR4). Approximately 40 μL aliquots of the precipitated receptor-PureA complex, obtained as described above in Example II, 2, were separated by MOPS polyacrylamide gel electrophoresis using NuPAGE® Novex 4-12% Bis-Tris precast polyacrylamide gels (Invitrogen, Inc, Carlsbad, Calif.) under non-reducing and denaturing, reducing conditions. Separated peptides were transferred from the gel onto polyvinylidene fluoride (PVDF) membranes (Invitrogen, Inc, Carlsbad, Calif.) by Western blotting using a Trans-Blot® SD semi-dry electrophoretic transfer cell apparatus (Bio-Rad Laboratories, Hercules, Calif.). PVDF membranes were blocked by incubating at room temperature for 2 hours in a solution containing 25 mM Tris-Buffered Saline (25 mM 2-amino-2-hydroxymethyl-1,3-propanediol hydrochloric acid (Tris-HCl) (pH 7.4), 137 mM sodium chloride, 2.7 mM potassium chloride), 0.1% TWEEN-20®, polyoxyethylene (20) sorbitan monolaureate, 2% bovine serum albumin, 5% nonfat dry milk. Blocked membranes were incubated at 4° C. for overnight in Tris-Buffered Saline TWEEN-20® (25 mM Tris-Buffered Saline, 0.1% TWEEN-20, polyoxyethylene (20) sorbitan monolaureate) containing one of the following primary antibody solutions: 1) a 1:1000 dilution of rabbit polyclonal anti-FGFR1 antiserum (Santa Cruz Biotechnologies, Inc., Santa Cruz, Calif.); 2) a 1:1000 dilution of goat polyclonal anti-FGFR2 antiserum (Santa Cruz Biotechnologies, Inc., Santa Cruz, Calif.); 3) a 1:1000 dilution of rabbit polyclonal anti-FGFR3 (C15) antiserum (Santa Cruz Biotechnologies, Inc., Santa Cruz, Calif.); or 4) a 1:1000 dilution of goat polyclonal anti-FGFR4 antiserum (Santa Cruz Biotechnologies, Inc., Santa Cruz, Calif.). Primary antibody probed blots were washed three times for 15 minutes each time in Tris-Buffered Saline TWEEN-20®. Washed membranes were incubated at room temperature for 2 hours in Tris-Buffered Saline TWEEN-20® containing either a 1:20,000 dilution of goat polyclonal anti-rabbit immunoglobulin G, heavy and light chains (IgG, H+L) antibody conjugated to horseradish peroxidase (HRP; Pierce Biotechnology, Inc., Rockford, Ill.) as a secondary antibody for the FGFR1 and FGFR3 blots or a 1:20,000 dilution of rabbit polyclonal anti-goat immunoglobulin G, heavy and light chains (IgG, H+L) antibody conjugated to horseradish peroxidase (HRP; Pierce Biotechnology, Inc., Rockford, Ill.) for the FGFR2 and FGFR4 blots. Secondary antibody-probed blots were washed three times for 15 minutes each time in Tris-Buffered Saline TWEEN-20®. Signal detection of the labeled BoNT/A SNAP25$_{197}$-cleavage product was visualized using the ECL Plus™ Western Blot Detection System (Amersham Biosciences, Piscataway, N.J.) and the membrane was imaged and cleavage product quantitated with a Typhoon 9410 Variable Mode Imager and Imager Analysis software (Amersham Biosciences, Piscataway, N.J.). The choice of pixel size (100 to 200 pixels) and PMT voltage settings (350 to 600, normally 400) depended on the individual blot. A band was detected in toxin-receptor sample probed with anti-FGFR3 antiserum of approximately 97 kDa that is consistent with the size of FGFR3, indicating that FGFR3 is a BoNT/A receptor (see FIG. 10b).

3. Identification of BoNT/A Receptor from Various Cells

Several cells lines responsive to BoNT/A uptake were probed with antibodies raised against FGFR1, FGFR2, FGFR3 and FGFR4 in order to determine which FGFRs these cell lines express. In addition, cells from the BoNT/A unresponsive HIT-T15 wild-type cell line and the BoNT/A responsive HIT-T15 isolate C7 cell line, as described above in Example I, 2c and 2d, were examined.

Figure 11:
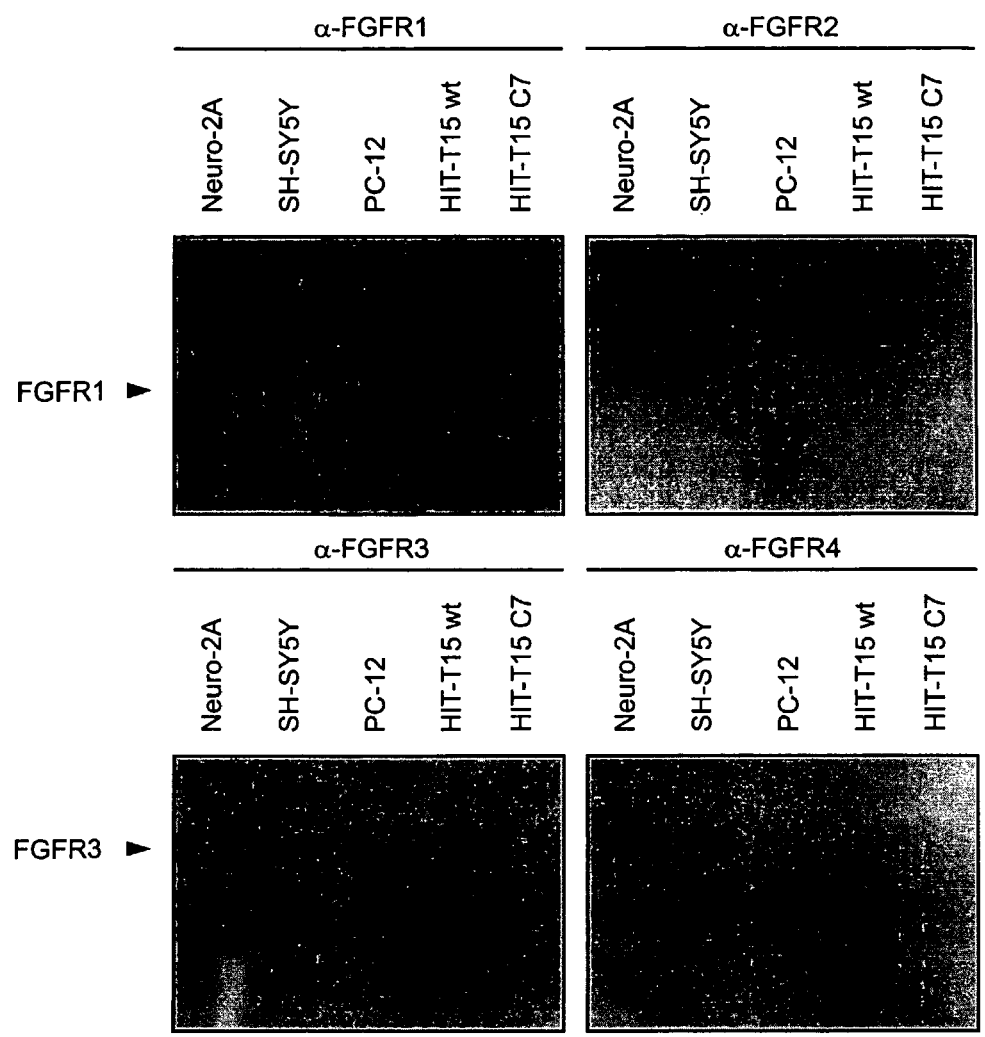
FIG. 11 shows a Western blot analysis used to determine the presence of FGFRs in five different cell lines. Only antibodies selectively binding to FGFR3 detected bands that correlated with cell lines that contained a BoNT/A receptor.

To determine the presence of FGFRs in cell lines responsive to BoNT/A exposure, cells were grown, harvested and lysed as described above in Example II, 1a, 1b or 2c and 40 μL aliquots were subjected to Western blot analysis as described above in Example II, 2. These results indicate that the BoNT/A responsive cell lines Neuro-2A, SH-SY5Y and HIT-T15-C7 all express FGFR3, while the BoNT/A unresponsive wild-type HIT-T15 does not (see FIG. 11). The data also from the revealed that FGFR2 and FGFR4 were not detected in any of the cell lines tested, while FGFR1 was present in all cell lines tested, including wild-type HIT-T15 cells that are unresponsive to BoNT/A exposure (see FIG. 11).

4. Competitive Competition Assays

To corroborate that BoNT/A toxin enters Neuro-2A cells through the FGFR3 we performed a competition experiment with PURE-A and analyzed the responsivness of tested using the SNAP-25 cleavage assay, as described above in Example I, 1b. If BoNT/A and an FGFR3 ligand bind to the same receptor, then increasing amounts of FGF ligand should result in decreased responsiveness of a cell to BoNT/A exposure. However, if BoNT/A and an FGFR3 ligand bind to the different receptors, then increasing amounts of FGF ligand should have no effect of the responsiveness of a cell to BoNT/A exposure. Table 1, which Applicants do not claim is a complete tabulation of FGF receptors and species, shows certain members of the family of FGFRs and their known ligands and tissue distribution.

To determine whether ligands for FGFR3 can competitively compete with BoNT/A for binding to FGFR3, about $5 \times 10^5$ Neuro-2A cells were plated in individual wells of a 6-well, poly-D-lysine/Laminin coated, tissue culture plates containing 3 mL of EMEM, supplemented with 2 mM glutamine (Invitrogen, Inc, Carlsbad, Calif.), 1 mM sodium pyruvate (Invitrogen, Inc, Carlsbad, Calif.), 1.5 g/L sodium bicarbonate and 1×MEM non-essential amino acids solution (Invitrogen, Inc, Carlsbad, Calif.), and grown in a 37° C. incubator under 5% carbon dioxide until the cells reached confluency. Approximately 5 nM PURE-A (Metabiologics, Inc., Madison, Wis.) was added in conjunction with FGF1, FGF2 or both FGF1 and FGF2 at different concentrations (0 nM, 0.1 nM, 1 nM, 5 nM, 50 nM, 200 nM) in the culture medium containing the cells and incubated for at 37° C. for approximately 10 minutes Cells were collected in 15 ml tubes, washed once with 1 ml of phosphate-buffered saline, pH 7.4, and then transferred to 1.5 ml microcentrifuge tubes. Cells were lysed in 0.5 ml of lysis buffer containing 50 mM N-(2-hydroxyethyl) piperazine-N'-(2-ethanesulfonic acid) (HEPES), pH 6.8, 150 mM sodium chloride, 1.5 mM magnesium chloride, 1 mM ethylene glycol bis(β-aminoethyl ether) N,N,N',N'-tetraacetic acid (EGTA), 10% glycerol and 1% (v/v) Triton-X® 100 (4-octylphenol polyethoxylate), with rotation for 1 hour at 4° C. Lysed cells were centrifuged at 5000 rpm for 10 min at 4° C. to eliminate debris and the supernatants were transferred to fresh siliconized tubes. Protein concentrations were measured by Bradford's method and resuspended in 1×SDS sample buffer at 1 mg/ml or higher concentration.

Figure 12:
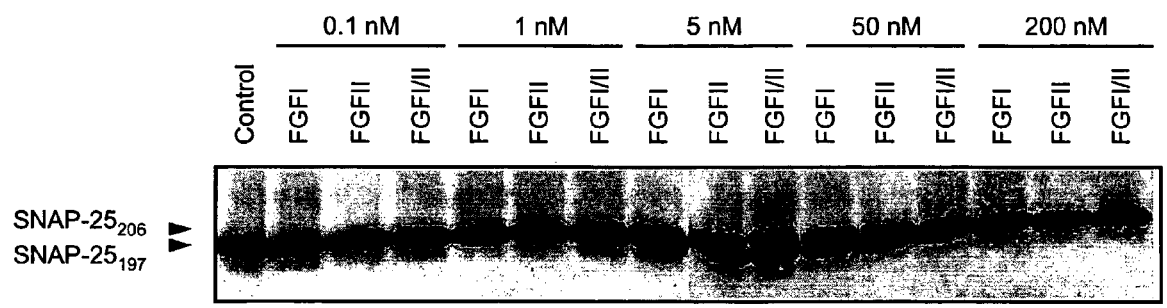
FIG. 12 shows the results of a receptor competition experiment in Neuro-2a cells using PURE-A and FGF ligands. A western blot analysis shows that both FGF1 and FGF2 effectively competed with BoNT/A for binding to the BoNT/A receptor, with equal amounts of protein loaded per lane and probed with antibody (SMI-81; Sternberger Monoclonals, Lutherville, Md.) that detects the uncleaved SNAP-$25_{206}$ substrate and the BoNT/E SNAP-$25_{180}$ cleavage product. The appearance of the uncleaved SNAP-$25_{206}$ substrate was detected when as little as 1 nM of FGF ligand was present and clearly visible when 5 nM of FGF ligands were present. Detectable levels of the BoNT/A SNAP-$25_{197}$ cleavage product was absent in FGF ligand treatments of 200 mM.

The presence of a BoNT/A SNAP25$_{197}$-cleavage product was determined by Western blot analysis as described above in Example II, 1a, with the exception that blocked PVDF membranes will be incubated in a primary antibody solution containing a 1:50,000 dilution of mouse monoclonal anti-SNAP-25 antibody (SMI-81; Sternberger Monoclonals, Lutherville, Md.) rather than the rabbit polyclonal anti-SNAP25 antiserum pAb anti-SNAP25197 #1 and a secondary antibody solution containing a 1:20,000 dilution of goat polyclonal anti-mouse immunoglobulin G, heavy and light chains (IgG, H+L) antibody conjugated to horseradish peroxidase (HRP; Pierce Biotechnology, Inc., Rockford, Ill.) rather than the goat polyclonal anti-rabbit IgG-HRP antibody in order to detect both the uncleaved SNAP-25 substrate and BoNT/A SNAP25$_{197}$-cleavage product. An increasing amount an increasing amount of FGF ligands, indicating these FGF1 and FGF2 compete for the same receptor as BoNT/A and further confirming that FGFR3 is a BoNT/A receptor (see FIG. 12).

Example III

A fusion protein comprising the C terminal portion of the heavy chain of BoNT/A and the light chain of BoNT/E is tested for its ability to selectively bind and intoxicate BoNT/A susceptible cells. A preparation comprising dilutions of the fusion protein is incubated with HIT-T15 insulinoma cells expressing exogenous FGFR3 in the presence of GT1b ganglioside. The ability of the fusion peptide to bind and enter the insulinoma cells is detected by detecting secretion of insulin in response to the presence of glucose, as described above in Example I, 1a. By contrast, insulin secretion is unaffected in cells not expressing FGFR3.

The results of this assay show that amount of insulin secreted into the culture medium is decreased in a dose-dependent manner when the fusion protein is added to the culture medium. Western blots of cell lysates will show the conversion of full length SNAP-25 to the cleaved form typical of the proteolytic activity of the BoNT/E light chain protease. This assay therefore is useful in showing that the fusion peptide is able to bind and enter BoNT/A susceptible cells.

The same fusion protein is capable of intoxicating cells of the neuromuscular junction.

Example IV

A fusion protein comprising the receptor binding portion of an FGF species capable of binding FGFR3 (including FGF1, FGF2, FGF4 and FGF9) and the translocation domain and light chain of BoNT/E is tested for its ability to selectively bind and intoxicate BoNT/A susceptible cells. The assay is conducted as described in Example 1 above, with similar results; the detected cleaved SNAP-25 fragments are characteristic of BoNT/A intoxication.

Example V

BoNT/A, produced from fermentation of *Clostridium botulinum* is produced using standard fermentation techniques. Either or both the bulk preparation and purified, formulated versions of expressed toxin are tested for purity and activity as follows. A preparation comprising dilutions of the BoNT/A preparation is incubated with HIT-T15 insulinoma cells expressing exogenous FGFR3 in the presence of GT1b ganglioside. The ability of the toxin to bind and enter the insulinoma cells is detected by detecting secretion of insulin in response to the presence of glucose, as described above in Example I, 1a. The specific activity of the preparation can be calculated from the determined protein concentration and the activity of the preparation at various doses.

These data are submitted to the U.S. Food and Drug Administration by a pharmaceutical company as part of data demonstrating how BoNT/A is manufactured and tested. This information is considered by the FDA, who decides to permit the manufacture and sale of this lot of BoNT/A, and subsequent lots made and tested in a similar manner, as a therapeutic pharmaceutical product based in part on this bulk and/or formulation assay data.

The pharmaceutical comprising the BoNT/A is then offered for sale as a prescription medication.

Example VI

Same as Example V, however the polypeptide produced is the fusion neurotoxin of Example III, produced in *E. coli*. Both bulk and/or formulation lots of the fusion neurotoxin are tested as indicated above, the data submitted to the FDA, and a decision to grant marketing approval, or continued sales of such fusion polypeptide as a therapeutic agent, is made by the FDA based at least in part on such data. The pharmaceutical company then offers the fusion neurotoxin for sale as a prescription therapeutic agent.

Example VII

An in vitro assay is established using cloned FGFR3 bound to a solid support in the presence of ganglioside GT1b. The bound FGFR3 is first saturated with BoNT/A heavy chain (H chain) in phosphate buffered saline (PBS), and washed free of unbound FGF. A test compound from a combinatorial library of compounds is contacted with the receptor under substantially physiological conditions (e.g., PBS), and the eluate collected. The H chain concentration in the eluate is compared to the H chain concentration of a control eluate in which H chain was not first bound to FGFR3.

Test compounds which are able to strongly bind FGFR3 and compete with H chain for FGFR3 binding (for example, by the method described in this section) are candidates compounds for the development of an antidote to acute botulism poisoning.

Example VIII

Generation of Cells Stably Containing a FGFR3

1. Construction of pQBI25/FGFR3

To construct pQBI-25/FGFR3, a nucleic acid fragment encoding the amino acid region comprising FGFR3 of SEQ ID NO: 4 is amplified from a human brain cDNA library using a polymerase chain reaction method and subcloned into a pCR2.1 vector using the TOPO® TA cloning method (Invitrogen, Inc, Carlsbad, Calif.). The forward and reverse oligonucleotide primers used for this reaction are designed to include unique restriction enzyme sites useful for subsequent subcloning steps. The resulting pCR2.1/FGFR3 construct is digested with restriction enzymes that 1) excise the insert containing the entire open reading frame encoding the FGFR3; and 2) enable this insert to be operably-linked to a pQBI-25 vector (Qbiogene, Inc., Irvine, Calif.). This insert is subcloned using a T4 DNA ligase procedure into a pQBI-25 vector that is digested with appropriate restriction endonucleases to yield pQBI-25/FGFR3. The ligation mixture is transformed into chemically competent *E. coli* BL21 (DE3) cells (Invitrogen, Inc, Carlsbad, Calif.) using a heat shock method, plated on 1.5% Luria-Bertani agar plates (pH 7.0) containing 100 μg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the inset. This cloning strategy yields a mammalian expression construct encoding the FGFR3 of SEQ ID NO: 4 operably-linked to the expression elements of the pQBI-25 vector.

2. Stably Transformed Cells Using a Recombinant Crossing-Over Procedure

To generate a stably-integrated cell line expressing a FGFR3 using a crossing over procedure, a suitable density ($1\times10^5$ to $1\times10^6$ cells) of appropriate cells, such as, e.g., HIT-T15 or Neuro2A, are plated in a 35 mm tissue culture dish containing 3 mL of complete, supplemented culture media and grown in a 37° C. incubator under 5% carbon dioxide until the cells reached a density appropriate for transfection. A 500 μL transfection solution is prepared by adding 250 μL of OPTI-MEM Reduced Serum Medium containing 15 μL of LipofectAmine 2000 (Invitrogen, Carlsbad, Calif.) incubated at room temperature for 5 minutes to 250 μL of OPTI-MEM Reduced Serum Medium containing 5 μg of expression construct encoding a FGFR3, such as, e.g., pQBI-25/FGFR3 (see Examples VIII, 1). This transfection was incubated at room temperature for approximately 20 minutes. The complete, supplemented media is replaced with 2 mL of OPTI-MEM Reduced Serum Medium and the 500 μL transfection solution is added to the cells and the cells are incubated in a 37° C. incubator under 5% carbon dioxide for approximately 16 hours. Transfection media is replaced with 3 mL of fresh complete, supplemented culture media and the cells are incubated in a 37° C. incubator under 5% carbon dioxide for approximately 48 hours. Media is replaced with 3 mL of fresh complete, supplemented culture media, containing approximately 5 μg/mL of G418. Cells are incubated in a 37° C. incubator under 5% carbon dioxide for approximately 4 weeks, with old media being replaced with fresh G418 selective, complete, supplemented media every 4 to 5 days. Once G418-resistant colonies are established, resistant clones are replated to new 35 mm culture plates containing fresh complete culture media, supplemented with approximately 5 μg/mL of G418 until these cells reached a density of 6 to $20\times10^5$ cells/mL.

To test for expression of a FGFR3 from isolated cell lines that stably-integrated an expression construct encoding a FGFR3, such as, e.g., pQBI-25/FGFR3 (see Examples VIII, 1), approximately $1.5\times10^5$ cells from each cell line are plated in a 35 mm tissue culture dish containing 3 mL of G418-selective, complete, supplemented DMEM and are grown in a 37° C. incubator under 5% carbon dioxide until cells reached a density of about $5\times10^5$ cells/ml (6-16 hours). Media is replaced with 3 mL of fresh G418-selective, complete, supplemented culture media and cells are incubated in a 37° C. incubator under 5% carbon dioxide. After 48 hours, the cells are harvested by rinsing the cells once with 3.0 mL of 100 mM phosphate-buffered saline, pH 7.4 and are lysed with a buffer containing 62.6 mM 2-amino-2-hydroxymethyl-1,3-propanediol hydrochloric acid (Tris-HCl), pH 6.8 and 2% sodium lauryl sulfate (SDS). Lysed cells are centrifuged at 5000 rpm for 10 min at 4° C. to eliminate debris and the supernatants are transferred to fresh siliconized tubes. Protein concentrations are measured by Bradford's method and are resuspended in 1×SDS sample buffer at 1 mg/ml or higher concentration.

To detect for the presence of a FGFR3, samples are separated by MOPS polyacrylamide gel electrophoresis and analyzed by Western blotting procedures as described above in Example II, 2 using a 1:1000 dilution of rabbit polyclonal anti-FGFR3 (C15) antiserum (Santa Cruz Biotechnologies, Inc., Santa Cruz, Calif.), in order to identify cell lines that have stably integrated and express the FGFR3 substrate.

Example IX

FGFR3 Phosphorylation Studies

1. Phosphorylation of FGFR-3 Exposed to FGF or BoNT/A

When bound by specific ligands, FGFR's are auto-phosphorylated on specific tyrosine residues. This begins the process of internalization of both the receptor and the ligand into the endosomal pathway. If BoNT/A binds to FGFR3, then exposure to BoNT/A should cause the auto-phosphorylation of FGFR3 in exposed cells.

To determine whether BoNT/A binding resulted in FGFR3 phosphorylation, approximately $1.5 \times 10^5$ Neuro-2A cells were plated into the wells of 6-well, poly-D-lysine/Laminin coated, tissue culture plates containing 3 mL of serum-free EMEM, supplemented with 1 mM sodium pyruvate (Invitrogen, Inc, Carlsbad, Calif.), 1.5 g/L sodium bicarbonate and 1×MEM non-essential amino acids solution (Invitrogen, Inc, Carlsbad, Calif.), and grown in a 37° C. incubator under 5% carbon dioxide until the cells reached a density of about $5 \times 10^5$ cells/ml. The serum-free media was replaced with fresh supplemented EMEM containing 1% FBS (Invitrogen, Inc, Carlsbad, Calif.) and either 5 nM FGF-2 (Biosource International, Camarillo, Calif.) or 5 nM of PURE/A (Metabiologics, Inc., Madison, Wis.). The cells were then incubated in a 37° C. incubator under 5% carbon dioxide for approximately 5 min, 10 min, 20 min and 30 min, with unexposed cells used as time 0. Cells were collected in 15 ml tubes, washed once with 1 ml of phosphate-buffered saline, pH 7.4, and then transferred to 1.5 ml microcentrifuge tubes. Cells were lysed in 0.5 ml of lysis buffer containing 50 mM N-(2-hydroxyethyl) piperazine-N'-(2-ethanesulfonic acid) (HEPES), pH 6.8, 150 mM sodium chloride, 1.5 mM magnesium chloride, 1 mM ethylene glycol bis(β-aminoethyl ether) N,N,N',N'-tetraacetic acid (EGTA), 10% glycerol and 1% (v/v) Triton-X® 100 (4-octylphenol polyethoxylate), with rotation for 1 hour at 4° C. Lysed cells were centrifuged at 5000 rpm for 10 min at 4° C. to eliminate debris and the supernatants were transferred to fresh siliconized tubes. Protein concentrations were measured by Bradford's method and resuspended in 1×SDS sample buffer at 1 mg/ml or higher concentration.

Figure 13A:
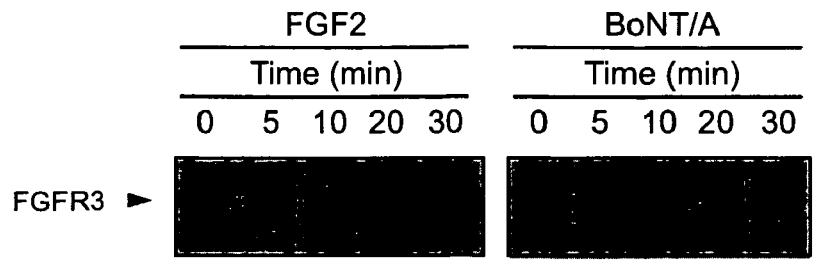
FIG. 13a shows a Western blot analysis indicating the presence of phosphorylated FGFR3 after exposure to FGF2 or BoNT/A. The blot shows Neuro-2A cells treated with either 5 nM FGF2 or 5 nM PURE-A for various lengths of time, with equal amounts of protein loaded per lane and probed with an antibody that detects FGFR3.

Supernatant containing 100 µg of protein was immunoprecipitated using 5 µg of anti-phosphotyrosine antibody attached to a sepharose bead (Zymed Laboratories, Inc., South San Francisco, Calif.). The immunoprecipitated product were subjected to Western blot analysis as described above in Example II, 4, with the blots being probed for FGFR3 (Santa Cruz Biotechnologies, Inc., Santa Cruz, Calif.). These experiments show that FGFR3 is phosphorylated upon either FGF2 or BoNT/A exposure, indicating that BoNT/A binds to FGFR3 (see FIG. 13a).

2. DMBI Inhibition of FGFR-3 Phosphorylation Exposed to FGF

Figure 13B:
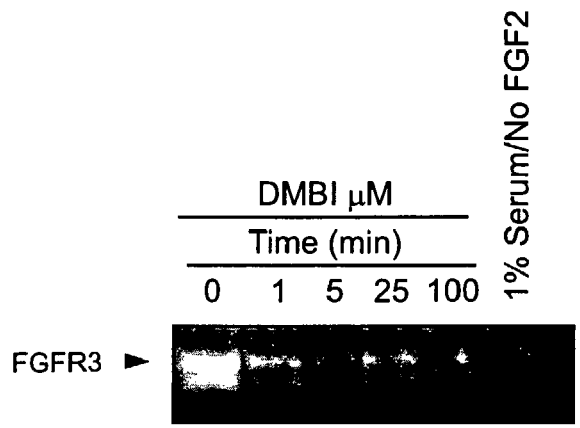
FIG. 13b shows a Western blot analysis indicating the reduction of phosphorylated FGFR3 when exposed to increasing amounts of DMBI. The blot shows Neuro-2A cells treated with 5 nM FGF2 for 10 minutes, with equal amounts of protein loaded per lane and probed with an antibody that detects phosphorylated FGFR3.

To determine whether DMBI inhibites BoNT/A-induced FGFR3 phosphorylation, Neuro-2A cells were plated and grown as described above in Example IX, 1. Neuro-2A cells were plated at a density of $5 \times 10^5$ cells/well (6 well plate) and incubated overnight in serum-free media. The media was replaced with fresh serum-free supplemented EMEM containing 0, 1 µM, 5 µM, 20 µM, or 100 µM of DMBI (EMD Calbiochem, San Diego, Calif.) for 1 hour. DMBI inhibits the autophosphorylation and dimerization of FGFR and PDGF type receptors. The cells were then washed and fresh supplemented EMEM containing 1% FBS (Invitrogen, Inc, Carlsbad, Calif.) and 5 nM FGF-2 (Biosource International, Camarillo, Calif.). The cells were then incubated in a 37° C. incubator under 5% carbon dioxide for approximately 5 min, 10 min and harvested and immunoprecipitated as described above in Example IX, 1. The immunoprecipitated products were subjected to Western blot analysis as described above in Example II, 4, with the exception that the blots were probed with a primary antibody solution containing a 1:1000 dilution of a rabbit polyclonal anti-phosphotyrosine antiserum (Upstate USA, Inc., Charlottesville, Va.) and a secondary antibody solution containing a 1:20,000 dilution of goat polyclonal anti-rabbit immunoglobulin G, heavy and light chains (IgG, H+L) antibody conjugated to horseradish peroxidase (HRP; Pierce Biotechnology, Inc., Rockford, Ill.). These results indicate that DMBI effectively inhibits the phosphorylation of FGFR3 upon FGF2 exposure (see FIG. 13b).

3. DMBI Inhibition of BoNT/A Activity

Figure 13C:
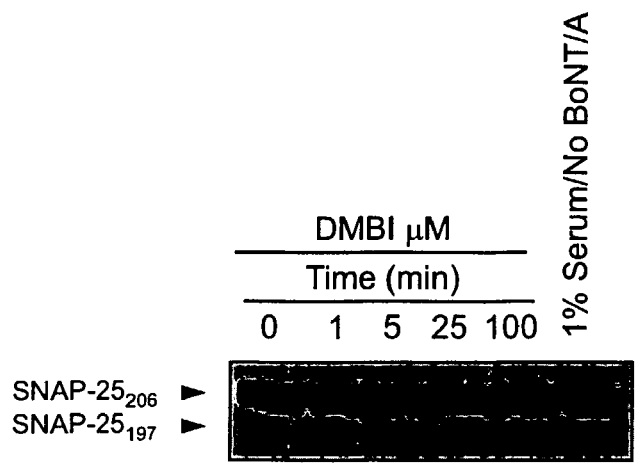
FIG. 13c shows a Western blot analysis indicating the reduction of SNAP-$25_{197}$ cleavage product when exposed to increasing amounts of DMBI. The blots show either Neuro-2A cells treated with 5 nM of PURE-A for 10 minutes, with equal amounts of protein loaded per lane and probed with an antibody that detects the BoNT/A SNAP-$25_{197}$ cleavage product.

To determine whether DMBI can inhibit BoNT/A activity, Neuro-2A cells were plated and grown as described above in Example IX, 1. The media was replaced with fresh serum-free supplemented EMEM containing 0, 1 µM, 5 µM, 20 µM, or 100 µM of DMBI (EMD Calbiochem, San Diego, Calif.) for 1 hour. DMBI inhibits the autophosphorylation and dimerization of FGFR and PDGF type receptors. The cells were then washed and fresh supplemented EMEM containing 1% FBS (Invitrogen, Inc, Carlsbad, Calif.) and 5 nM of PURE/A (Metabiologics, Inc., Madison, Wis.). The cells were then incubated in a 37° C. incubator under 5% carbon dioxide for approximately 5 min, 10 min and harvested as described above in Example IX, 1. Aliquots were tested for the presence of the BoNT/A SNAP-25$_{197}$ cleavage product using the SNAP-25 cleavage assay as described above in Example I, 1b. These results indicate a reduction in the amount of SNAP-25 cleavage product present, thereby indicating that DMBI effectively inhibits BoNT/A activity and confirming that this toxin in internalized by FGFR3 (see FIG. 13c).

The examples provided herein are simply illustrations of various aspects of the invention, which is to be understood to be defined solely by the claims which follow this specification.

What is claimed is:

1. A method of detecting Botulinum toxin serotype A (BoNT/A) activity in a sample, the method comprising the steps of:
   a) contacting a sample to a cell that contains an exogenous Fibroblast Growth Factor Receptor 3 (FGFR3) and an endogenous synaptosome-associated protein of 25000 Daltons (SNAP-25), wherein said cell is genetically engineered to express a nucleic acid molecule encoding said FGFR3; and wherein said cell is capable of BoNT/A intoxication; and
   b) detecting the presence of BoNT/A activity of said cell relative to a control cell by detecting the presence of endogenous SNAP-25 cleavage product from said cell.

2. The method according to claim 1, wherein said cell stably contains said FGFR3 encoding nucleic acid molecule.

3. The method according to claim 1, wherein said FGFR3 is a mammalian FGFR3.

4. The method according to claim 3, wherein said mammalian FGFR3 is a human FGFR3.

5. The method according to claim 3, wherein said mammalian FGFR3 is a bovine FGFR3.

6. The method according to claim 3, wherein said mammalian FGFR3 is a mouse FGFR3.

7. The method according to claim 3, wherein said mammalian FGFR3 is a rat FGFR3.

8. The method according to claim 1, wherein said FGFR3 is a bird FGFR3.

9. The method according to claim 8, wherein said bird FGFR3 is a chicken FGFR3.

10. The method according to claim 1, wherein said FGFR3 is an amphibian FGFR3.

11. The method according to claim 10, wherein said amphibian FGFR3 is a frog FGFR3.

12. The method according to claim 10, wherein said amphibian FGFR3 is a newt FGFR3.

13. The method according to claim 1, wherein said FGFR3 is a fish FGFR3.

14. The method according to claim 13, wherein said fish FGFR3 is a zebrafish FGFR3.

15. The method according to claim 1, wherein said cell further contains a G1b polysialoganglioside.

16. The method according to claim 15, wherein said polysialoganglioside is selected from the group consisting of GD1a, GD1b, GD3, GQ1b, or GT1b.

17. The method according to claim 1, wherein said cell is a neuronal cell.

18. The method according to claim 17, wherein said neuronal cell is a primary neuronal cell.

19. The method according to claim 17, wherein said neuronal cell is an immortalized neuronal cell.

20. The method according to claim 17, wherein said neuronal cell is selected from the group consisting of a neuroblastoma cell, a neuronal hybrid cell, a spinal cord cell, a central nervous system cell, a cerebral cortex cell, a dorsal root ganglion cell, a hippocampal cell and a pheochromocytoma cell.

21. The method according to claim 1, wherein said cell is a non-neuronal cell, said non-neuronal cell expressing an endogenous SNAP-25.

22. The method according to claim 21, wherein said non-neuronal cell is a primary non-neuronal cell.

23. The method according to claim 21, wherein said non-neuronal cell is an immortalized non-neuronal cell.

24. The method according to claim 1, wherein said sample is selected from the group consisting of a purified BoNT/A, a partially purified BoNT/A or unpurified BoNT/A.

25. The method according to claim 1, wherein said sample is selected from the group consisting of a bulk BoNT/A, a formulated BoNT/A, a cosmetics BoNT/A formulation or a clinical BoNT/A formulation.

26. The method according to claim 1, wherein said sample is a recombinant BoNT/A.

27. The method according to claim 1, wherein said sample is selected from the group consisting of a raw food, a cooked food, a partially cooked food or a processed food.

28. The method according to claim 1, wherein said sample is a sample taken from a mammal.

29. The method according to claim 28, wherein said mammalian sample is selected from the group consisting of a tissue, a saliva, an excretion or a feces.

* * * * *

UNITED STATES PATENT AND TRADEMARK OFFICE
CERTIFICATE OF CORRECTION

PATENT NO. : 7,598,027 B2
APPLICATION NO. : 10/598073
DATED : October 6, 2009
INVENTOR(S) : Ester Fernandez-Salas et al.

It is certified that error appears in the above-identified patent and that said Letters Patent is hereby corrected as shown below:

In column 2, line 50, delete "HIT-TI5" and insert -- HIT-T15 --, therefor.

In column 9-10, bottom of Table 1, line 12, delete "lung" and insert -- lung, --, therefor.

In column 12, line 12, delete "N-methylated" and insert -- $N^{\alpha}$-methylated --, therefor.

In column 22, line 21, delete "Control" and insert -- Control® --, therefor.

In column 23, line 56, delete "tranfection," and insert -- transfection, --, therefor.

In column 28, line 9, delete "P" and insert -- β --, therefor.

In column 29, line 35, delete "[125]" and insert -- $[^{125}I]$ --, therefor.

In column 30, line 35, delete "CI" and insert -- C1 --, therefor.

In column 30, line 64-65, delete "Femandez-Salas" and insert -- Fernandez-Salas --, therefor.

In column 32, line 16, after "2002)" insert -- . --.

In column 38, line 62, delete "CI" and insert -- C1 --, therefor.

In column 39, line 27, delete "Femandez-Salas" and insert -- Fernandez-Salas --, therefor.

In column 40, line 39, delete "$H_c$" and insert -- $H_C$ --, therefor.

In column 41, line 16, delete "Hc" and insert -- $H_C$ --, therefor.

In column 42, line 64, delete "(low glucise)" and insert -- (low glucose) --, therefor.

In column 43, line 54, delete "TWEEN-20," and insert -- TWEEN-20®, --, therefor.

UNITED STATES PATENT AND TRADEMARK OFFICE
CERTIFICATE OF CORRECTION

PATENT NO. : 7,598,027 B2
APPLICATION NO. : 10/598073
DATED : October 6, 2009
INVENTOR(S) : Ester Fernandez-Salas et al.

It is certified that error appears in the above-identified patent and that said Letters Patent is hereby corrected as shown below:

In column 43, line 66, delete "TWEEN-20." and insert -- TWEEN-20®. --, therefor.

In column 45, line 38, delete "tranduction" and insert -- transduction --, therefor.

In column 51, line 15, delete "concentratin" and insert -- concentration --, therefor.

In column 53, line 7, delete "responsivness" and insert -- responsiveness --, therefor.

Signed and Sealed this

Eighth Day of December, 2009

David J. Kappos
*Director of the United States Patent and Trademark Office*